United States Patent [19]

Inouye et al.

[11] Patent Number: 4,757,013

[45] Date of Patent: Jul. 12, 1988

[54] CLONING VEHICLES FOR POLYPEPTIDE EXPRESSION IN MICROBIAL HOSTS

[75] Inventors: Masayori Inouye, Setauket, N.Y.; Yoshihiro Masui, Toyonaka, Japan

[73] Assignee: The Research Foundation of State University of New York, Albany, N.Y.

[21] Appl. No.: 880,358

[22] Filed: Jun. 26, 1986

Related U.S. Application Data

[63] Continuation-in-part of Ser. No. 607,224, May 4, 1984, abandoned, which is a continuation-in-part of Ser. No. 494,040, Jul. 25, 1983, Pat. No. 4,643,964.

[51] Int. Cl.$^4$ .................. C12P 21/00; C12P 21/02; C12N 15/00; C12N 1/20
[52] U.S. Cl. .................................. 435/172.3; 435/68; 435/70; 435/253; 435/317; 435/320; 935/27; 935/40; 935/41; 935/43; 935/48; 935/60; 935/73
[58] Field of Search ................ 435/68, 70, 172.3, 253, 435/317; 935/27, 40, 41, 43, 48, 60, 73

[56] References Cited

PUBLICATIONS

Ghrayeb, J, H. Kimura, M. Takahara, H. Hsiung, Y. Masui and M. Inouye, *The EMBO Journal* 3(10): 2437–2442, 1984.
Movva, R. N, K. Nakamura and M. Inouye, *Journal of Biological Chemistry* 255 (1):27–29, 1980.
Matteucci et al, *Bio/Technology*, vol. 4, pp. 51–55, Jan. 1986.
Gray et al, *Gene*, vol. 39, pp. 247–254, 1985.
Oka et al, *Proc. Natl. Acad. Sci. USA*, vol. 82, pp. 7212–7216, Nov. 1985.
Nakamura et al, *The EMBO Journal*, vol. 1, pp. 771–775, Jun. 1982.
Nakamura et al, *Journal of Molecular and Applied Genetics*, vol. 1, pp. 289–299, Jun. 1982.
Masui et al, *Bio/Technology*, vol. 2, pp. 81–85, Jan., 1984.
Masui et al, "Multipurpose Expression Cloning Vehicles in *Escherichia Coli*," published as Chap. 2 of *Experimental Manipulation of Gene Expression* (Inouye, M., ed.), Academic Press 1983.

*Primary Examiner*—Thomas G. Wiseman
*Assistant Examiner*—Robin Lyn Teskin
*Attorney, Agent, or Firm*—Gottlieb, Rackman & Reisman

[57] ABSTRACT

Methods and compositions are provided for regulated expression and secretion of polypeptides in transformed bacterial hosts. A novel class of plasmid cloning vehicles includes a DNA sequence coding for the desired polypeptide (or an insertion site therefor) linked for transcriptional expression in reading phase with four functional fragments derived from the lipoprotein gene of *E. coli*. The plasmids also include a DNA fragment coding for the signal peptide of the ompA protein of *E. coli*, positioned such that the desired polypeptide is expressed with the ompA signal peptide at its amino terminus, thereby allowing efficient secretion across the cytoplasmic membrane. The plasmids further include a DNA sequence coding for a specific segment of the *E. coli* lac promoter-operator, which is positioned in the proper orientation for transcriptional expression of the desired polypeptide, as well as a separate functional *E. coli* lacI gene coding for the associated repressor molecule which can interact with the lac promoter-operator to prevent transcription therefrom. Expression of the desired polypeptide is under the control of both the lipoprotein promoter and the lac promoter-operator, although transcription from either promoter is normally blocked by the repressor molecule. However, the repressor can be selectively inactivated by means of an inducer molecule to permit transcriptional expression of the desired polypeptide from both promoters. The methods utilize such plasmids to introduce genetic capability into micro-organisms for the production of normally secreted proteins, such as medically or commercially useful hormones, enzymes, immunogenic proteins, or intermediates therefor, but only in the presence of an appropriate inducer.

15 Claims, 36 Drawing Sheets

FIG. IA

```
                                                                                                    TGGCTCTGCAGAGCA
                                                                                                    ACCGAGACGTCTCGT

-350            •          -300            •           •            •            •
         •                          •
ATCTGGCACACAAAGGTGACGTTGTAGTTATGGTTTCTGGTGCACTGGTACCGAGCGGCACTACTAACACCGCATCTGTTCACGTCCTGTAATATTGCTT
TAGACCGTGTGTTCCACTGCAACATCAATACCAAGACCACGTGGACCATGGCTCGCCGTGATGATTGTGGCGTAGACAAGTGCAGGACATTATAACGAA

-250            •          -200            •           •            •            •
         •                          •
TTGTGAATTAATTGTATATCGGCGCTTTTTTATTTAATCGATAACCAGAAGCAATAAAAATCAAATCGGATTTCACTATATAATCTCACTTTATCTA
AACACTTAATTAACATATAGCCGCGAAAAAATAAATTAGCTATTGGTCTTCGTTATTTTTAGTTATTTTAGCTAAAGTGATATATTAGAAGTGAAATAGAT

-150            •          -100            •           •            •            •
         •                          •
AGATGAATCCGATGGAAGCATCCTGTTTCTCCAATTTTTATCTAAAACCCAGGTTCGATGCTTCTTGAGCGAACGATCAAAATAAGTGCCTTC
TCTACTTAGGCTACCTTCGTAGGACAAAGAGGTTAAAAATAGATTTTGGGTCGCAAGCTACGAGAGAAACTCGCTTGCTAGTTTTTATTCACGGAAG

-50            •           -1+1            •           +50
         •                          ••                           •
CCATCAAAAAATATTCTCAACATAAAAAAACTTGTGTAATACTGTAAGGCTACATGGAGATTAACTCAATCTAGAGGGTATTAATAATGAAAGCTACT
GGTAGTTTTTTATAAGAGTTGTATTTTTGAAACACATATGAACATTGCGATGTACCTCTAATTGAGTTAGATCTCCCATAATTATTACTTTCGATGA
                                                          mRNA Start              MetLysAlaThr
                                                                                      1
```

FIG. 1B

```
AACTGGTACTGGGCGCGGTAATCCTGGGTTCTACTCTGCTGGCAGGTTGCTCCAGCAACGCTAAATGATCAGCTCGTCTCTTCTGACGTTCAGAGTCTGA
TTTGACCATGACCCGCGCCATTAGGACCCAAGATGAGACGACCGTCCAACGAGGTCGTTGCGATTTAGCTAGTCGACAGAAGACTGCAAGTCGAGACT
          LysLeuValLeuGlyAlaValIleLeuGlySerThrLeuLeuAlaGlyCysSerAsnAlaLysIleAspGlnLeuSerSerAspValGlnThrLeuA
                                         10                      20                        30
                                                                                                        +150

ACGCTAAAGTTGACCAGCTGAGCAACGACGTGAACGCAATGCGTTCCAGGCTGCTAAAGATGACGCAGCTCGTGCTAACCAGGTCGGCAGACCTGTT
TGCGATTTCAACTGGTCGACTCGTTGCTGCACTTGCGTTACGCAAGGCTGCAAGTCCGACGATTTCTACTGCGTCGAGCACGATTGGTCCAGAGACTGT
snAlaLysValAspGlnLeuSerAsnAspValAsnAlaMetArgSerAspValGlnAlaAlaLysAspAspAlaArgAlaAsnGlnArgLeuArgAspAs
                            40                            50                              60           70
                                              +200                                              +250

CATGGCTACTAATACCGCAAGTAATAGTACCTGTGAAGTGAAAAATGGGCGCACATTGTGCGACACTTTTTTTGTCTGCCGTTACCGCTACTGCGTCAC
GTACCGATGATTATGGCGTTCATTATCATGGACACTTCACTTTTTACTTCCACTTTAAAAAAACAGACGGCAAATGGGCGATGACGCAGTG
nMetAlaThrLysTyrArgLys              Stop
                  /8
                                       +300                                 +350

GCGTAACATATTCCCTTGCTCTGGTTCACCATTCTGCGCTGACTCTACTGAAGGGCCATTGCTGAGGGCTGCCGGAGTTGCTCCACTGCTCACCGAAACCGG
CGCATTGTATAAGGAACGAGACCAAGTGGTAAGACGGACTGAGATGACTTCCGCGACTTAACGACCGACGCCCTGAACGAGGTGACGAGTGGCTTTGGCC
                                                +400
```

```
5'-end:    G-C-U-A-C-A-U-G-G-A-G-A-U-U-A-A-C-U-C-A-A-U-C-U-A-G-A-G-G-U-A-U-U-A-A-U-A-A-U-G-A-A-G-C-U
                                 10                    20                    30                  40  MET - LYS - ALA
                                                                                                     1

A-C-U-A-A-A-A-C-U-G-G-A-U-C-C-U-G-G-C-G-C-C-G-G-U-A-A-C-U-C-U-G-G-C-U-G-G-C-A-G-G-U
             50                   60                   70                   80                 90
           THR - LYS - LEU - VAL - LEU - GLY - ALA - VAL - ILE - LEU - GLY - SER - THR - LEU - LEU - ALA - GLY
              5                   10                   15                                       20

U-G-C-U-C-C-A-G-C-A-A-C-G-C-U-A-A-A-A-U-C-G-A-U-C-A-G-C-U-U-U-C-A-G-A-C-U-U-G
           100                   110                   120                   130                 140
           CYS - SER - SER - ASN - ALA - LYS - ILE - ASP - GLN - LEU - SER - SER - ASP - VAL - GLN - THR - LEU
                   25                    30                                      35

A-A-C-G-C-A-A-A-A-G-U-U-G-A-U-C-A-G-C-U-G-A-A-C-G-A-A-A-C-G-C-A-A-U-G-C-G-A-U-U-C-C-G-A-C
           150                   160                   170                   180                 190             200
           ASN - ALA - LYS - VAL - ASP - GLN - LEU - SER - ASN - ASP - VAL - ASN - ALA - MET - ARG - SER - ASP
                   40                                      45                           50

G-U-U-C-A-G-G-C-U-C-U-G-C-U-A-A-A-A-G-A-U-G-A-U-C-G-C-U-A-A-C-C-G-U-A-A-C-C-A-G-C-A-A-C
                               210                   220                   230                 240                 250
           VAL - GLN - ALA - LEU - ALA - LYS - ASP - ASP - ALA - ALA - ARG - ALA - ASN - GLN - ARG - LEU - ASP - ASN
                   55                                      60                           65                          70

A-U-G-G-C-U-A-C-U-A-A-A-A-U-A-C-C-G-C-U-A-A-A-G-U-A-C-C-U-U-G-A-A-G-U-G-A-A-A-A-U-G-G-C-G-C-
                               260                   270                   280                 290                300
           MET - ALA - THR - LYS - TYR - ARG - LYS - LYS
                                       75          78

A-C-A-U-U-G-C-C-C-A-U-U-U-U-U-U-U-OH   :3'-end
                         310                 320
```

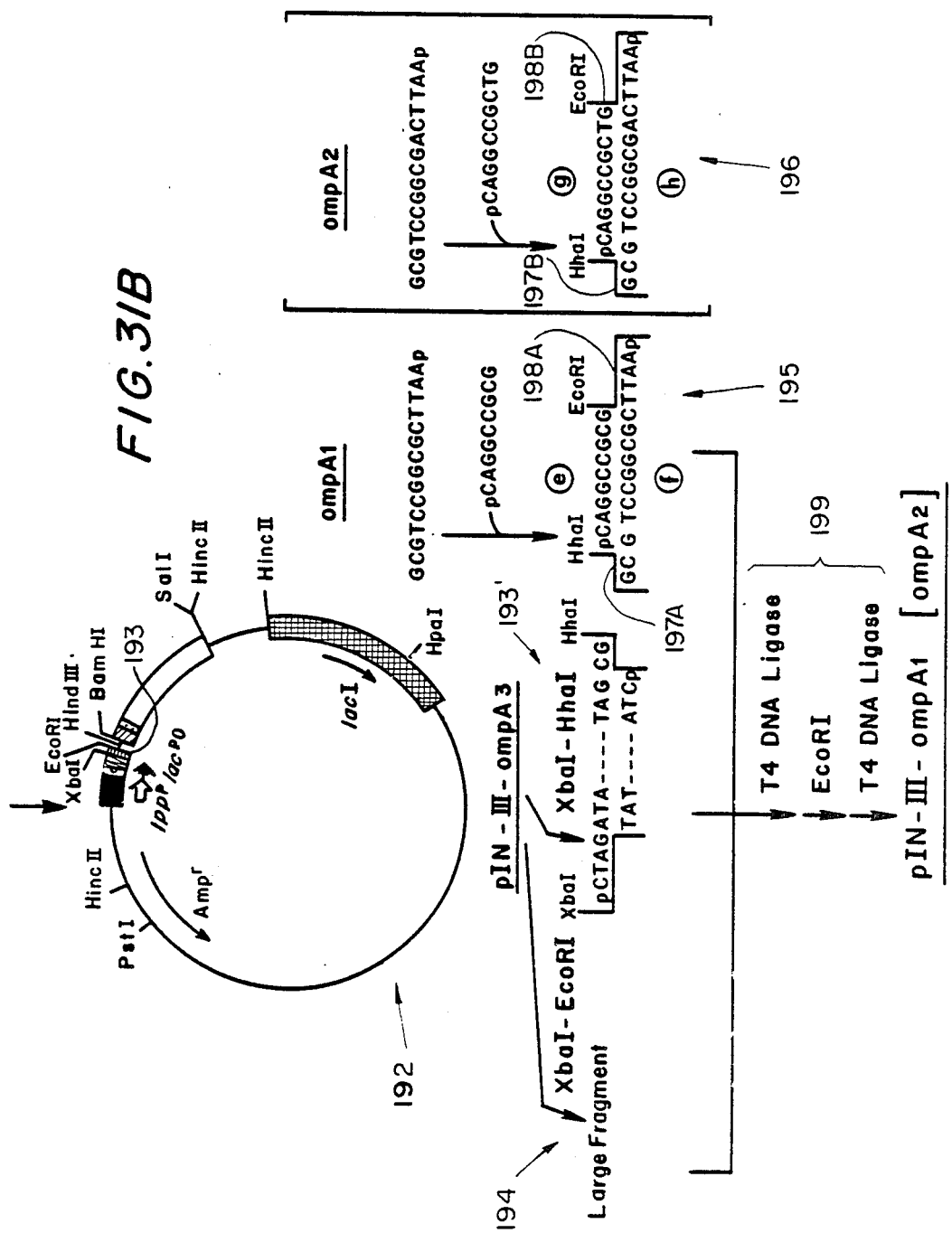
FIG.3/B

CLONING VEHICLES FOR POLYPEPTIDE EXPRESSION IN MICROBIAL HOSTS

This invention was made with Government support under Contract No. 5-R01-GM1904308 awarded by the National Institutes of Health. The Government has certain rights in this invention.

DESCRIPTION

This is a continuation-in-part of co-pending application Ser. No. 607,224 filed on May 4, 1984, which was a continuation-in-part of co-pending application Ser. No. 494,040, filed July 25, 1983 now U.S. Pat. No. 4643969 allowed Feb. 17, 1987.

TECHNICAL FIELD

This invention relates generally to the field of recombinant genetics, and specifically to a novel class of plasmid cloning vehicles with which exogenous genes may be expressed in transformed bacterial hosts.

As is well-known in the art, genetic information is encoded on double-stranded deoxyribonucleic acid ("DNA") molecules ("genes") according to the sequence in which the DNA coding strand presents the characteristic bases of its repeating nucleotide components. The four nitrogenous bases that characterize the two strands of DNA nucleotides are linked in complementary pairs by hydrogen bonds to form the double helix of DNA: adenine (A) is linked to thymine (T) and guanine (G) to cytosine (C). "Expression" of the encoded information involves a two-part process. According to the dictates of certain control regions in the gene, an enzyme ("RNA polymerase") may be caused to move along the DNA coding strand, synthesizing messenger ribonucleic acid ("mRNA") in a process called "transcription." The DNA coding strand typically includes signals, which can be recognized by RNA polymerase, for both initiation and termination of transcription. In a subsequent "translation" step, the cell's ribosomes, in conjunction with transfer-RNA, convert the RNA "message" into proteins or "polypeptides," which determine cell form and function. Included in the information transcribed by mRNA from DNA are signals for the initiation and termination of ribosomal translation, as well as signals specifying the identity and sequence of the amino acids which make up the polypeptide.

The DNA coding strand comprises long sequences of nucleotide triplets called "codons" in which the characteristic bases of the nucleotides in each triplet or codon encode specific bits of information. For example, three nucleotides read as ATG (adenine-thymine-guanine) result in an mRNA signal which is interpreted as "start translation," while termination codons TAG, TAA and TGA are interpreted as "stop translation." Between the initiation codon and the termination codon lies the so-called "structural gene," the codons of which define the amino acid sequence ultimately translated. That definition proceeds according to the well-established "genetic code" (e.g., Watson, J. D., *Molecular Biology Of The Gene*, 3rd ed. [New York: W. A. Benjamin, Inc., 1976]), which specifies the codons for the various amino acids. Since there are 64 possible codon sequences but only twenty known amino acids, the genetic code is degenerate in the sense that different codons may yield the same amino acid. However, the code is precise in that for each amino acid there is at least one codon, and in that each codon yields a single amino acid and no other. Thus, for example, all of the codons, TTT, TTC, TTA and TTG, when read as such, encode for serine and no other amino acid. It will be apparent that during translation the proper reading phase or reading frame must be maintained in order to obtain the proper amino acid sequence in the polypeptide ultimately produced.

The DNA sequence within the control region of a gene which mediates the initiation of transcription is termed the "promoter" of the gene, while the specific signal encoded in the DNA following the structural gene at which transcription ends is defined as the "transcription termination site." Although the mechanisms which underlie the initiation and termination of transcription are not completely understood, it is believed that the promoter provides the site at which RNA polymerase must bind in order to initiate transcription, and that the effectiveness or "strength" of a particular promoter or terminator signal is determined by the efficiency with which RNA polymerase can recognize and interact with these signals. This in turn depends in large part upon the particular base sequence of the DNA at or near these sites (see, e.g., Rosenberg, M., et al., *Ann. Rev. Genet.*, 1979 13, 319–353).

The control regions of some genes may also include DNA sequences which can be recognized by certain effector molecules, the action of which can positively or negatively influence the interaction between RNA polymerase and DNA and thereby further regulate gene expression at the level of transcription. The expression of genetic information by such genes may, for example, be inhibited in the absence of a given substance, and is therefore termed "inducible." On the other hand, there also exist may genes (such as the lipoprotein gene of the gram-negative bacterium *Escherichia coli* ["*E. coli*"]) whose control regions are not affected by effector molecules. The expression of genetic information by such genes is continuous during the lifetime of the cell, and is termed "constitutive." The control regions of such genes are generally comprised solely of a promoter signal and a terminator signal which immediately precede and follow, respectively, the DNA sequence to be transcribed.

The control regions cause mRNA synthesis to begin at a "transcription initiation site" located at or near the promoter, and to proceed until the transcription termination site is reached, producing an mRNA molecule of predetermined length with a base sequence complementary to the base sequence of the transcribed DNA. The DNA sequence between these two points defines not only the structural gene, the codons of which are ultimately translated for polypeptide expression, but also an "untranslated " region on either side of the structural gene.

Transcription therefore typically results in an mRNA molecule which carries a translatable RNA sequence, located between two untranslated regions. The untranslated region which precedes the structural sequence is known as the "5'-untranslated region," while the region which follows the structural signals is known as the "3'-untranslated region." As disclosed in detail hereinbelow, the DNA coding sequences for both of these untranslated regions, as well as the DNA coding sequences embodying the promoter signal and the terminator signal of certain genes, all of which may be referred to individually or collectively herein as "functional fragments" of those genes, may be effectively used in the creation of the novel cloning vehicles of the present invention.

As used herein, the term "cloning vehicle" defines a non-chromosomal double-stranded DNA molecule in "plasmid" form which can be replicated after being placed within a unicellular organism by a process called "transformation." An organism so transformed is called a "transformant." For present purposes, a "plasmid" is a circular non-chromosomal double-stranded DNA molecule derived from viruses or bacteria, the latter being termed "bacterial plasmids."

Advances in biochemistry in recent years have led to the construction of "recombinant" cloning vehicles in which, for example, plasmids are made to contain exogenous DNA. In particular instances in recombinant plasmid may include DNA that codes for polypeptides not ordinarily produced by the organism susceptible to transformation by the recombinant plasmid, and the exogenous DNA may in some cases comprise human genetic material. Typically, plasmids are cleaved to provide linear DNA having ligatable termini. These are bound to an exogenous gene having ligatable termini to provide a biologically functional moiety with a desired phenotypical property. The recombinant moiety is inserted into a micro-organism by transformation and transformants are isolated and cloned, with the object of obtaining large populations capable of expressing the new genetic information. Methods and means of forming recombinant cloning vehicles and transforming organisms with them have been widely reported in the literature, and generalized discussions of the subject appear in Cohen, S., *Scientific American* 233, 24–33 (July 1975), and in Gilbert, W., et al., *Scientific American* 242, 74–94 (April 1980). These and other publications alluded to herein are incorporated by reference.

A variety of techniques are available for DNA recombination, according to which adjoining ends of separate DNA fragments are tailored in one way or another to facilitate ligation. The latter term refers to the formation of phosphodiester bonds between adjoining nucleotides, through the agency of a catalytic enzyme such as T4 DNA ligase. Thus, DNA fragments with "blunt" ends may be directly ligated. Alternatively, fragments containing complementary single strands at their adjoining ends are advantaged by hydrogen bonding which positions the respective ends for subsequent ligation. Such single strands, referred to as "cohesive termini," may be formed by the addition of nucleotides to blunt ends using terminal transferase, or sometimes simply by "chewing back" one strand of a blunt end with an enzyme such as λ-exonuclease. Most commonly, however, such single strands may be formed by restriction endonucleases (also called restriction enzymes), which cleave the phosphodiester bonds in and around unique sequences of nucleotides of about 4–6 base pairs in length. Many restriction endonucleases and their recognition sequences are known, the so-called Eco RI endonuclease being one of the most widely employed.

Restriction endonucleases which cleave double-stranded DNA at unique sequences (e.g., at rotationally symmetric "palindromes") may leave cohesive termini. Thus, a plasmid or other cloning vehicle may be cleaved, leaving termini each comprising half of the restriction endonuclease recognition site. A cleavage product of exogenous DNA obtained with the same restriction endonuclease will have ends complementary to those of the plasmid termini. Alternatively, synthetic DNA comprising cohesive termini may be provided for insertion into the cleaved vehicle. To discourage rejoinder of the vehicle's cohesive termini pending insertion of exogenous DNA, the termini can be digested with alkaline phosphatase, providing molecular selection for closure incorporating the exogenous fragment. Incorporation of a fragment in the proper orientation relative to other aspects of the vehicle may be enhanced when the fragment supplants vehicle DNA excised by two different restriction endonucleases, and when the fragment itself comprises termini respectively constituting half the recognition sequence of the same two different endonucleases.

As a result of wide-ranging work in recent years in recombinant DNA research, the prior art includes a number of successful and commercially viable schemes to express functional polypeptide products such as insulin, somatostatin and human and animal growth hormone. The present invention relates to an improvement of one of those schemes.

BACKGROUND ART

In the earlier research efforts conducted by one of the present inventors, a group of recombinant bacterial plasmid cloning vehicles for expression of exogenous genes in transformed bacterial hosts was constructed, comprising a DNA insert fragment coding for the desired polypeptide, linked in reading phase with one or more functional fragments derived from any outer membrane protein gene of any gram-negative bacterium. In a preferred embodiment of these expression plasmids, the exogenous DNA codes for mammalian hormones, enzymes or immunogenic proteins (or intermediates therefor), the functional fragments are derived from the lipoprotein gene of *E. coli*, and the desired polypeptide is expressed in *E. coli* transformants. In a more preferred embodiment, the DNA sequence coding for the desired protein is linked with and is expressed under the control of four specific functional fragments associated with the *E. coli* lipoprotein gene, namely, the promoter, the 5'-untranslated region, the 3'-untranslated region and the transcription termination site of that gene.

These expression plasmids may also include a second promoter, preferably an inducible promoter and most preferably a DNA sequence consisting of 95 base pairs ("bp") and containing the *E. coli* β-galactosidase or "lac" promoter-operator, which is inserted immediately downstream of the lipoprotein promoter. This region serves not only as another transcription initiation site, but also as a repressor-binding site, thus working as a transcriptional "switch" for transcription initiated from the lipoprotein or "lpp" promoter, so that the exogenous DNA is expressed only in the presence of a "lactose inducer." When induced, the DNA coding for the desired polypeptide is transcribed from both promoters, thereby increasing the yield of the desired product over that obtained when expression is directed by the inducible lac promoter-operator alone. Accordingly, either constitutive or inducible gene expression may be achieved using these lpp gene cloning vehicles, provided that when inducible expression is desired, special *E. coli* strains are used as transformants, specifically, those which carry a mutant gene which overproduces the lactose repressor molecule.

The earlier research efforts of one of the present inventors also provided a modification of the foregoing scheme, namely, a class of "auto-regulated" inducible expression cloning vehicles, each member of the class being otherwise identical with its analog in the class of inducible expression vehicles described above, but further including the DNA sequence coding for the repressor molecule capable of binding with the inducible promoter used in the vehicle. In the preferred embodiment, the autoregulated expression plasmids incorporate an intact, functional *E. coli lacI* gene for this purpose. Since the expression of the exogenous genetic information in these cloning vehicles is regulated from within each cloning vehicle itself, a more effective transcriptional "switch" is provided, insuring that transcription is completely repressed in the absence of the appropriate inducer, without the necessity of utilizing special *E. coli* strains (which overproduce the repressor molecule) as transformants.

The earlier research of one of the present inventors revealed that the lipoprotein of *E. coli* is a "secretory" protein, i.e., it is produced from a precursor, which is then secreted across the cytoplasmic membrane and processed to the lipoprotein. In nature, translation of the lipoprotein mRNA transcript actually yields this precursor, called the prolipoprotein, which has a "peptide extension" or "signal peptide" at its amino terminus consisting of 20 amino acid residues, followed by the known 58 amino acid sequence of the lipoprotein. While the mechanisms involved in the secretion process are not yet well understood, the signal peptide is considered to direct the translocation in vivo of the prolipoprotein across the cytoplasmic membrane, in the process of which the peptide extension itself is removed, yielding mature lipoprotein.

Therefore, in light of the secretory nature of the lpp gene, each class of prior art expression plasmids (constitutive, inducible and "auto-regulated" inducible) most preferably includes three sub-classes of plasmids, the members of each subclass containing one of three alternative insertion sites for the exogenous genetic material. In this manner, the selection of a particular plasmid or a particular sub-class of plasmids for gene expression can influence the ultimate location at which the expression product can be found and collected. Using one of these insertion sites, for example, the desired polypeptide can be expressed with a leader sequence located at the amino terminal, the leader comprising the signal peptide of the *E. coli* lipoprotein, such that the desired product may be secreted through the cytoplasmic membrane and the signal peptide removed in vivo by processes native to the transformant, to yield the exogenous gene product. On the other hand, using expression plasmids which contain one or the other of the two remaining insertion sites, the expression product can be expected to be found either in the cytoplasm of the cell, or in the cell wall, respectively.

While the plasmids of each sub-class share a common insertion site, they differ from one another in their individual reading frames. Thus, each prior art sub-class comprises three plasmids, whose reading frames in effect differ by one base pair, enabling the selection of any desired reading frame for each insertion site and thereby facilitating the use of these expression vehicles with a wide variety of DNA insert fragments without the necessity of any direct modification of the reading frames of those fragments.

A further modification of the foregoing scheme was previously provided by the present inventors, in which the yield of the desired expression product was enhanced still further, without affecting the inducibility of the system, by varying slightly the size of the DNA fragment carrying the lac promoter-operator region. Specifically, by substituting a different, slightly longer DNA fragment, consisting of 105 bp but containing substantially the same, natural *E. coli* lac promoter-operator DNA sequence as contained in the 95 bp fragment described above, the amount of the desired polypeptide produced was found to increase dramatically.

Nevertheless, all of the prior art expression plasmids in which secretion of the desired polypeptide across the cytoplasmic membrane is achieved by fusing the *E. coli* lipoprotein signal peptide directly to the amino terminal end of the desired gene product, share a common disadvantage. The construction of these plasmids requires deletion of the DNA coding for the amino-terminal cysteine residue of the mature lipoprotein. While this structure permits synthesis of the desired polypeptide to commence immediately following the signal peptide, without any extraneous intervening amino acid residues, it also prevents the occurrence of "lipid modification," a natural transformation normally undergone by the native *E. coli* lipoprotein precursor (after synthesis but prior to secretion), for which the amino terminal cysteine residue is essential. This modification at the cleavage site is normally required to enable subsequent cleavage of the lipoprotein signal peptide.

As a consequence of the cysteine residue deletion, although gene products expressed with the prior art cloning vehicles (also called "vectors") are satisfactorily translocated across the cytoplasmic membrane (directed by the lipoprotein signal peptide), subsequent cleavage of that signal peptide by the cell's own lipoprotein-specific cleaving enzyme (called a "signal peptidase") does not occur because the alteration of the cleavage site normally introduced by the lipid modification is absent. Nevertheless, despite this limitation, cleavage of the lipoprotein signal peptide does occur when certain proteins are expressed, due to the presence of a second, non-lipoproteinspecific signal peptidase in *E. coli* cells, although this occurs only if the particular protein being expressed has the appropriate conformation, a physical attribute which is unknown and which cannot be predicted for most proteins.

Accordingly, the prior art lipoprotein secretion plasmids have limited application, since for production of most proteins, an extra, somewhat costly synthetic step is required to cleave the lipoprotein signal peptide from the remainder of the secreted moiety in order to obtain a pure form of the desired gene product. It is therefore the principal object of the present invention to provide a new class of plasmid cloning vehicles with which these disadvantages may be overcome.

DISCLOSURE OF INVENTION

In accordance with the primary objective of this invention, it has been determined that the efficiency of secretion of the desired expression product can be enhanced by modifying the lipoprotein secretion vectors of the prior art to introduce the DNA fragment coding for the signal peptide of the ompA protein, a major outer membrane protein of *E. coli*, in place of the lipoprotein signal peptide. The desired polypeptide is thereby synthesized with the ompA signal peptide at its amino terminus, which then directs the translocation of the gene product across the cytoplasmic membrane. Thereafter, the ompA signal peptide is efficiently cleaved off, since unlike the lipoprotein, it does not require any modification of the cleavage site during the secretion process.

Accordingly, in the present invention a class of inducible recombinant bacterial plasmid cloning vehicles for expression of exogenous genes in transformed bacterial hosts is provided, each plasmid comprising a DNA insert fragment coding for the desired polypeptide, linked with one or more functional fragments derived from the *E. coli* lpp gene as well as the DNA coding for the signal peptide of the ompA gene, and also linked in reading phase with the inducible *E. coli* lac promoter-operator carried on a particular 105 bp DNA fragment. Most preferably, each plasmid also includes an intact, functional *E. coli* lacI gene, providing inducible gene expression which is autoregulated.

BRIEF DESCRIPTION OF DRAWINGS

The structure and function of the recombinant bacterial plasmids of the present invention, with which gene products such as human insulin may be expressed in bacterial transformants, is illustrated in the following specification, when taken in conjunction with the accompanying drawings wherein:

FIGS. 1A and 1B together are a schematic illustration of the 814-base pair DNA sequence encompassing the *E. coli* lipoprotein gene, in which the transcription initiation and termination sites are indicated by arrows (▲), and in which the 78 amino acid sequence of the prolipoprotein deduced from the DNA sequence is also shown, written below the corresponding codons of the DNA coding strand;

FIG. 2 shows the complete 322-nucleotide sequence of the lipoprotein mRNA of *E. coli*, in which the amino acid sequence of the prolipoprotein deduced from the mRNA sequence is also indicated, written below the corresponding codons of the nucleotide sequence;

FIGS. 5–30B together comprise a schematic illustration of the preferred method for construction of the constitutive, inducible, and auto-regulated inducible, recombinant plasmid cloning vehicles resulting from the earlier research efforts of the present inventors, in which the relative positions of various restriction endonuclease cleavage sites are shown, and in which Ampr and Tcr, respectively, denote genes for ampicillin and tetracycline resistance;

FIGS. 31A, 31B and 32 together comprise a schematic illustration of the experimental method actually used to construct the plasmids of the present invention, in which the arrows (▲) in FIG. 32 indicate the cleavage site of the ompA signal peptide.

BEST MODE OF CARRYING OUT THE INVENTION

1. Summary Of Preliminary Research

Figure 3:
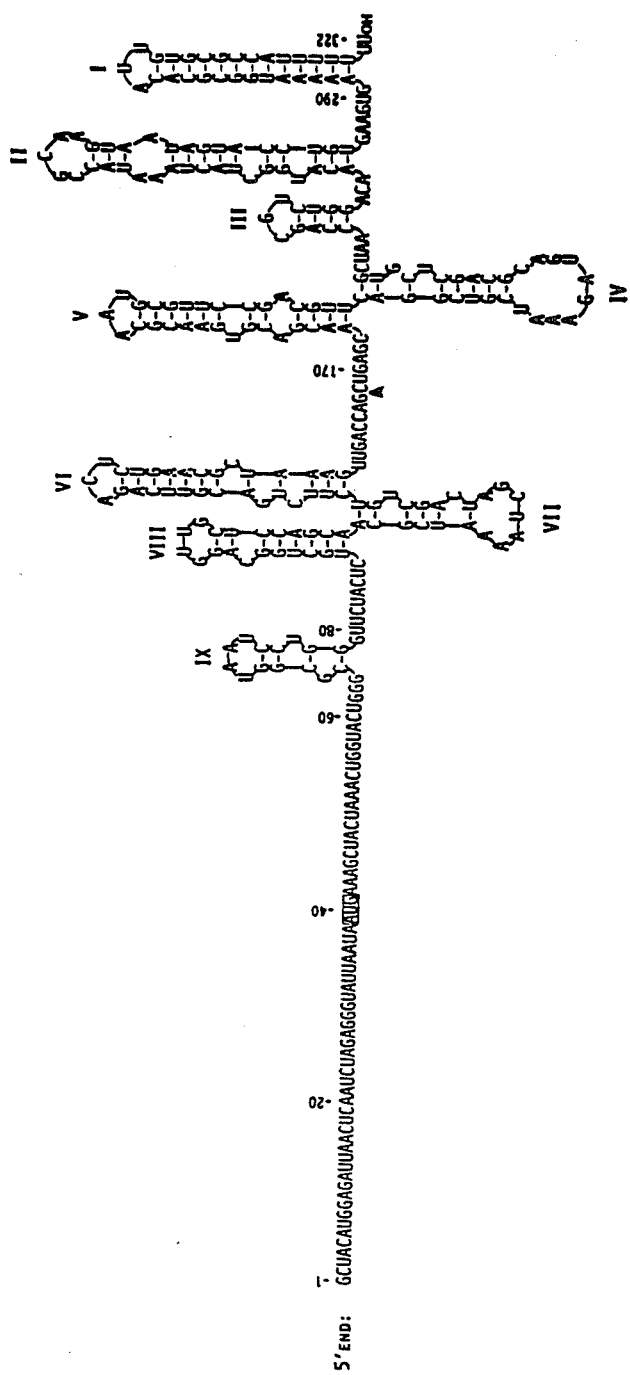
FIG. 3 illustrates the proposed secondary structure of *E. coli* lipoprotein mRNA, in which the translation initiation codon is boxed.

The earlier research of one of the present inventors has shown that as a class, the major outer membrane proteins of gram-negative bacteria are present in rather large quantities in each bacterial cell. For example, it has been found that the *E. coli* lipoprotein, which is one of the most extensively investigated membrane proteins, is also the most abundant protein in the cell in terms of numbers of molecules, there being approximately 700,000–750,000 lipoprotein molecules per cell. Since it has also been shown that there is only one structural gene for the lipoprotein of *E. coli*, extremely efficient machinery for lipoprotein gene expression, at the levels of both transcription and translation, is indicated. It is believed that the lipoprotein gene may be expressed at least ten times more efficiently than genes for ribosomal proteins. The presence of comparable quantities of other major outer membrane proteins in *E. coli*, such as the ompA protein, and the presence of comparable quantities of the major outer membrane proteins in other gram-negative bacteria, such as the lipoprotein of *Serratia marcescens*, indicate that these systems may also have very efficient machinery for gene expression. Thus, while the discussion herein may refer in large part to the lipoprotein system in *E. coli*, it is to be understood that similar results are to be expected from recombinant cloning vehicles which utilize the machinery for gene expression associated with any of the outer membrane protein genes of any gram-negative bacterium.

Although the mechanisms which are responsible for the highly efficient expression of the *E. coli* lipoprotein gene are not yet completely understood, it is believed that several factors must contribute to the abundance of lipoprotein molecules in a bacterial cell. As shown in FIGS. 1A and 1B, the DNA nucleotide sequence of the lipoprotein gene of *E. coli* has been determined, an analysis of which has revealed many unique properties associated with the expression of this gene.

In particular, it has been found that in comparison with other known promoter sequences of *E. coli* genes, the lipoprotein promoter region shows a most striking feature, namely, an extremely high A-T content, which is believed likely to be essential for highly efficient transcription of the lipoprotein gene. The segment of 261 bp preceding the transcription initiation site (from position −261 through position −1 as shown in FIG. 1A) has a very high A-T content of 70%, in contrast with 53% for the transcribed region (or mRNA region) of 322 base pairs (positions +1 to +322), 44% for a segment of 126 bp after the transcription termination site (positions +323 to +449), and 49% for the average A-T content of the *E. coli* chromosome. The A-T content of the segment from position −45 to position −1, within which the nucleotide sequence of the lpp promoter appears to reside, is especially high (80%), and appears to be the highest among the *E. coli* promoter regions thus far sequenced. The A-T richness of the promoter sequence is considered to destabilize the helix structure of the DNA and thereby facilitate the RNA polymerase-mediated strand unwinding necessary for the initiation of transcription.

Apart from its A-T content, the lpp promoter also appears to contain a heptanucleotide sequence at positions −15 through −9 (only eight base pairs distal to the transcription initiation site) which is homologous to the generalized "Pribnow box," as well as dodecanucleotide sequence at positions −38 through −27 which is homologous to the generalized "RNA polymerase recognition site." The homology of these sequences is striking, in that the Pribnow box sequence of the lpp promoter has only one base mismatching with the generalized sequence, while the recognition site sequence shows a mismatch of only 5 out of 12 bases of the generalized sequence. The importance of the specific base sequences at these sites for efficient transcription is well-documented, in that mutants with enhanced promoter efficiency show increased homology of these regions with the generalized sequences.

Further analysis of the DNA sequence of FIGS. 1A and 1B has revealed that besides having an extremely "strong" promoter, the lipoprotein gene also has an oligo-T transcription termination signal, located between positions +316 and +322, which is at least as efficient as all other *E. coli* transcription termination sites that have been studied. It is believed that this factor contributes to the overall efficiency of transcription by hastening the rate of mRNA production, and by limiting the size of the mRNA molecule which is transcribed from the DNA.

As shown in FIG. 2, the complete nucleotide sequence of the *E. coli* lipoprotein mRNA has also been determined, revealing that the mRNA has several unique features in its structure which appear to be important for efficient translation of the mRNA transcript. The mRNA consists of 322 nucleotides, 38 of which are in the 5'-untranslated region and 50 of which are in the 3'-untranslated region, leaving 234 nucleotides in the translated region which code for the lipoprotein precursor, or prolipoprotein. The mRNA sequence of FIG. 2 is complementary to the DNA sequence of FIGS. 1A and 1B, with the exception of the nucleotide at position 313 which is shown as C in FIG. 2 as determined by RNA sequencing, rather than A as determined by the DNA sequencing shown in FIG. 1B. The reason for this difference is not known at present.

The lipoprotein mRNA has been shown to be unusually stable, and it has been proposed that this stability is probably attributable to the formation of extensive secondary structures within the molecule. As shown in FIG. 3, the mRNA can form nine stable "hairpin" stem-and-loop structures (designated by Roman numerals I–IX), the most stable of which (I) is in the 3'-untranslated region. These secondary structures may be responsible for the longer functional half-life which has been observed for the lipoprotein mRNA in comparison with other *E. coli* mRNAs, and may thereby increase the availability of this molecule for ribosomal translation.

Furthermore, although 68% of the total nucleotides in the mRNA molecule are involved in the formation of the hairpin structures shown in FIG. 3, it should be noted that in the first 64 nucleotides from the 5' end there are not stable hairpin structures, whereas between the 65th nucleotide and the 3' end, 85% of the nucleotides are involved in the formation of hairpin structures. This is significant because in the 5'-untranslated region (positions +1 to +38) there appear to be two extensive inverted repeat sequences of nucleotides which are thought to prevent the formation of secondary structures in this region, allowing the ribosome-binding site in this segment to be fully exposed to ribosomes, thereby facilitating the initiation of translation. Moreover, the rate of initiation of translation is probably further facilitated by the presence of two possible ribosome binding sites in this region of the molecule.

Finally, the presence of all three translation termination codons in the 3'-untranslated region of the mRNA (UAA, positions +273 to +275, UAG, positions +276 to +278, and UGA, positions +285 to +287 [see FIG. 2]), all three of which are in the same reading frame as the translatable or "coding" region of the mRNA, provides a unique "back-up" sequence of tandem terminators which probably contributes to the overall efficiency of translation by assuring proper termination of translation in a "fail-safe" manner.

The cumulative effect of these as well as other unique features of the lipoprotein mRNA is believed to result in very efficient translation of this genetic information in *E. coli* cells.

Analogous elaboration processes are believed to be involved in the production of the major outer membrane proteins of all gram-negative bacteria. For example, an analysis and comparison of the DNA sequence of the *Serratia marcescens* ("*S. marcescens*") lipoprotein gene with that of the *E. coli* lpp gene has revealed striking homologies in the promoter region (84%) and in the 5'-untranslated region (95%). Moreover, the A-T content in the promoter region of the *S. marcescens* lipoprotein gene is extremely high (78%), as found in the case of the *E. coli* lipoprotein gene (80%). Furthermore, although the DNA sequence coding for the peptide extension of the prolipoprotein of *S. marcescens* differs somewhat from that of *E. coli*, the resultant alterations in the amino acid sequence do not change the basic properties of the signal peptide as proposed for the *E. coli* prolipoprotein. In addition, the lipoprotein mRNA of *S. marcescens*, as deduced from the DNA sequence, seems capable of forming seven stable hairpin stem-and-loop structures. The existence of the lipoprotein in many different genera of gram-negative bacteria has now been confirmed, and it has been found that the *E. coli* lipoprotein mRNA hybridizes with DNAs from at least the following seven bacterial species (besides *S. marcescens*) in the family Enterobacteriaceae: *Shigella dysenteriae, Salmonella typhimurium, Citrobacter freundii, Klebsiella aerogenes, Enterobacter aerogenes, Edwardsiella tarda*, and *Erwinia amylovora*, thereby confirming a degree of homology of the lipoprotein gene between *E. coli* and other gram-negative bacteria. The expectation that similar properties will be found in recombinant plasmid cloning vehicles utilizing analogous and highly efficient machinery for gene expression derived from any gram-negative bacterium is believed justified by all of these as well as other findings.

In the prior art, the unique characteristics of the biosynthesis and assembly of the outer membrane proteins of gram-negative bacteria, as discussed above, made the lipoprotein genes of these organisms extremely attractive vehicles with which to control the expression of exogenous DNA insert fragments in bacterial transformants. In this application, the structure and function of a modification of such cloning vehicles is described.

2. Strategy For Gene Expression

Figure 4:
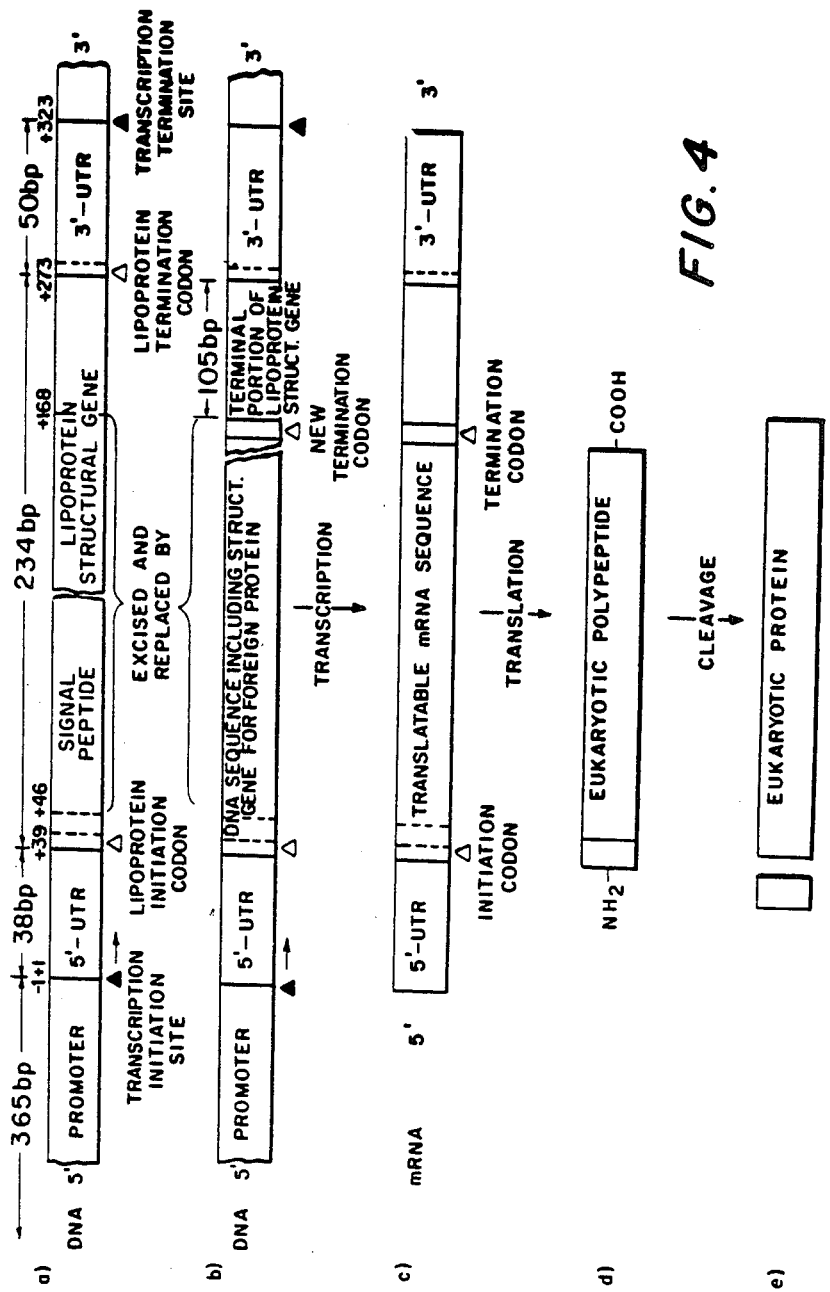
FIG. 4 is a schematic outline of the process by which a eukaryotic protein or other desired polypeptide may be expressed using recombinant plasmid cloning vehicles, in which the transcription initiation and termination sites are indicated by arrows (▲) and the translation initiation and termination sites are indicated by arrows (△)

It will be apparent from the foregoing discussion that a majority of the features which appear to be responsible for the efficient transcription and translation of the lipoprotein gene of *E. coli* reside in the functional fragments of the gene, namely, the promoter, the 5'-untranslated region, the 3'-untranslated region, and the transcription termination site, all of which are located either "upstream" or "downstream" of the lpp structural gene, as shown in FIG. 4, line a. Hence, by inserting a structural gene for a eukaryotic protein or other desired polypeptide in an expression plasmid containing various combinations of the foregoing functional fragments, and by transforming a bacterial host with such a plasmid, the transcription and subsequent translation of the structural gene has been made to take place under the control of those functional fragments.

For reasons which will be evident to those skilled in the art, it is particularly desirable and advantageous to utilize all of the foregoing functional fragments together in tandem in a single expression plasmid. By fusing the structural gene for the desired polypeptide at its 5' end to a DNA sequence comprising both the promoter and the 5'-untranslated region of the *E. coli* lpp gene (most preferably, this DNA sequence also includes the entire 260 bp A-T rich DNA segment preceding the transcription initiation site), highly efficient transcription is achieved by utilizing one of the strongest bacterial promoters, and highly efficient translation is achieved by utilizing a DNA sequence which can code for features which facilitate the initiation of translation, including a very effective ribosome binding site. Moreover, by fusing the structural gene at its 3' end to a DNA sequence comprising the 3'-untranslated region and the transcription termination signal of the *E. coli* lpp gene, the efficiency of transcription is believed to be further enhanced, avoiding transcriptional "read-through" (the synthesis of an unnecessarily long 3'-untranslated region in the mRNA) and more importantly, facilitating the rate of mRNA production. The stability of the mRNA molecule is also augmented by the formation of secondary structure in the 3'-untranslated region.

In the lpp gene expression plasmids of the prior art, the secretory nature of the lipoprotein was utilized to control yet another aspect of the expression of a eukaryotic protein or other desired polypeptide, namely, the location at which the expression product can be expected to be found. Depending upon the site within the lpp gene chosen for insertion of the exogenous DNA, the expression product could be expected to accumulate either within the cytoplasm of the transformant cell, within the periplasmic space, or in the cell's outer membrane.

FIG. 4 schematically illustrates a process wherein a transformant organism expresses a natural eukaryotic protein in accordance with one of the foregoing prior art schemes. In the particular embodiment illustrated in FIG. 4, the structural gene for the eukaryotic protein is inserted within the signal peptide of the lpp gene, several base pairs after the translation initiation codon and downstream of certain functional fragments (namely, the promoter and the 5'-untranslated region) normally associated with the lipoprotein gene. As will be seen by comparing line a with line b in FIG. 4, the orientation of these functional fragments is identical to the natural orientation of these elements in the lipoprotein gene, while the exogenous DNA insert fragment supplants most of the signal peptides as well as a portion of the structural region of the lipoprotein gene.

As shown in FIG. 4, line b, the foreign gene is linked at its 3' end to an extra translation termination codon, which is in turn fused to the remainder of the lipoprotein structural gene. This is linked still further downstream in the normal manner to the 3'-untranslated region of the lpp gene, which ends with the transcription termination site. As can be seen by again comparing line a with line b in FIG. 4, the functional fragments which follow the DNA insert fragment are essentially identical to those which are present normally in the lipoprotein gene.

The 3'-untranslated region derived from the lpp gene codes for an mRNA sequence capable of forming the stem-and-loop structure designated by the numeral I in FIG. 3, which, as discussed previously, is the most stable secondary structure in the lipoprotein mRNA. However, the recombinant DNA sequence depicted schematically in FIG. 4, line b, also includes a terminal portion of the lipoprotein structural gene consisting of 105 base pairs starting with position +168 (this position is designated by the arrow (▲) in FIG. 3). This region is chosen so that the stability of the mRNA transcript can be further enhanced by including four additional stem-and-loop structures (designated by the numerals II, III, IV and V in FIG. 3), without unduly increasing the size of the mRNA molecule produced. However, as set forth below, this region is not ultimately translated.

Transcription of the recombinant DNA sequence illustrated in FIG. 4, line b, yields an mRNA sequence which is illustrated schematically in FIG. 4, line c. It will be seen that this sequence contains the 5'-untranslated region and the 3'-untranslated region, both of which are normally associated with the production of the lipoprotein. However, the mRNA also incorporates a region coding for the eukaryotic protein, preceded by a region which codes for a short segment of the signal peptide of the prolipoprotein, and followed by another region which codes for a segment of the lipoprotein. The latter region ultimately will not be translated, however, due to the insertion of the extra termination codon (designated by an arrow (Δ) in FIG. 4, lines b and c) at the 3' end of the eukaryotic structural gene. Following translation, a polypeptide is produced comprising several extraneous amino acid residues, followed by the amino acid sequence of the desired eukaryotic protein (see FIG. 4, line d). This conjugate expression product can be expected to accumulate within the cytoplasm of the cell, because secretion can not occur in the absence of a complete signal peptide. However, for certain proteins, the expression product can be purified from the cytoplasm in a known manner, and the superfluous protein fragment may then be separated and removed from the natural protein product by known techniques (see FIG. 4, line e), yielding the desired polypeptide which may then be stored for future use.

Alternatively, the DNA sequence coding for the extraneous amino acids can be excised from the expression plasmid in a known manner prior to transformation of the bacterial host, such that the expression product corresponds exactly with the desired foreign protein and may be purified by known techniques.

In an alternative embodiment of the foregoing prior art scheme, the same functional fragments are used, but the DNA sequence coding for the desired polypeptide is inserted further downstream, following the last codon of the signal peptide (i.e., at or near the signal peptide cleavage site). It will be apparent to those skilled in the art that in this embodiment, the orientation of the functional fragments is once again identical to the natural orientation of these elements in the lipoprotein gene, allowing full advantage to be taken of the efficiencies of transcription and translation associated therewith, including the enhanced stability of the mRNA transcript attributable to the incorporation of four additional stem-and-loop structures, as described hereinabove.

The transcription and ultimate translation of such a recombinant DNA sequence proceeds in a manner analogous to that described hereinabove and illustrated in FIG. 4, except that following translation, a polypeptide is produced comprising a signal peptide corresponding to the signal peptide of the prolipoprotein, followed by the amino acid sequence of the desired eukaryotic protein. This precursor product can then be secreted across the cytoplasmic membrane under the control of the lpp signal peptide, in the process of which the peptide extension itself may possibly be recognized and removed by enzymatic action natural to the E. coli transformant cell (although this is unlikely to happen for most proteins for the reasons discussed more fully hereinabove), yielding a product consisting of the natural eukaryotic protein, perhaps with several extraneous amino acid residues at the amino terminus which can be removed as discussed hereinabove. This product accumulates initially in the periplasmic space, and whether or not the signal peptide has been removed, the product may ultimately pass through the cell's outer membrane and into the culture medium provided that certain E. coli transformant strains are used, as set forth in more detail hereinbelow.

Using this approach, the stability of the expression product can be enhanced, since protease activity is considered to be reduced in the periplasmic space as compared with the cytoplasm. Another advantage of using a secretion vector is that the amino terminal amino acid residue of the secreted expression product can in general be identical to that of the natural gene product (as a result of cleavage of the signal peptide by a signal peptidase), whereas a gene product produced in the cytoplasm without a peptide extension must generally commence with a methionine residue at its amino terminus, corresponding to the translation initiation codon, ATG. In addition, a secretion strategy is imperative when the desired expression product is a toxic enzyme or protein (such as a nuclease or protease), the production of which in the cytoplasm might be lethal to the cell. Furthermore, the presence of the signal peptide may even protect the foreign protein from possible degradative action inside the cell, which could otherwise lower the protein yield and could also cause contamination of the foreign protein by heterogenous degradative products, resulting in purification difficulties. While the prior art has provided an acceptable overall strategy for secretion of an exogenous gene product, and has demonstrated its workability to some degree, the prior art lpp gene secretion vectors themselves are not satisfactory for the production of most proteins in this manner, because of the cell's inability to cleave the lpp signal peptide in a reliable fashion as described in more detail hereinabove.

In yet another alternative embodiment of the foregoing prior art scheme, the same functional fragments are again used, but the DNA sequence coding for the desired polypeptide is inserted still further downstream, for example, following the codon for the eighth amino acid residue after the signal peptide cleavage site. It will be apparent to those skilled in the art that in this embodiment, the orientation of the functional fragments is once again identical to the natural orientation of these elements in the lipoprotein gene, allowing full advantage to be taken of the efficiencies of transcription and translation associated therewith, including the enhanced stability of the mRNA transcript attributable to the incorporation of four additional stem-and-loop structures, as described hereinabove.

The transcription and ultimate translation of such a recombinant DNA sequence proceeds in a manner analogous to that described hereinabove and illustrated in FIG. 4, except that following translation, a polypeptide is produced comprising a signal peptide of 20 amino acid residues, corresponding to the signal peptide of the prolipoprotein, followed by eight amino acid residues corresponding to the first eight amino acid residues of the mature lipoprotein (including the amino terminal cysteine residue), followed by the amino acid sequence of the desired eukaryotic protein. As with the embodiment previously described, this precursor product may be translocated naturally across the cytoplasmic membrane, but in contrast to the previous embodiment, the lpp signal peptide can be recognized and removed. However, the product may not accumulate in the periplasmic space; instead, because the amino terminus of the mature lipoprotein can undergo the usual lipid modification by processes native to the transformant, the expression product may then be processed further and inserted into the outer membrane of the cell in a manner analogous to the normal insertion of the lipoprotein into the outer membrane. If, as expected only the first eight amino acid residues of the expression product (corresponding to the lipoprotein) are actually bound into the outer membrane, then the remainder of the expression product, consisting of the amino acid sequence of the eukaryotic protein or other desired polypeptide, will protrude from the outer membrane, such that, for certain proteins, the membrane may be isolated and the desired protein purified from the membrane easily.

It will therefore be evident to those skilled in the art that by constructing a plasmid cloning vehicle according to the prior art with one or another of the three insertion sites described above, and by using such a plasmid to express an exogenous gene product, the location of that express an exogenous gene product, the location of that product can be predicted with a reasonable degree of certainty, and the appropriate methods for isolating and purifying that product will thereby be suggested. The choice of insertion site will often be dictated by the identity and structure of the desired polypeptide itself, especially if the method of purification most appropriate for that product is known. However, the present invention relates only to a modification of those lpp gene expression plasmids in which the insertion site immediately follows the last codon of the signal peptide, providing an improved sub-class of secretion plasmids with which the disadvantages of the prior art may be overcome, as discussed more fully hereinabove and hereinbelow.

In order to facilitate still further the expression of a wide variety of exogenous DNA fragments using the lpp cloning vehicles described above, the prior art also provided a short polynucleotide sequence containing the recognition sites for the Eco RI, Hind III and Bam HI restriction enzymes to be incorporated at the insertion site in each plasmid. This allows additional flexibility, in that six different types of restriction fragments can be inserted into each plasmid according to the straight-forward and well-known techniques described hereinabove. Thus, DNA insert fragments tailored to have any one of the following pairs of cohesive termini can be readily used with the prior art, as well as with the present invention: Eco RI-Eco RI, Hind III-Hind III, Bam HI-Bam HI, Eco RI-Hind III, Eco RI-Bam HI and Hind III-Bam HI.

As mentioned hereinabove, the expression of genetic information is termed inducible if transcription cannot be initiated in the absence of a certain molecule. Inducible gene expression is exemplified in nature by the *E. coli* lac promoter-operator, which controls the production of β-galactosidase, an important enzyme in lactose digestion. Normally, the expression of this gene is "switched off" by the presence of a lactose repressor, which binds to the lac promoter-operator, preventing interaction between RNA polymerase and the promoter sequence and thereby inhibiting transcription (and subsequent translation) of the β-galactosidase structural gene. In the presence of lactose, however, the repressor molecule is removed from the DNA and the gene is "switched on," allowing transcription to proceed until a sufficient quantity of the β-galactosidase enzyme is produced to digest the lactose, after which the repressor again "switches off" the gene.

The constitutive lpp gene cloning vehicles described hereinabove have been made inducible by inserting the lac promoter-operator downstream of the lpp promoter, but upstream of the exogenous DNA insert fragment. The lac promoter-operator region is carried on a 95 bp DNA fragment derived from the natural *E. coli* lacZ gene. In this configuration, transcription of the foreign DNA from either promoter is blocked by the repressor molecule and cannot proceed in the absence of a substance, termed a "lactose inducer," which for present purposes is a molecule that reacts with and alters the lactose repressor molecule such that the repressor molecule can no longer bind to the lac promoter-operator. When induced with lactose or with a synthetic inducer such as isopropyl-β-D-thiogalactoside (hereinafter "IPTG"), the foreign DNA can be transcribed from both the lpp and lac promoters independently, allowing approximately five to ten times higher gene expression than would occur using the lac promoter alone.

The inducible lpp gene cloning vehicles described above have, in turn, been modified for auto-regulation by inserting within each plasmid a functional *E. coli* lacI gene. In this manner, the 1:1 ratio between lactose repressor genes and lac promoters, which is normally present in wild-type *E. coli* cells, can be maintained in transformants chosen for expression of the desired polypeptide. Accordingly, such transformants need not carry and need not be provided with the F-prime factor previously thought necessary, but found to be unsatisfactory to repress the expression of the desired product by microorganisms transformed with the inducible (but not auto-regulated) expression plasmids described hereinabove.

The inducible and auto-regulated inducible lpp gene cloning vehicles previously constructed which utilize a lac promoter-operator fragment consisting of 95 bp (corresponding to the DNA segment lying between position −59 and position +36 of the natural lacZ gene, plus an additional 8 bp attributable to linker molecules which are added to facilitate insertion of the fragment into the expression plasmid, for a total fragment length of 103 bp), have also been modified to incorporate a different DNA fragment as the source of the lac promoter-operator. The latter fragment consists of 105 bp, corresponding to the DNA segment lying between position −40 and position +65 of the lacZ gene, plus the same additional 8 bp derived from the linker molecules which are used to tailor the fragment for easy insertion into the expression plasmid, for a total fragment length of 113 bp. The latter fragment, which incorporates 19 fewer bp upstream of the promoter-operator region than the 95 bp fragment, but also includes 29 additional bp downstream of the promoter-operator region, will be referred to generally herein as the "113 bp lac promoter-operator fragment" or simply the "113 bp lac fragment." It has been determined that an unexpected increase of up to 100% in expression of the desired product can be obtained if the 113 bp lac fragment is used. The reasons for the differences in activity between the 95 bp lac fragment and the 113 bp lac fragment are not known at present.

As mentioned hereinabove, the present invention relates to an improvement of the foregoing scheme in which the DNA sequence coding for the ompA signal peptide is utilized to direct the secretion of the desired gene product across the cytoplasmic membrane. It is to be understood, however, that all of the desirable features described hereinabove in connection with the auto-regulated inducible lpp gene expression plasmids constructed previously may be incorporated with equal advantage in the secretion plasmids of the present invention. These include the efficiencies of transcription and translation usually associated with the four specified functional fragments of the lpp gene, the enhanced stability of the mRNA transcript attributable to the incorporation of the four additional stem-and-loop structures normally associated with the mRNA transcript of the terminal portion of the lipoprotein structural gene, and the incorporation of Eco RI, Hind III and Bam HI restriction enzyme recognition sequences at the exogenous DNA insertion site in each plasmid to facilitate the expression of a wide variety of DNA insert fragments.

It is to be understood also that virtually any structural gene coding for a desired polypeptide, including mammalian and human hormones, enzymes and immunogenic proteins (or intermediates therefor), may be expressed using the recombinant plasmids of the present invention, provided that the natural gene product is normally secreted. Examples of such proteins include insulin, interferon and growth hormone, but the invention is not confined to these exemplary products.

3. The Transformant

In the preferred embodiment of the present invention, the auto-regulated inducible recombinant cloning vehicles utilizing the 113 bp lac promoter-operator fragment the the DNA sequence coding for the ompA signal peptide, and incorporating the gene for the desired eukaryotic protein or other polypeptide, are used to transform particular *E. coli* strains as hosts for cloning and for subsequent production of the protein. The host cell strains used will be chosen to have a "deletion mutant" in the lpp gene, so that the host cells cannot produce the lipoprotein. The use of a deletion mutant strain as the transformant is thought to stimulate the production of a large amount of the foreign protein, since the entire capacity of the host cells to produce the lipoprotein is thereby channelled towards production of the foreign protein. Furthermore, secretion of the foreign protein across the cytoplasmic membrane is facilitated in lpp-defective host cells, since the secretion sites in the membrane which are intended to be used for lipoprotein secretion are instead available for secretion of the foreign protein, even though that secretion is directed by the ompA signal peptide.

The use of the lpp-defective cells is especially beneficial for use with secretion vectors such as those of the present invention, wherein the gene coding for the foreign protein is inserted at or near a signal peptide cleavage site. This is because such cells are known to be "leaky", i.e., proteins secreted across the cytoplasmic membrane of such cells ultimately "leak" out into the culture medium through the outer membrane of the cell. This is believed to be desirable not only because release of the desired foreign protein into the culture medium may in some cases allow easier isolation and purification of the foreign protein than would be possible if the foreign protein remained inside the cell, but also because the foreign protein would otherwise accumulate in the periplasmic space, perhaps leading to undesirable interference with normal cellular activities of cell growth. Secretion of the desired eukaryotic gene product outside the cell may also avoid degradation of that product into smaller fragments by proteolitic enzymes which are normally present within the cell.

4. Experimental

The strategy and techniques described hereinabove were applied experimentally to construct recombinant bacterial plasmid cloning vehicles according to the present invention. For completeness and continuity, the specific experimental steps used to construct the lpp gene expression plasmids resulting from the previous research of the present inventors are repeated herein in full, followed by the experimental steps used to construct the secretion plasmids of the present invention, and then followed by a description of the exemplary results obtained when one of those secretion plasmids was used to produce a particular protein.

In the prior research, three types or "families" of vehicles were contemplated, one for constitutive gene expression (labelled the "pIN-I" type), a second for inducible gene expression (the "pIN-II" type), and a third for auto-regulated inducible gene expression (the "pIN-III" type). The pIN-II and pIN-III types utilize both the 95 bp lac promoter-operator fragment and the 113 bp lac fragment discussed hereinabove, these being hereinafter referred to collectively as the "pIN-II(113)" and "pIN-III(113)" types or series, respectively.

Figure 5:
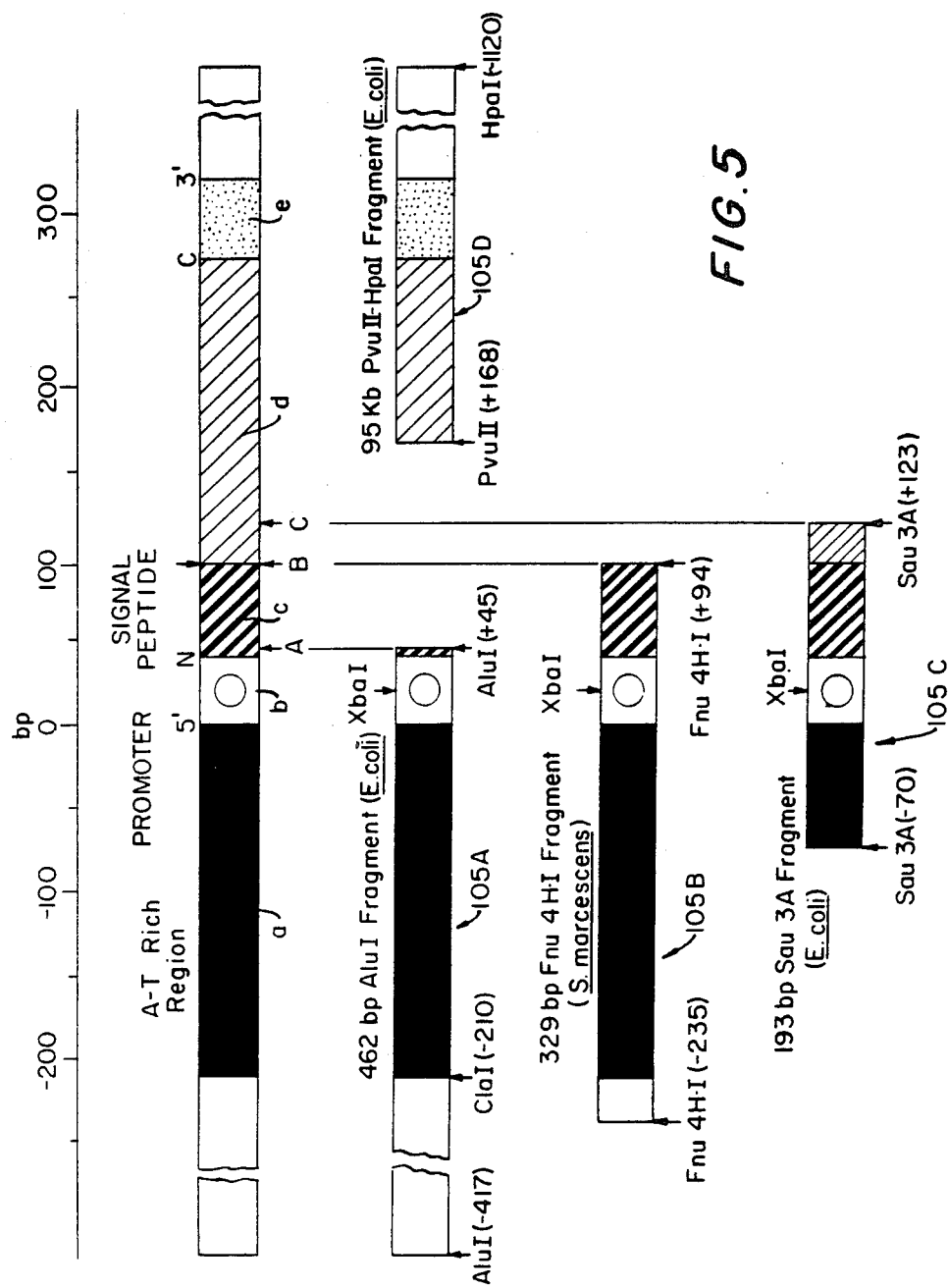

In the portion of this application repeating the experimental work done previously, the insertion site located within the DNA sequence coding for the prolipoprotein signal peptide will be designated the "A" site, while the insertion site located immediately after the last codon of the signal peptide will be labelled the "B" site, and the insertion site located after the codon for the eighth amino acid residue of the mature lipoprotein will be referred to as the "C" site (see FIG. 5). For each site, three prior art plasmids can be prepared (one corresponding to each of the three possible reading frames), yielding a total of nine expression plasmids in each series which are labelled A-1, A-2, A-3, B-1, B-2, B3, and C-1, C-2, C-3.

The restriction enzymes used herein were obtained from New England Biolabs and Bethesda Research Laboratories. T4 DNA ligase was obtained from Bethesda Research Laboratories (unless otherwise indicated), and S1 Nuclease was obtained from Miles Laboratories.

A. Construction of A Site Plasmids (pIN-I)

FIGS. 6–15 schematically depict the manner in which constitutive recombinant plasmids incorporating the A insertion site were constructed, and may be referred to in connection with the following more particularized discussion.

1. Construction of Plasmid pKEN111

The first step in the construction of the A site lpp gene cloning vehicles was to construct a plasmid to serve as a source of lpp gene components in subsequent steps of the procedure. The plasmid chosen to receive the E. coli lpp gene for this purpose was pSC101, a small (molecular wt. approximately 5.8 megadaltons) plasmid carrying a gene conferring resistance to the antibiotic tetracycline (Tc) (Cohen, S. N., et al. J. Bacteriol. 132: 734–737 [1977]). As shown at 100 in FIG. 6, pSC101 includes a cleavage site for the restriction endonuclease Eco RI located at the 5' end of the tetracycline resistance gene. The plasmid pSC101 was obtained from Dr. E. Ohtsubo at the Department of Microbiology, State University of New York at Stony Brook.

As shown schematically at 101 in FIG. 6, 2 micrograms of plasmid pSC101 DNA were digested to completion with two units of the restriction endonuclease Eco RI in 50 microliters of a reaction mixture comprising 100 mM Tris:HCl (pH 7.5), 75 mM NaCl, 6 mM $MgCl_2$, 6 mM β-mercaptoethanol and 100 micrograms/ml bovine serum albumin (hereinafter "BSA") (this reaction mixture will hereinafter be referred to as an "Eco RI buffer") at 37° C. for 60 minutes. To prevent self-ligation of the Eco RI-treated pSC101 DNA, bacterial alkaline phosphatase (hereinafter "BAP") was added (0.1 units of Worthington BAPF), and incubation was continued for 60 minutes at 37° C. The reaction was terminated by phenol extraction, and the linearized DNAs were recovered by ethanol precipitation.

Figure 6:
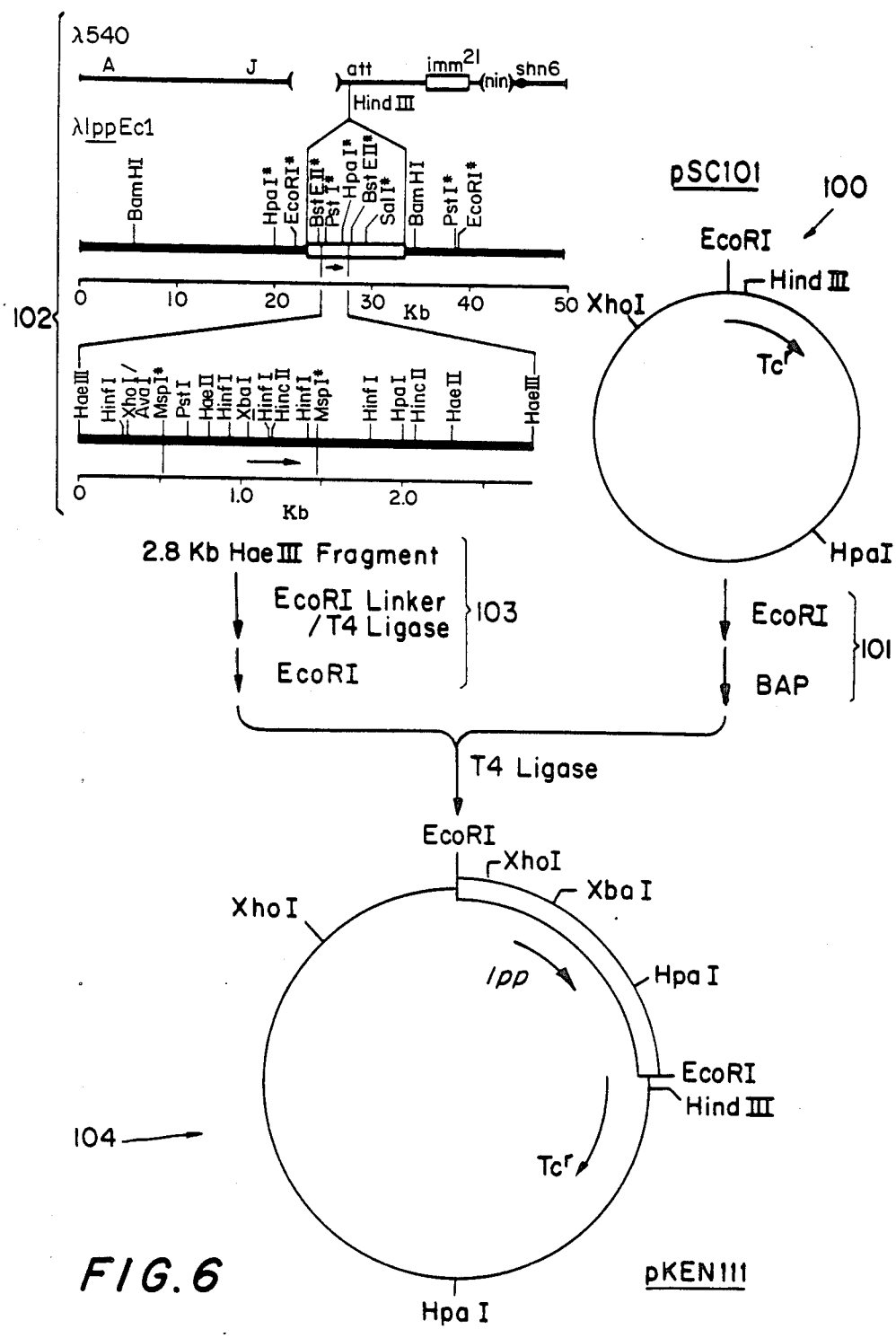

A 2.8 kilobase ("Kb") DNA fragment containing the E. coli lpp gene was separately derived, as shown at 102 in FIG. 6, from a hybrid λ phage carrying the E. coli lpp gene (designated λlppEc-1). The lpp gene had previously been cloned into a λ phage vector, λ540 (Murray and Murray, J. Mol. Biol. 98: 551–564 [1975]), as follows: Total DNA (200 micrograms) isolated from an E. coli K-12 strain merodiploid for the lpp gene (JE5519/F506 [Movva, N. R., et al., J. Bacteriol. 133: 81–84 (1978)]) was digested with 200 units of the restriction enzyme Hind III. DNA fragments were separated on a preparative agarose gel, and fractions of DNA fragments of approximately 10 Kb which showed positive hybridization with 5'-$^{32}$P-lipoprotein mRNA were collected, using the Southern hybridization technique (J. Mol. Biol. 98: 503–517). A mixture of 10 Kb Hind III fragments (enriched approximately twenty-fold) and Hind III-cleaved λ540 vector DNA was reacted with T4 DNA ligase. Ligated DNA was used to transfect E. coli K802, NRRL B-15016 (obtained from Dr. F. R. Blattner at the Laboratory of Genetics, University of Wisconsin-Madison). This strain is available to the public from the permanent collection of the Northern Regional Research Laboratory, U.S. Department of Agriculture, Peoria, Illinois, U.S.A. Recombinant phages carrying the lpp gene were screened by the plaque hybridization technique of Benton and Davis (Science 196: 180–182 [1977]) using 5'-$^{32}$P-lipoprotein mRNA. One of the plaques examined which gave positive hybridization was found to carry a fully functional lpp gene, and was designated λlppEc-1.

Two hundred micrograms of λlppEc-1 DNA were then digested completely with 200 units of the restriction enzyme Hae III in 500 microliters of a reaction mixture containing 6 mM Tris:HCl (pH 7.5), 6 mM MgCl$_2$, 6 mM NaCl, 6 mM β-mercaptoethanol and 100 micrograms/ml BSA (the foregoing reaction mixture will hereinafter be referred to as a "Hae III buffer") at 37° C. for 2 hours, and the 2.8 Kb Hae III fragment carrying the *E. coli* lpp gene was purified by fractionation on a 5% polyacrylamide gel according to the following procedure: The reaction mixture was first extracted with phenol, and the DNA fragments were then precipitated with 2.5 volumes of ethanol, dried under vacuum, dissolved in 200 microliters of a buffer comprising 5% glycerol, 20 mM EDTA, 0.05% bromophenol blue and 0.05% xylen cyanol (this mixture will hereinafter be referred to as a "gel buffer") and thereafter fractionated on a 5% polyacrylamide gel. The DNA band which had migrated to a 2.8 Kb position was excised from the gel, and the DNA fragments were eluted from the gel by electrophoresis. Ethidium bromide dye, used to locate the DNA band in the gel, was removed from the DNA fragments by phenol extraction. The DNA fragments were precipitated with 2.5 volumes of ethanol, centrifuged, dissolved in 200 microliters of 0.3M Na-acetate, re-precipitated with 0.5 ml of ethanol and dried again under vacuum. Approximately 10 micrograms of a purified 2.8 Kb Hae III fragment were recovered.

In order to clone the 2.8 Kb Hae III fragment into pSC101, synthetic "Eco RI linker" molecules were attached to the termini of the 2.8 Kb Hae III fragment, as shown schematically at 103 in FIG. 6. The Eco RI linker (5'GGAATTCC3'; obtained from Collaborative Research) was phosphorylated by T4 polynucleotide kinase (obtained from P. L. Biochemicals) with ATP in 50 microliters of a reaction mixture containing 3 moles of the linker, 66 mM Tris:HCl (pH 7.5), 10 mM MgCl$_2$, 10 mM β-mercaptoethanol, 60 μM ATP and 10 units of T4 polynucleotide kinase. After the mixture was incubated at 37° C. for 30 minutes, it was heated at 60° C. for 10 minutes, and cooled to 37° C. Five microliters of 0.1M β-mercaptoethanol and 10 units of T4 polynucleotide kinase were added to the mixture, and the reaction was continued at 37° C. for 30 minutes. The reaction was terminated by freezing the mixture in a dry ice-ethanol bath.

The 2.8 Kb Hae III fragment (2 micrograms) was mixed with 150 pmoles of phosphorylated Eco RI linker and was treated with 4 units of T4 DNA ligase in 12.5 microliters of a reaction mixture containing 66 mM Tris:HCl (pH 7.5), 10 mM MgCl$_2$, 10 mM dithiothreitol (the foregoing reaction mixture will hereinafter be referred to as a "ligase buffer") and 0.6 mM ATP at 12.5° C. for 15 hours. The reaction was terminated by diluting the mixture twenty-fold with Eco RI buffer and by heating the mixture at 60° C. for 10 minutes. Thirty units of the restriction enzyme Eco RI were added, and the mixture was incubated at 37° C. for one hour to create Eco RI cohesive termini. The reaction was terminated by heating at 60° C. for 10 minutes.

The mixture thus obtained was added to 2 micrograms of the previously-linearized plasmid pSC101 DNA, and phenol extraction was performed. After extraction with ether, the DNAs were precipitated with ethanol, dried under vacuum, and dissolved in 100 microliters of ligase buffer. The mixture was heated at 37° C. for 5 minutes, and the Eco RI cohesive termini were annealed by incubating at 4° C. for 16 hours and then at 0° C. for one hour. After adding ATP (0.4 mM final) and 1 unit of T4 DNA ligase, the mixture was incubated at 12.5° C. for 7 hours.

One-fourth of the ligation mixture was thereafter used to transform *E. coli* lpp deletion mutant strain JE5527, NRRL B-15012, (F$^-$, man, lpp-2, pps, thi, his, rpsL, gyrA, recA1 [Hirota, Y., et al., *Proc. Natl. Acad. Sci. U.S.A.* 74: 1417–1420 (1977)], obtained from Dr. Y. Hirota, National Institute of Genetics, Mishima, Japan). This strain is available to the public from the permanent collection of the Northern Regional Research Laboratory, U.S. Department of Agriculture, Peoria, Ill., U.S.A. Transformation was carried out as described in Cohen, S.N., et al., *Proc. Natl. Acad. Sci. U.S.A.* 69: 2110–2114 (1972), and tetracycline-resistant transformants were grown overnight on Whatman 3MM filter papers, placed on the surface of an L broth plate containing 10 micrograms/ml of tetracycline, and screened for lpp clones by colony hybridization (Gergen, J. P., et al., *Nucleic Acids Res.* 7: 2115–2136 [1979]). A 0.95 Kb Msp I fragment of λlppEc-1 containing the lpp gene was nick-translated with [α-$^{32}$P]dATP and [α-$^{32}$P]dCTP, as described in Maniatis, T., et al., *Proc. Natl. Acad. Sci. U.S.A.* 72: 1184–1188 (1975), and was used as a $^{32}$P-probe. One of the transformants which gave positive hybridization was shown to contain the plasmid with the structure illustrated at 104 in FIG. 6, and this plasmid was designated pKEN111. This plasmid is obtainable from *E. coli* CC620/pKEN111, NRRL B-15011, which is available to the public from the permanent collection of the Northern Regional Research Laboratory, U.S. Department of Agriculture, Peoria, Ill., U.S.A. The plasmid can be obtained from NRRL B-15011 by conventional means.

2. Construction Of Plasmid pKEN008

Figure 7:
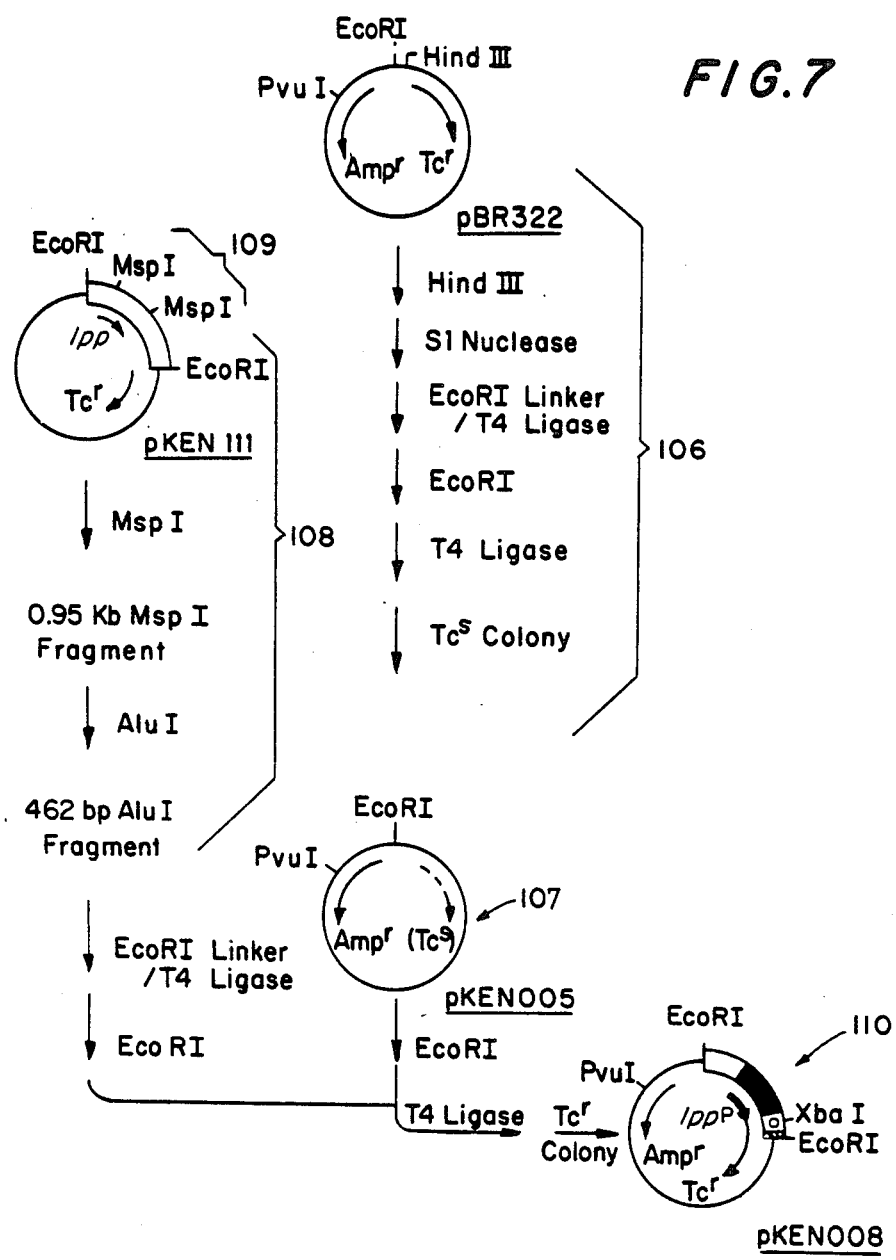

The parental plasmid chosen for construction of the lpp gene expression plasmids of the present invention was pBR322 (molecular wt. approximately 2.6 megadaltons), carrying genes conferring resistance to the antibiotics ampicillin (Amp) and tetracycline (Tc) (Bolivar, F., et al., *Gene* 2: 95–113 [1977]). As shown in FIG. 7, pBR322 includes an Eco RI cleavage site located at the 5' end of the tetracycline resistance gene, as well as a Hind III cleavage site located within the promoter of the tetracycline resistance gene and a Pvu I cleavage site located within the ampicillin resistance gene. The plasmid pBR322 was obtained from Dr. N. Arnheim of the Department of Biochemistry, State University of New York at Stony Brook, and is available commercially from Bethesda Research Laboratories.

FIG. 5 illustrates schematically the various components of the lpp gene, each of which is identified by a symbol or shading. Specifically, the shaded segment indicated by the letter "a" identifies the A-T rich region of approximately 260 base pairs preceding the transcription initiation site and containing the lpp promoter. The 5'-untranslated region is identified by the segment containing the circular device and marked with the letter "b". The signal peptide region of the prolipoprotein is identified by the diagonally hatched and shaded segment "c". The structural region of the lpp gene is identified by the diagonally hatched segment labelled with the letter "d", while the speckled segment "e" identifies the 3'-untranslated region and the transcription termination site. These symbols and shading are used in a like manner to identify the same functional fragments of the lpp gene in FIGS. 7–11, 15, 17–18, 21–23, and 26–33.

FIG. 7 illustrates the strategy used for inserting a fragment carrying the promoter and the 5'-untranslated region of the lpp gene into pBR322. The fragment chosen for this purpose was a 462 bp Alu I fragment of pKEN111 which, as shown schematically at 105A in FIG. 5, contains not only the promoter sequence and the 5'-untranslated region (positions −45 to −1 and +1 to +39, respectively) of the lpp gene, but also the entire extremely A-T rich segment preceding the promoter sequence.

In order to clone the 462 bp Alu I fragment containing the lpp promoter region in pBR322, the DNA fragment lying between the Eco RI and Hind III cleavage sites of pBR322 (containing the promoter of the tetracycline resistance gene) was first delected, as shown schematically at 106 in FIG. 7, using the following procedure: 11 micrograms of pBR322 plasmid DNA were digested with 11 units of Hind III restriction endonuclease in 200 microliters of a reaction mixture comprising 10 mM Tris:HCl (pH 7.5), 10 mM $MgCl_2$, 60 mM NaCl, 6 mM β-mercaptoethanol and 100 micrograms/ml BSA (this reaction mixture will hereinafter bet referred to as a "Hind III buffer") at 37° C. for one hour. After digestion was completed, phenol extraction was performed, and DNAs were recovered by ethanol precipitation.

To remove the Hind III cohesive termini, the DNA was treated with 1.5 microliters of S1 Nuclease (Miles Laboratories) in a final volume of 300 microliters of a buffer containing 30 mM Na-acetate (pH 4.25), 0.3M NaCl and 4 mM $ZnSO_4$ (hereinafter referred to as an "S1 buffer") at 20° C. for one hour. The reaction was terminated by adding 30 microliters 500 mM Tris:HCl (pH 8.0) and 30 microliters 250 mM EDTA, following which phenol extraction was performed. To remove phenol, the mixture was extracted with ether and dialyzed against 0.01×SSC (SSC=0.15M NaCl+0.015M Na-citrate) at 4° C. overnight, and the DNAs were recovered by ethanol precipitation.

Phosphorylated Eco RI linker (200 pmoles) was then added and the mixture was treated with 4 units of T4 DNA ligase in 12.5 microliters of ligase buffer containing 0.6 mM ATP at 12.5° C. for 16 hours. Eco RI cohesive termini were created by addition of 30 units of Eco RI restriction enzyme in 75 microliters of Eco RI buffer at 37° C. for 2 hours. The reaction was terminated by phenol extraction and the DNAs were recovered by ethanol precipitation.

Eco RI cohesive terminal were ligated and the plasmid was thereby re-circularized by treatment with 0.3 units of T4 DNA ligase in 20 microliters of ligase buffer containing 0.4 mM ATP at 12.5° C. for 7 hours. A 0.5 microgram aliquot of the ligated DNA was used to transform *E. coli* strain JE5519, NRRL B-15013 (F−, aroD, man, argE, lac, gal, rpsL, gyrA, recAl; obtained from Dr. Y. Hirota, National Institute of Genetics, Mishima, Japan). This strain is available to the public from the permanent collection of the Northern Regional Research Laboratory, U.S. Department of Agriculture, Peoria, Ill., U.S.A. Ten of the ampicillin-resistant, tetracycline-sensitive transformants were grown overnight in one ml of L broth containing 50 micrograms/ml of ampicillin. Plasmid DNAs were isolated from 0.5 ml of the cultures by the rapid alkaline-denaturation method described by Birnboim, H. C. and Doly, J., *Nucleic Acids Res.* 7: 1513 (1979), and analyzed by restriction enzyme mapping. One of the plasmids had the structure shown at 107 in FIG. 7, and was designated pKEN005.

As shown schematically at 108 in FIG. 7, the 462 bp Alu I fragment containing the lpp promoter was derived as follows: 100 micrograms of pKEN111 plasmid DNA were digested with Msp I restriction enzyme in 600 microliters of a buffer containing 10 mM Tris:HCl (pH 7.5), 10 mM $MgCl_2$, 6 mM KCl, 1 mM dithiothreitol, and 100 micrograms/ml BSA (this mixture will hereinafter be referred to as an "Hpa I buffer") at 37° C. for 3 hours. (Although pKEN111 contains numerous Msp I cleavage sites, only the two of interest are illustrated at 109 in FIG. 7.) Following extraction with phenol, the DNA fragments were precipitated with 2.5 volumes of ethanol, dried under vacuum, dissolved in 100 microliters of gel buffer, and fractionated on a 5% polyacrylamide gel. Approximately 6 micrograms of a purified 0.95 Kb Msp I fragment were recovered after elution of the separated DNA fragments from the gel. The purified 0.95 Kb Msp I fragment was subsequently digested with Alu I restriction endonuclease in 400 microliters of Hind III buffer at 37° C. for 2 hours, yielding a 462 bp Alu I fragment which was purified by gel electrophoresis.

One microgram of the 462 bp Alu I fragment was then mixed with 150 pmoles of phosphorylated Eco RI linker and treated with 4 units of T4 DNA ligase in 10 microliters of ligase buffer containing 0.6 mM ATP at 12.5° C. for 16 hours. The ligated DNA was digested with 40 units of Eco RI restriction enzyme in 100 microliters of Eco RI buffer at 37° C. for one hour to create Eco RI cohesive termini. The digestion was terminated by heating the mixture at 60° C. for 10 minutes, and 0.6 micrograms of Eco RI-digested pKEN005 plasmid DNA added to the mixture and phenol extraction was performed. The DNAs were recovered by ethanol precipitation, and the Eco RI cohesive termini were joined by treating with 0.4 units of T4 DNA ligase in 20 microliters of ligase buffer containing 0.4 mM ATP at 12.5° C. for 7 hours. Ligated DNAs were used to transform *E. coli* strain JE5519, NRRL B-15013, and transformants were selected for tetracycline resistance on an L broth plate containing 12.5 micrograms/ml of tetracycline. Analysis of the plasmid DNAs isolated from the tetracycline-resistant transformants by the rapid alkaline-denaturation method showed insertion of the 462 bp Alu I fragment at the Eco RI site of pKEN005 as depicted at 110 in FIG. 7, and one of the plasmids thus obtained was designated pKEN008.

3. Construction of Plasmid pKEN010

Figure 8:
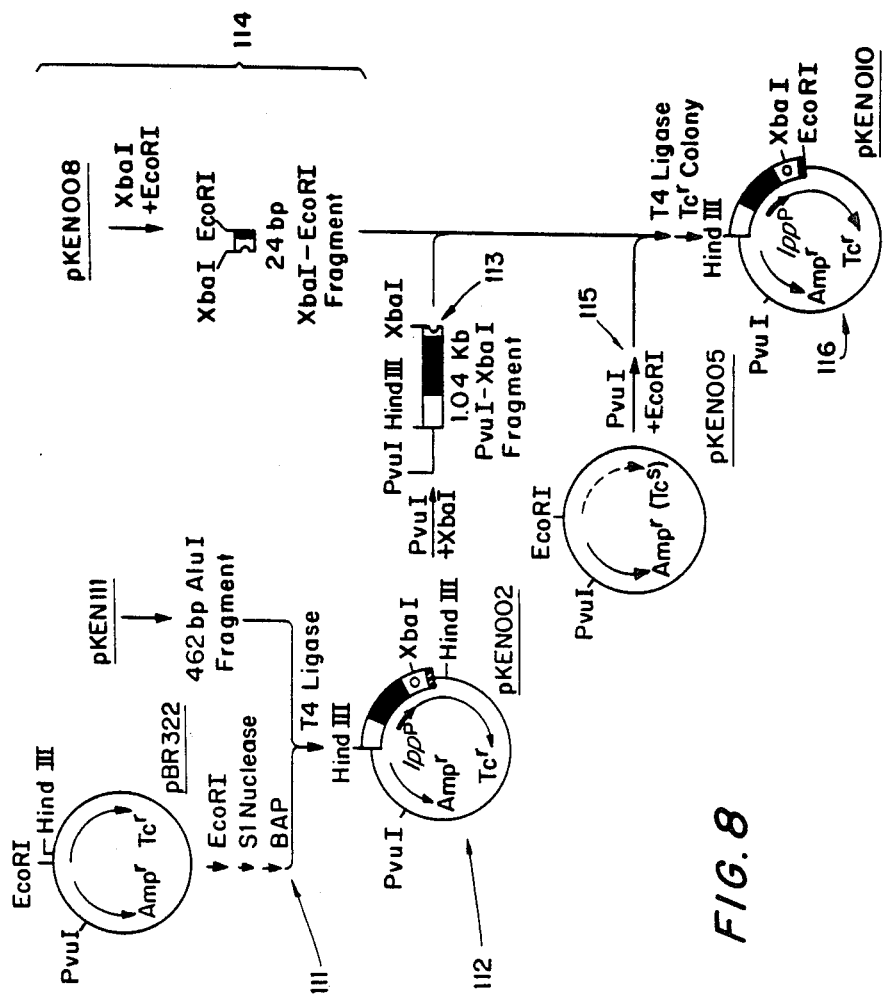

The next step in the construction of the A site lpp gene cloning vehicles was to eliminate one of the two Eco RI cleavage sites of pKEN008. This was necessary in order to insure that the only insertion point available for the oxogenous gene chosen for cloning would be immediately downstream of the 462 bp Alu I fragment (now an Eco RI fragment) containing the lpp gene promoter and 5'-untranslated region. FIG. 8 illustrates schematically the strategy for removing the Eco RI site distal to the lpp gene promoter.

In order to accomplish this result, the following procedure was used: 4 micrograms of Eco RI-digested pBR322 plasmid DNA were treated first with S1 Nuclease to remove the Eco RI cohesive termini, and then with BAP to prevent self-ligation. As shown schematically at 111 in FIG. 8, the DNAs were then mixed with 0.76 micrograms of the purified 462 bp Alu I fragment (derived from pKEN111 as described above in connection with FIG. 7), and blunt-end ligated with 2.4 units of T4 DNA ligase in 10 microliters of ligase buffer containing 0.6 mM ATP at 12.5° C. for 16 hours. One-half of the ligated DNA was used to transform *E. coli* strain JE5519, NRRL B-15013, and one of the transformants was shown to contain the plasmid with the structure illustrated at 112 in FIG. 8. This plasmid was designated pKEN002, and after digestion of 25 micrograms of pKEN002 plasmid DNA with Pvu I and Xba I restriction enzymes in 500 microliters of a buffer comprising 6 mM Tris:HCl (pH 7.9), 6 mM MgCl₂, 150 mM NaCl, 6 mM β-mercapto-ethanol and 100 micrograms/ml BSA (the foregoing mixture will hereinafter be referred to as a "Bam HI buffer") at 37° C. for one hour, a 1.04 Kb Pvu I-Xba I DNA fragment (illustrated at 113 in FIG. 8) was purified by gel electrophoresis.

As shown schematically at 114 in FIG. 8, a 24 bp Xba I-Eco RI DNA fragment was derived from pKEN008 as follows: 25 micrograms of pKEN008 plasmid DNA was digested with Eco RI restriction enzyme, and a 470 bp Eco RI fragment was purified by gel electrophoresis. One microgram of the 470 bp Eco RI fragment was then digested with Xba I restriction enzyme, and was mixed with one microgram of the 1.04 Kb Pvu I-Xba I DNA fragment obtained previously, as well as with 0.75 micrograms of pKEN005 plasmid DNA previously digested with Pvu I and Eco RI restriction enzymes (as shown at 115 in FIG. 8). The DNA mixture was treated with 0.8 units of T4 DNA ligase in 50 microliters of ligase buffer containing 0.4 mM ATP at 12.5° C. for 7 hours. One-half of the ligated DNA was used to transform *E. coli* strain JE5519, NRRL B-15013, and transformants were selected for tetracycline resistance. Analysis of the plasmid DNAs obtained from 0.5 ml cultures of tetracycline-resistant transformants by the rapid alkalinedenaturation method, indicated that one of the plasmids had the structure shown at 116 in FIG. 8. This plasmid was designated pKEN010.

4. Construction Of Plasmid pKEN018

Figure 9:
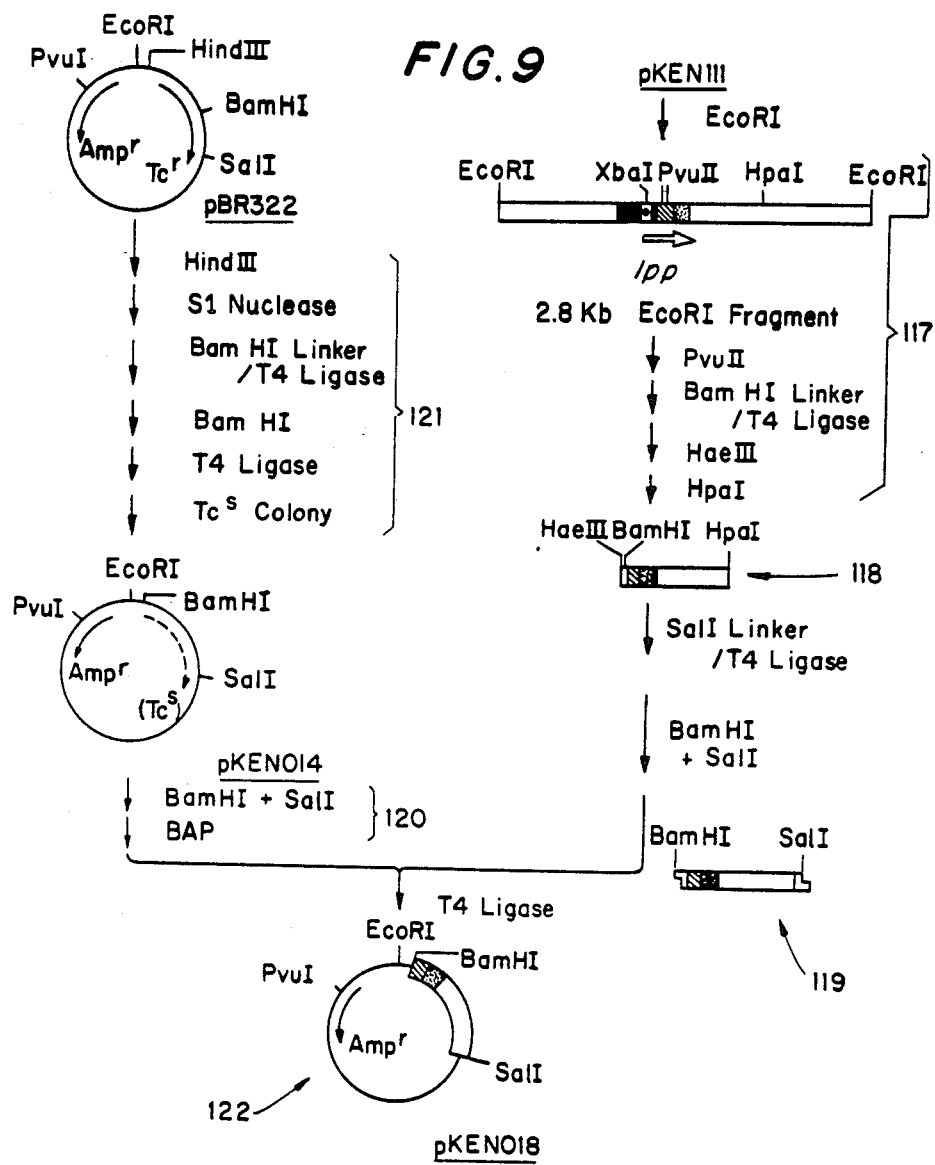

FIG. 9 illustrates the strategy used for cloning a DNA fragment carrying the 3'-untranslated region and the transcription termination site of the lpp gene. The fragment chosen for this purpose was a 0.95 Kb Pvu II-Hpa I fragment of pKEN111, shown schematically at 105D in FIG. 5. Since the Pvu II restriction enzyme cleaves the lpp gene sequence between positions +167 and +168, this fragment contains approximately the latter half of the lpp gene (see FIGS. 1 and 5). In order to insert this fragment into the cloning vehicle in the same orientation as the promoter fragment, Bam HI linker and Sal I linker were attached to the Pvu II and Hpa I cleavage sites, respectively.

As shown schematically at 117 in FIG. 9, a 2.8 Kb Eco RI fragment was obtained from pKEN111 plasmid DNA by digestion with Eco RI restriction enzyme and fractionation on a polyacrylamide gel, and 10 micrograms of this purified fragment were digested completely with Pvu II restriction endonuclease in 500 microliters of Hae III buffer at 37° C. for one hour. The reaction was terminated by phenol extraction, and the mixture was extracted with ether. The DNA fragments were precipitated with 2.5 volumes of ethanol, centrifuged, re-dissolved in 200 microliters of 0.3M Na-acetate and re-precipitated with 0.5 ml of ethanol. Five micrograms of the Pvu II-digested 2.8 Kb Eco RI fragment were mixed with 390 pmoles of phosphorylated Bam HI linker and blunt-end ligated with 6 units of T4 DNA ligase in 25 microliters of ligase buffer containing 0.6 mM ATP at 12.5° C. for 16 hours. The reaction mixture was diluted to 150 microliters with Hae III buffer and heated at 60° C. for 10 minutes to inactivate the T4 DNA ligase. After the addition of 60 units of Hae III restriction enzyme, the mixture was incubated at 37° C. for one hour.

Since the Bam HI linker used here (obtained from Collaborative Research and phosphorylated in the same manner as described previously in connection with the Eco RI linker) has the base sequence 5'CCGGATCCGG3', the recognition sequence for the restriction enzyme Hae III

was created at the junction of any two linker fragments. Thus, the use of Hae III restriction enzyme as set forth above to digest the Bam HI linker-ligated Pvu II fragments (which fragments do not contain any internal Hae III cleavage sites) effected the removal of superfluous multiple Bam HI linker fragments joined to the Pvu II terminus, leaving only one such linker fragment directly joined to that terminus. This procedure greatly simplified the purification of the DNA fragment containing the 3' end of the lpp gene, as described below.

After inactivation of the Hae III enzyme by heating the reaction mixture at 60° C. for 10 minutes, the DNA fragments were digested completely with Hpa I restriction enzyme in 400 microliters of Hpa I buffer at 37° C. for 2 hours. The reaction mixture was extracted with phenol and the DNA fragments were precipitated with ethanol, dried under vacuum, dissolved in 100 microliters of gel buffer and fractionated on a 5% polyacrylamide gel. The DNA band which had migrated to a 0.95 Kb position was excised from the gel, and the DNA fragments were eluted from the gel by electrophoresis. After removal of ethidium bromide dye by phenol extraction, the DNA fragments were precipitated with 2.5 volumes of ethanol, centrifuged, dissolved in 200 microliters of 0.3M Na-acetate, re-precipitated with 0.5 ml of ethanol and again dried under vacuum. Approximately one microgram of a purified 0.95 Kb Hae III-Hpa I fragment (illustrated at 118 in FIG. 9) was recovered.

One hundred and twenty pmoles of phosphorylated Sal I linker (5'GGTCGACC3'; obtained from Collaborative Research and phosphorylated according to the same procedure as described hereinabove) were mixed with 0.75 micrograms of the purified 0.95 Kb Hae III-Hpa I fragment, and blunt-end ligated with 3.5 units of T4 DNA ligase in 25 microliters of ligase buffer containing 0.6 mM ATP at 12.5° C. for 16 hours. The reaction mixture was diluted with sufficient Bam HI buffer to make a final volume of 300 microliters and was then heated at 60° C. for 10 minutes. Sufficient amounts of Bam HI and Sal I restriction enzymes were added and the mixture was incubated at 37° C. for 2 hours to create cohesive termini by cleaving the Bam HI and Sal I linkers attached to the Pvu II and Hpa I termini, respectively, resulting in a 0.95 Kb Bam HI-Sal I fragment (illustrated at 119 in FIG. 9). The restriction endonuclease digestion was terminated by heating at 60° C. for 10 minutes.

At this stage, half the volume of the mixture (150 microliters), containing approximately 0.38 micrograms of the 0.95 Kb Bam HI-Sal I fragment, was mixed with one microgram of pKEN014 plasmid DNA, which had previously been digested with Bam HI and Sal I restriction enzymes and treated with BAP (as shown schematically at 120 in FIG. 9). Plasmid pKEN014 had been previously derived from pBR322 by deleting a 346 bp Hind III-Bam HI fragment (containing most of the tetracycline resistance gene) from pBR322. This fragment was removed in order to keep the size of the expression plasmids to a minimum (approximately 5 Kb). The deletion of this fragment was accomplished, as shown schematically at 121 in FIG. 9, by Hind III digestion, followed by S1 Nuclease treatment for one hour at 20° C., Bam HI linker attachment, Bam HI complete digestion, re-circularization by T4 DNA ligase, and selection of tetracycline-sensitive transformants.

The mixture of linearized pKEN014 plasmid DNA and 0.95 Kb Bam HI-Sal I fragments was extracted with phenol, and the DNAs were precipitated with 2.5 volumes of ethanol, centrifuged and dissolved in 200 microliters of 0.3M Na-acetate. The DNAs were re-precipitated with 0.5 ml of ethanol, centrifuged and dried under vacuum. Cohesive termini of the DNA fragments were annealed with 0.4 units of T4 DNA ligase in 60 microliters of ligase buffer containing 0.4 mM ATP at 12.5° C. for 7 hours. Twelve microliters of the ligated mixture were then used to transform *E. coli* strain JE5519, NRRL B-15013, and twelve of the ampicillin-resistant transformants were grown overnight in one ml of L broth containing 50 micrograms/ml of ampicillin. Plasmid DNAs were isolated from 0.5 ml of the cultures by the rapid alkaline-denaturation method and analyzed by agarose gel electrophoresis. Five of the plasmid DNAs were found to carry the 0.95 Kb Bam HI-Sal I fragment, and one of these plasmids was designated pKEN018. DNA sequencing of the pKEN018 plasmid DNA indicated the structure shown at 122 in FIG. 9, and specifically showed that the Bam HI linker was attached at the Pvu II site within the lpp gene at the correct position.

5. Construction Of Plasmid pKEN021

The next step in the construction of the A site lpp gene cloning vehicles was to combine the lpp promoter fragment with the transcription terminator fragment in the same orientation. This step was carried out by replacing a 630 bp Pvu I-Eco RI fragment of pKEN018 with a 1.1 Kb Pvu I-Eco RI fragment of pKEN010, as illustrated schematically in FIG. 10.

In order to accomplish this result, 20 micrograms of pKEN010 plasmid DNA were digested to completion (as shown at 123 in FIG. 10) with Pvu I restriction endonuclease in 100 microliters of Bam HI buffer at 37° C. for 1.5 hours. After inactivating the Pvu I enzyme by heating the reaction mixture at 60° C. for 10 minutes, 52 microliters of water, 40 microliters of 0.5M Tris:HCl (pH 7.5), 4 microliters of 0.1M MgCl$_2$ and 40 units of Eco RI restriction enzyme were added. The reaction mixture was incubated at 37° C. for one hour and the digestion was terminated by phenol extraction. The DNA fragments were precipitated with 2.5 volumes of ethanol, dried under vacuum, dissolved in 100 microliters of gel buffer, and fractionated on a 5% polyacrylamide gel. Four micrograms of a purified 1.1 Kb Pvu I-Eco RI fragment were obtained after elution of the separated DNA fragments from the gel.

Figure 10:
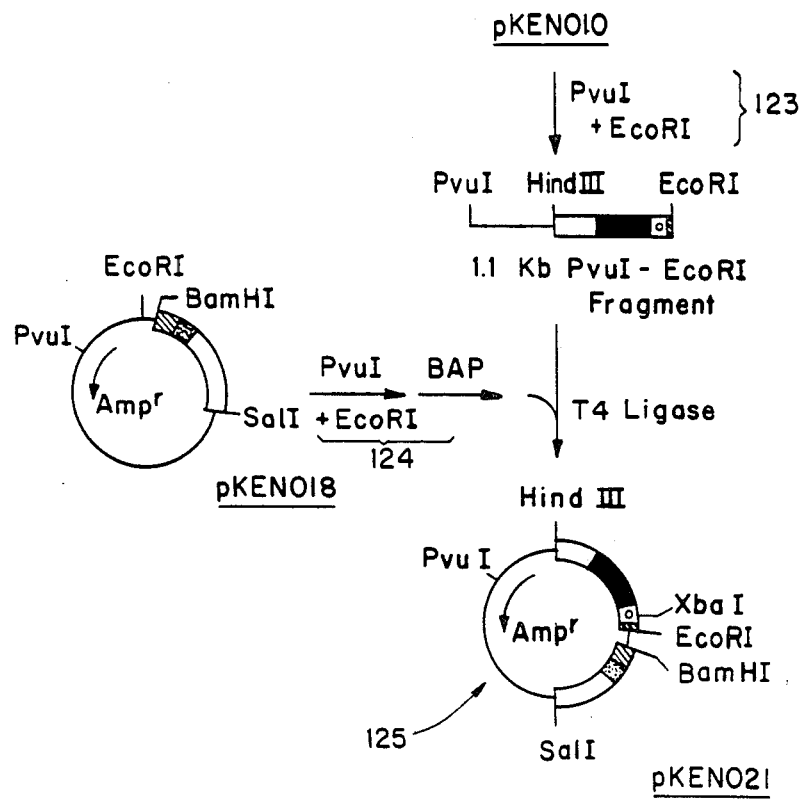

The purified fragment (0.75 micrograms) was then mixed with 0.6 micrograms of pKEN018 plasmid DNA which had previously been double-digested with Pvu I and Eco RI restriction enzymes and then treated with BAP (as shown at 124 in FIG. 10). The Pvu I and the Eco RI cohesive termini were ligated by treating with 0.4 units of T4 DNA ligase in 50 microliters of ligase buffer containing 0.4 mM ATP at 12.5° C. for 7 hours. Twenty-five microliters of the ligated mixture were used to transform *E. coli* strain JE5519, NRRL B-15013, and transformants were selected for ampicillin resistance. Plasmid DNAs were isolated from ampicillin-resistant transformants and analyzed by agarose gel electrophoresis. Restriction enzyme mapping indicated that one of the plasmids had the structure shown at 125 in FIG. 10, and this plasmid was designated pKEN021.

6. Construction Of Plasmid pKEN037

Figure 11:
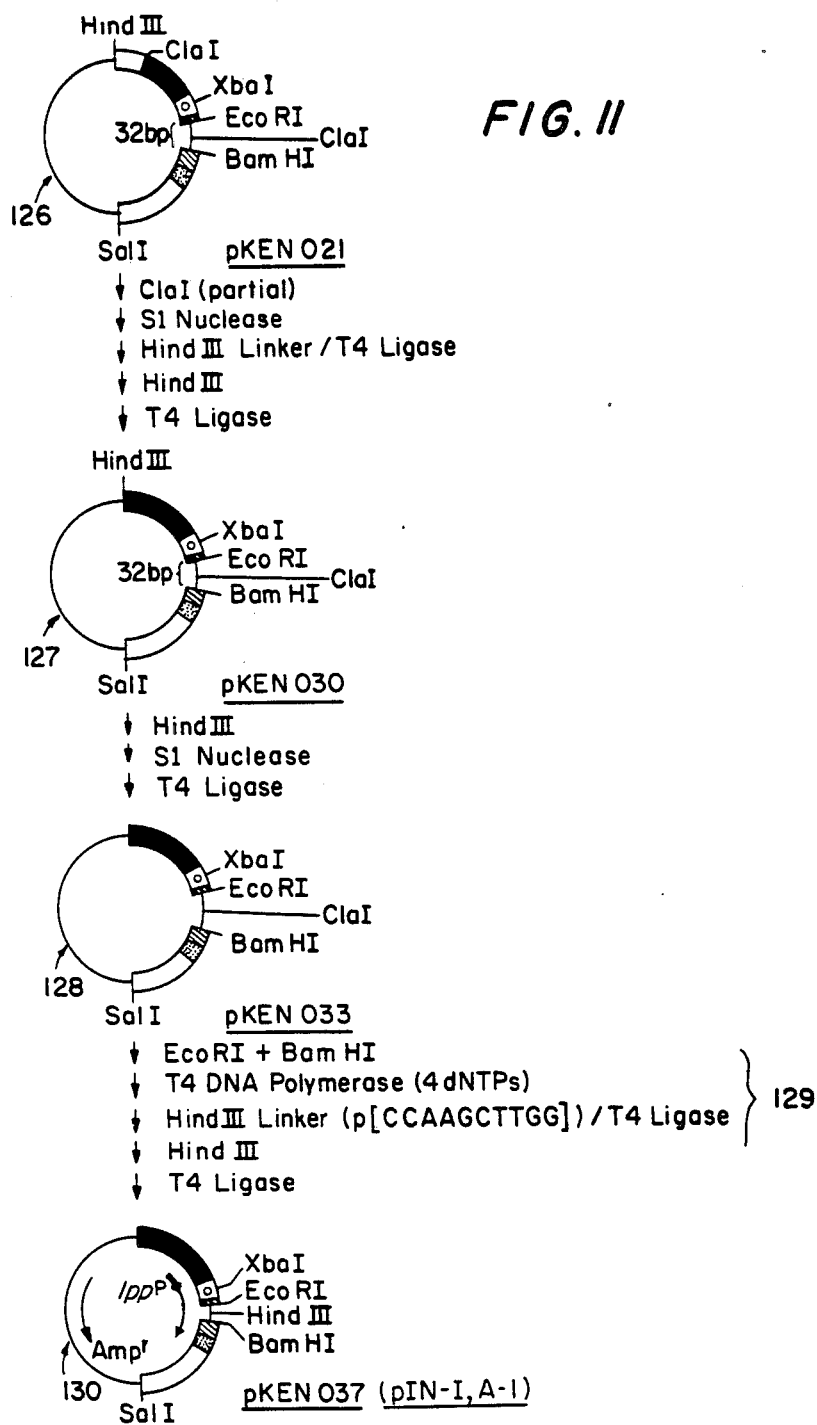

FIG. 11 illustrates the final step in the construction of the first A site lpp gene expression plasmid. As shown at 126 in FIG. 11, pKEN021 carries both the lpp promoter fragment and the lpp transcription terminator fragment, separated by a 32 bp fragment derived from pBR322. By deleting the latter fragment and inserting a DNA sequence coding for a desired polypeptide, a functional moiety for expression of the desired polypeptide is provided. However, since there are Eco RI and Bam HI cleavage sites at the ends of the 32 bp fragment, the structure of plasmid pKEN021 allows only for the insertion of exogenous DNA insert fragments having Eco RI-Eco RI, Bam HI-Bam HI, or Eco RI-Bam HI cohesive termini. Therefore, in order to expand the class of exogenous genes which can be inserted to include those tailored with other combinations of cohesive termini, the DNA sequence in this region was modified to add a Hind III cleavage site between the existing Eco RI and Bam HI sites.

To accomplish this result, it was first desirable to reduce the size of the plasmid by eliminating the 200 bp Hind III-Cla I fragment in pKEN021, using the following procedure: five micrograms of pKEN021 plasmid DNA were partially digested with one unit of Cla I restriction enzyme in 100 microliters of a reaction mixture comprising 10 mM Tris:HCl (pH 8.0), 10 mM MgCl$_2$ and 100 micrograms/ml BSA at 37° C. for one hour. After phenol extraction and ethanol precipitation, Cla I cohesive termini were removed by treating with 600 units of S1 Nuclease in 200 microliters of S1 buffer at 20° C. for one hour. The reaction was terminated by adding 20 microliters of 0.5M Tris:HCl (pH 8.0) and 20 microliters of 0.25M EDTA. The mixture was extracted with phenol and dialyzed for four hours against 0.01×SSC. The DNAs were precipitated with 2.5 volumes of ethanol, centrifuged and re-suspended in 100 microliters of 0.3M Na-acetate. The DNAs were re-precipitated with 250 microliters of ethanol, centrifuged, and dried under vacuum.

One microgram of the S1-treated DNA was then mixed with 70 pmoles of phosphorylated Hind III linker (5'CCAAGCTTGG3'; obtained from Collaborative Research and phosphorylated according to the same procedure as described hereinabove) and blunt-end ligated with 4 units of T4 DNA ligase in 20 microliters of ligase buffer containing 0.6 mM ATP at 12.5° C. for 16 hours. The mixture was then diluted to 100 microliters with Hind III buffer and heated at 60° C. for 10 minutes. Twenty units of Hind III restriction endonuclease were added, and the mixture was incubated at 37° C. for one hour to remove superfluous linker molecules and to create Hind III cohesive termini. The reaction mixture was then extracted with phenol, and the DNAs were precipitated with ethanol. Plasmid DNAs (0.5 micrograms) were re-circularized by treating with 0.8 units of T4 DNA ligase in 15 microliters of ligase buffer containing 0.4 mM ATP at 12.5° C. for 7 hours. Eight microliters of the ligated mixture were used to transform *E. coli* strain JA221, NRRL B-15014 (recA—, hr—, hm+, ΔtrpE5, thr, leu, thi, lacY—; obtained from Dr. J. Carbon, Dept. of Biological Sciences, University of California, Santa Barbara). This strain is available to the public from the permanent collection of the Northern Regional Research Laboratory, U.S. Department of Agriculture, Peoria, Ill., U.S.A. Among the plasmid DNAs which were purified from the ampicillin-resistant transformants was one that had the structure shown at 127 in FIG. 11, and this plasmid was designated pKEN030.

In order to eliminate the Hind III cleavage site of pKEN030, 2.5 micrograms of pKEN030 plasmid DNA were digested with 5 units of Hind III restriction enzyme in 50 microliters of Hind III buffer at 37° C. for one hour. After phenol extraction and ethanol precipitation, the Hind III cohesive termini were removed by treating with 400 units of S1 nuclease in 200 microliters of S1 buffer at 20° C. for one hour. Following recovery of the DNA, 0.75 micrograms of the S1-treated plasmid DNAs were re-circularized by treating with 2 units of T4 DNA ligase in 10 microliters of ligase buffer containing 0.6 mM ATP at 12.5° C. for 16 hours. Three microliters of the ligated mixture were then used to transform *E. coli* strain JA221, NRRL B-15014, and one of the plasmids isolated from the ampicillin-resistant transformants was found to have the structure shown at 128 in FIG. 11. This plasmid, designated pKEN033, contained no Hind III cleavage sites.

Figure 12:
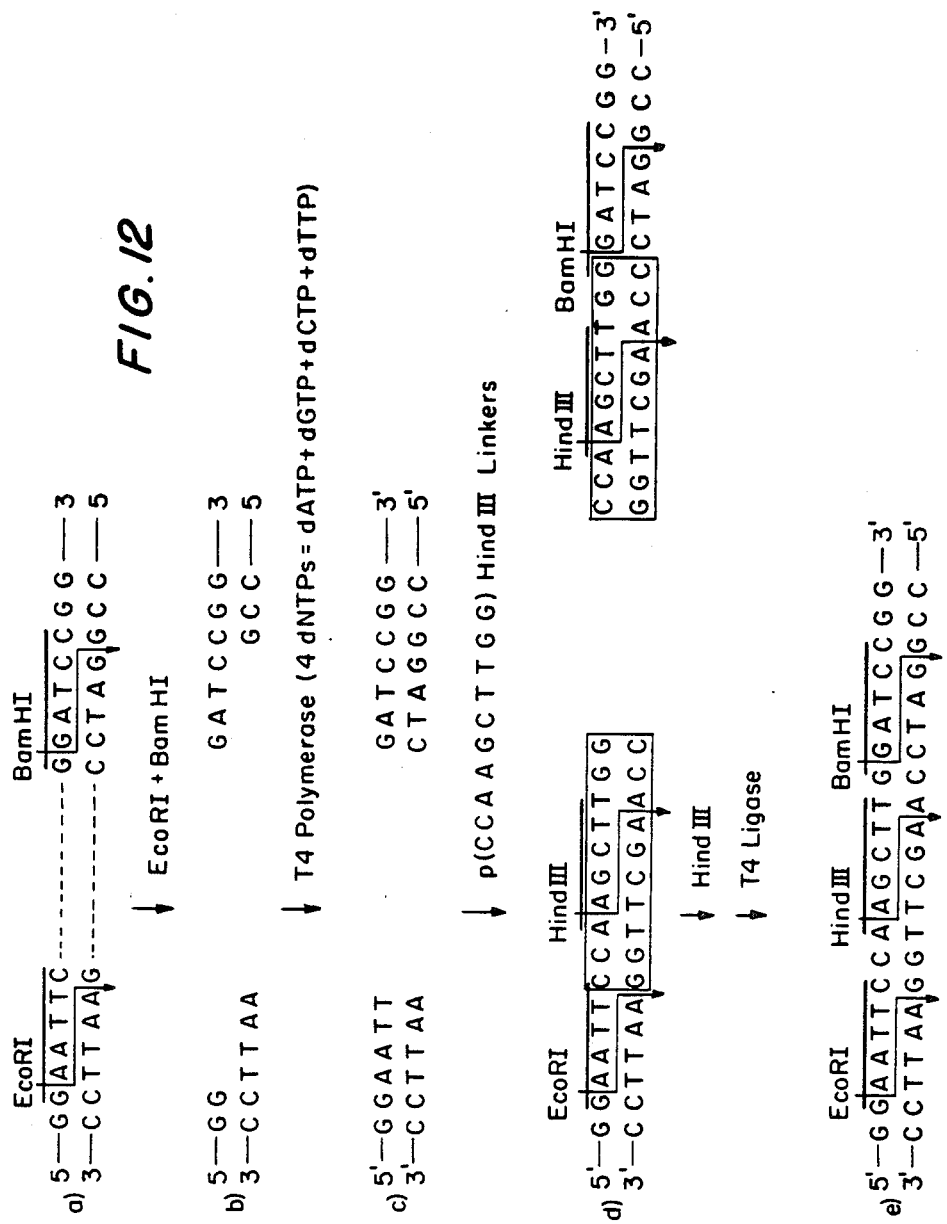
Figure 14:
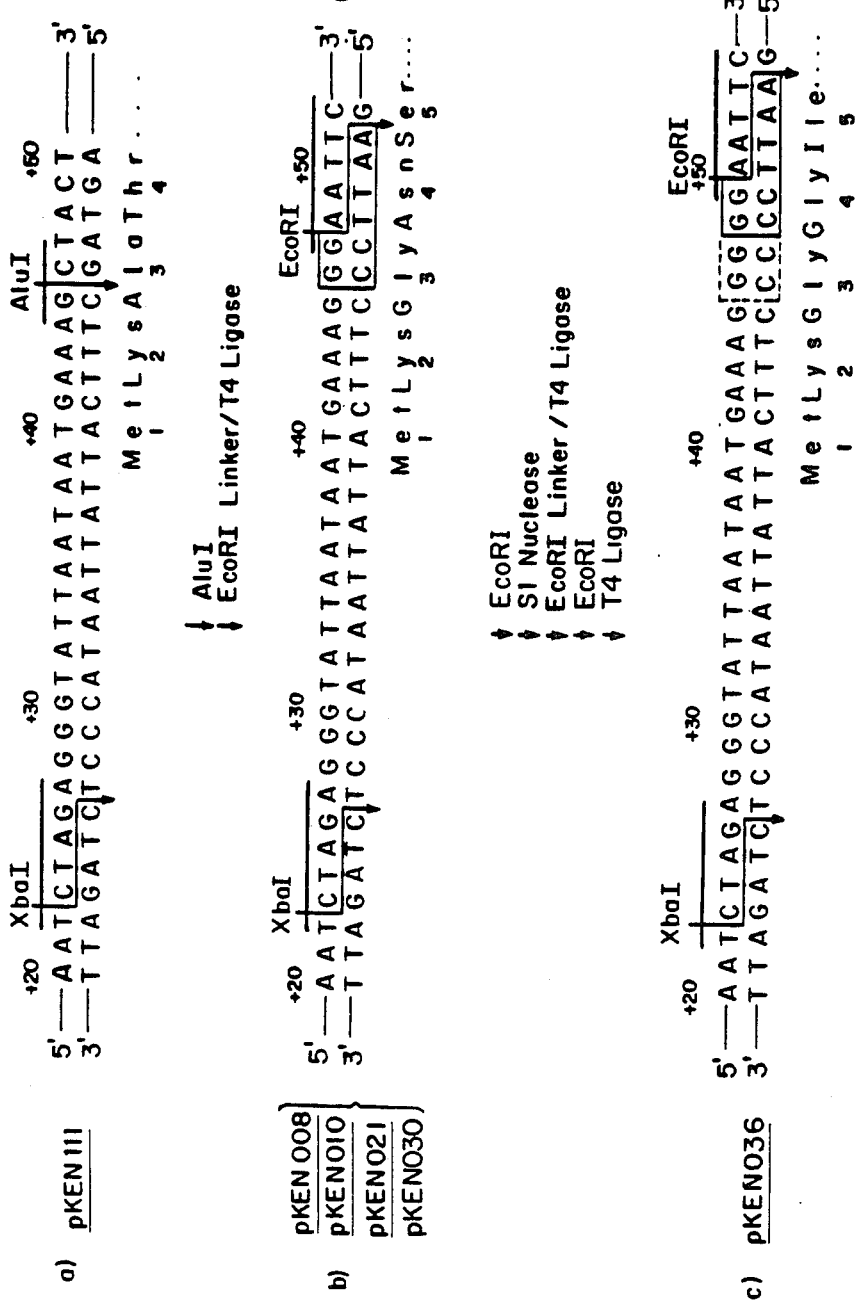

As shown schematically at 129 in FIG. 11, and in more detail in FIG. 12, the DNA sequence of plasmid pKEN033 was modified to create a Hind III cleavage site between the Eco RI and Bam HI sites, as follows: 5 micrograms of pKEN033 plasmid DNA (having the DNA sequence of interest shown in FIG. 12, line a) were digested with 10 units of Bam HI restriction endonuclease in 50 microliters of Bam HI buffer at 37° C. for one hour. After inactivation of the Bam HI enzyme by heating the reaction mixture at 60° C. for 10 minutes, the linearized DNA fragments were further digested with 10 units of Eco RI enzyme in 100 microliters of Eco RI buffer at 37° C. for one hour (see FIG. 12, line b). After phenol extraction and ethanol precipitation, the DNAs (3.6 micrograms) were treated with three units of T4 DNA polymerase (obtained from Bethesda Research Laboratories) in 20 microliters of a reaction mixture containing 50 mM Tris:HCl (pH 8.0), 100 mM KCl, 6 mM $MgCl_2$, and 6 mM dithiothreitol (this reaction mixture will hereinafter be referred to as a "polymerase buffer") in the presence of 0.1 mM each of dATP, dGTP, dCTP and dTTP at 12.5° C. for 45 minutes. By this procedure, the Bam HI and the Eco RI "sticky ends" were filled in completely, as shown in FIG. 12, line c.

After recovery of the DNAs, 300 pmoles of phosphorylated Hind III linker were added, followed by blunt-end ligation with 4 units of T4 DNA ligase in 15 microliters of ligase buffer containing 0.6 mM ATP at 12.5° C. for 16 hours. The mixture was then diluted to 100 microliters with Hind III buffer, and digested with 100 units of Hind III restriction enzyme. The mixture was incubated at 37° C. for one hour to remove superfluous linker molecules and to create Hind III cohesive termini (see FIG. 12, line d), which were later joined (thereby re-circularizing the plasmid DNAs) by treating 0.8 micrograms of the DNA with 0.4 units of T4 DNA ligase in 20 microliters of ligase buffer containing 0.4 mM ATP at 12.5° C. for 7 hours. Following transformation of *E. coli* strain JA221, NRRL B-15014, with a portion of the ligated mixture, plasmid DNAs were isolated from the ampicillin-resistant colonies, and one of them had the structure indicated at 130 in FIG. 11 and was designated pKEN037. Analysis of the DNA nucleotide sequence of pKEN037 revealed the DNA sequence depicted in FIG. 12, line e, in which one G-C pair was deleted between the Hind III and Bam HI cleavage sites (for reasons which are presently unknown), and confirmed that pKEN037 was the constitutive A-1 cloning vehicle.

7. Construction Of Plasmids pKEN039 and pKEN040

Figure 13:
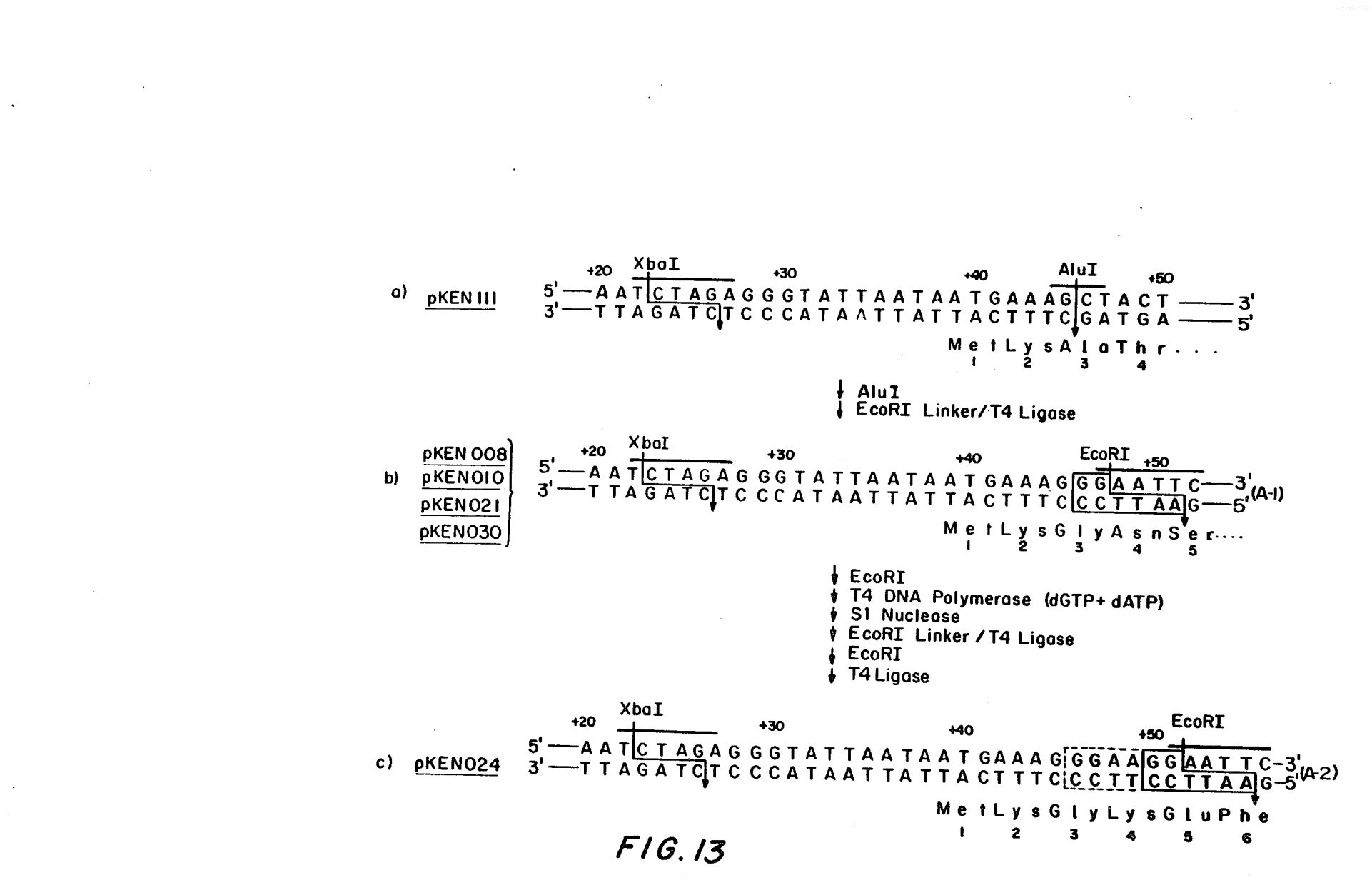

In order to accommodate DNA insert fragments with reading frames differing from that of pKEN037, the constitutive A-2 and A-3 lpp gene cloning vehicles were constructed by adjusting the reading frame of pKEN030 at the Eco RI cleavage site. FIG. 13, line a, and FIG. 14, line a, both illustrate the DNA sequence surrounding the translation initiation site of the prolipoprotein in pKEN111. As shown, this sequence includes an Alu I cleavage site between positions +45 and +46. In creating plasmid pKEN008, an Eco RI linker was attached to the Alu I terminus, resulting in the DNA sequence shown in FIG. 13, line b, and in FIG. 14, line b, in plasmids pKEN008, pKEN010, pKEN021 and pKEN030, and creating an Eco RI cleavage site between positions +47 and +48. The DNA sequence of pKEN030 was modified at the Eco RI site, as shown in FIG. 13, line c, and in FIG. 14, line c, to shift its reading frame by one base and by two bases, respectively.

To accomplish this result in the first case to produce a plasmid with the A-2 reading frame, 5 micrograms of pKEN030 plasmid DNA were digested completely with Eco RI restriction enzyme in 100 microliters of Eco RI buffer at 37° C. for 60 minutes. After phenol extraction and ethanol precipitation, the DNAs were treated with 3 units of T4 DNA polymerase in 30 microliters of polymerase buffer in the presence of 0.1 mM dGTP and 0.1 mM dATP at 12.5° C. for 45 minutes. The reaction was terminated by adding EDTA to a final concentration of 25 mM, followed by phenol extraction. By this procedure, half of the 4-base Eco RI "sticky end" was filled in with two A residues. The remaining two single-strand A residues were removed by treating with S1 Nuclease in 200 microliters of S1 buffer at 20° C. for one hour. The reaction was terminated by adding 20 microliters of 0.5M Tris:HCl (pH 8.0) and 20 microliters of 0.25M EDTA. The mixture was extracted with phenol and dialyzed overnight against 0.01×SSC. The DNAs were precipitated with 2.5 volumes of ethanol, centrifuged and re-suspended in 100 microliters of 0.3M Na-acetate. The DNAs were re-precipitated with 250 microliters of ethanol, centrifuged, and dried under vacuum.

In order to restore the Eco RI cleavage site, one microgram of the S1-treated DNA was first mixed with 70 pmoles of phosphorylated eco RI linker and blunt-end ligated with 3.2 units of T4 DNA ligase in 11 microliters of ligase buffer containing 0.6 mM ATP at 12.5° C. for 16 hours. The mixture was then diluted to 50 microliters with Eco RI buffer and heated at 60° C. for 10 minutes. Twenty units of Eco RI restriction endonuclease were added, and the mixture was incubated at 37° C. for one hour to remove superfluous linker molecules and to create Eco RI cohesive termini. The reaction mixture was then extracted with phenol, and the DNAs were precipitated with ethanol. Plasmid DNAs (0.5 micrograms) were re-circularized by treating with 0.8 units of T4 DNA ligase in 15 microliters of ligase buffer containing 0.4 mM ATP at 12.5° C. for 7 hours. Eight microliters of the ligated mixture were used to transform E. coli strain JA221, NRRL B-15014. Plasmid DNAs were purified from 3 ampicillin-resistant transformants, which had been grown overnight in one hundred ml of L broth containing 50 micrograms/ml of ampicillin, and the DNA sequences of their Eco RI cleavage sites were determined. One of them was found to have the sequence shown in FIG. 13, line c, and was designated pKEN024 (A-2).

To construct a plasmid with the A-3 reading frame, 5 micrograms of pKEN030 plasmid DNA were digested completely with Eco RI restriction enzyme in 100 microliters of Eco RI buffer at 37° C. for 60 minutes. After phenol extraction and ethanol precipitation, the Eco RI "sticky ends" were removed by treating the DNA (4.4 micrograms) with 500 units of S1 Nuclease in 150 microliters of S1 buffer at 20° C. for one hour. The reaction was terminated by adding 15 microliters of 0.5M Tris:HCl (pH 8.0) and 15 microliters of 0.25M EDTA. The mixture was extracted with phenol and dialyzed for four hours against 0.01×SSC. The DNAs were precipitated with 2.5 volumes of ethanol, centrifuged and resuspended in 100 microliters in 0.3 Na-acetate. The DNAs were re-precipitated with 250 microliters of ethanol, centrifuged, and dried under vacuum.

In order to restore the Eco RI cleavage site, one microgram of the S1-treated DNA was first mixed with 240 pmoles of phosphorylated Eco RI linker and blunt-end ligated with 4 units of T4 DNA ligase in 15 microliters of ligase buffer containing 0.6 mM ATP at 12.5° C. for 16 hours. The mixture was then diluted to 250 microliters with Eco RI buffer and heated at 60° C. for 10 minutes. One hundred units of Eco RI restriction endonuclease were added, and the mixture was incubated at 37° C. for one hour to remove superfluous linker molecules and to create Eco RI cohesive termini. The reaction mixture was then extracted with phenol, and the DNAs were precipitated with ethanol. Plasmid DNAs (0.3 micrograms) were re-circularized by treating with 0.8 units of T4 DNA ligase in 15 microliters of ligase buffer containing 0.4 mM ATP at 12.5° C. for 7 hours. Eight microliters of the ligated mixture were used to transform E. coli strain JA221, NRRL B-15014. Plasmid DNAs were purified from 3 ampicillin-resistant transformants, which had been grown overnight in one hundred ml of L broth containing 50 micrograms/ml of ampicillin, and the DNA sequences at their Eco RI cleavage sites were determined. One of them was found to have the sequence shown in FIG. 14, line c, and was designed pKEN036 (A-3).

Figure 15:
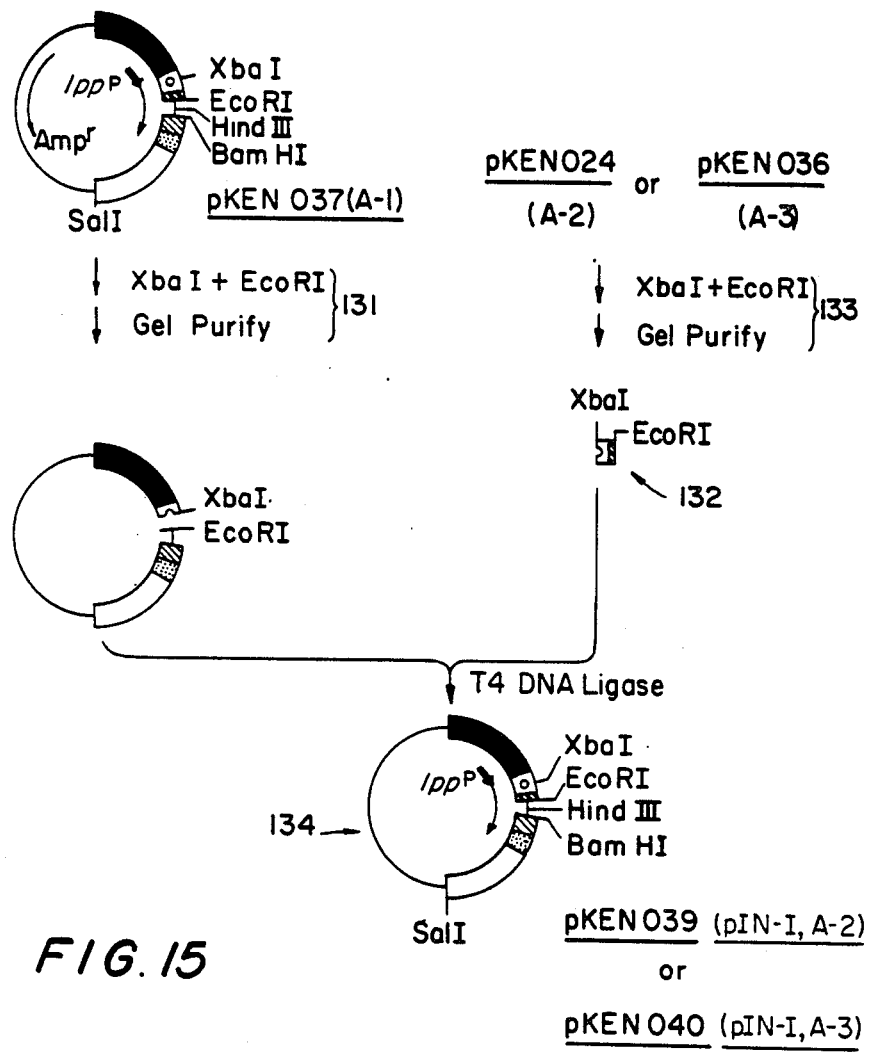

To change the translational reading frame of pKEN037 (A-1) into the two other reading frames (A-2 and A-3), the smaller Xba I-Eco RI fragment of pKEN037 was replaced with the smaller Xba I-Eco RI fragments from pKEN024 (A-2) or pKEN036 (A-3), as shown schematically in FIG. 15, using the following procedure: 3 micrograms of pKEN037 were first digested (as shown at 131 in FIG. 15) with 6 units of Xba I restriction enzyme in 50 microliters of Bam HI buffer at 37° C. for one hour, and after inactivation of the Xba I enzyme, the linearized DNA fragments were further digested with 6 units of Eco RI restriction enzyme in 100 microliters of Eco RI buffer at 37° C. for one hour. The larger Xba I-Eco RI fragment was separated from the smaller fragment by agarose gel electrophoresis: the DNA fragments in the agarose gel were stained with ethidium bromide (one microgram/ml), and the band corresponding to the larger fragment was cut out. The DNA fragments in this band were eluted from the gel after freezing. Ethidium bromide was removed from the DNA fragments by phenol extraction, and the DNAs were recovered by ethanol precipitation.

The dried DNA fragments were dissolved in 20 microliters of water, and one microliter aliquots of this pKEN037 DNA fragment mixture were combined with 0.1 micrograms of each of the smaller Xba I-Eco RI restriction fragments (illustrated at 132 in FIG. 15) previously obtained from pKEN024 or pKEN036 by double-digestion of each plasmid with Xba I and Eco RI restriction enzymes followed by gel purification (as shown at 133 in FIG. 15). The "sticky ends" of the Xba I-Eco RI fragments were joined by treatment with 0.2 units of T4 DNA ligase in 20 microliters of ligase buffer containing 0.4 mM ATP at 12.5° C. for 7 hours, following which a portion of the ligated mixture was used to transform E. coli strain JA221, NRRL B-15014. Among the ampicillin-resistant transformants, plasmid DNAs having the A-2 and A-3 reading frames were obtained, and these were designated pKEN039 and pKEN040, respectively, each having the structure shown at 134 in FIG. 15.

It will be appreciated that the foregoing was the experimental procedure used to construct plasmids pKEN039 (A-2) and pKEN040 (A-3) in the first instance. However, it will be understood by those skilled in the art that an alternative method exists with which to construct those plasmids. Specifically, the DNA sequence in the vicinity of the Eco RI cleavage site of plasmid pKEN037 (A-1) can itself be modified according to the scheme illustrated in FIG. 13, lines b and c, or the scheme shown in FIG. 14, lines b and c, to yield directly the structure of plasmids pKEN039 (A-2) or pKEN040 (A-3), respectively.

B. Construction Of B Site Plasmids (pIN-I)

FIGS. 16–21 schematically illustrate the manner in which constitutive recombinant plasmids incorporating the B insertion site were constructed, and may be referred to in connection with the following more particularized discussion.

1. Construction Of Plasmid pKEN221

The first step in the construction of the B site expression plasmids was to construct a plasmid to serve as a source of lpp gene fragments having a restriction enzyme cleavage site at or near the signal peptide cleavage site. The gene chosen codes for the lipoprotein of S. marcescens, and has a Fnu4H-I restriction endonuclease recognition sequence at the 3' end of the signal peptide. The plasmid chosen to receive the S. marcesens lpp gene was pBR322.

Figure 16:
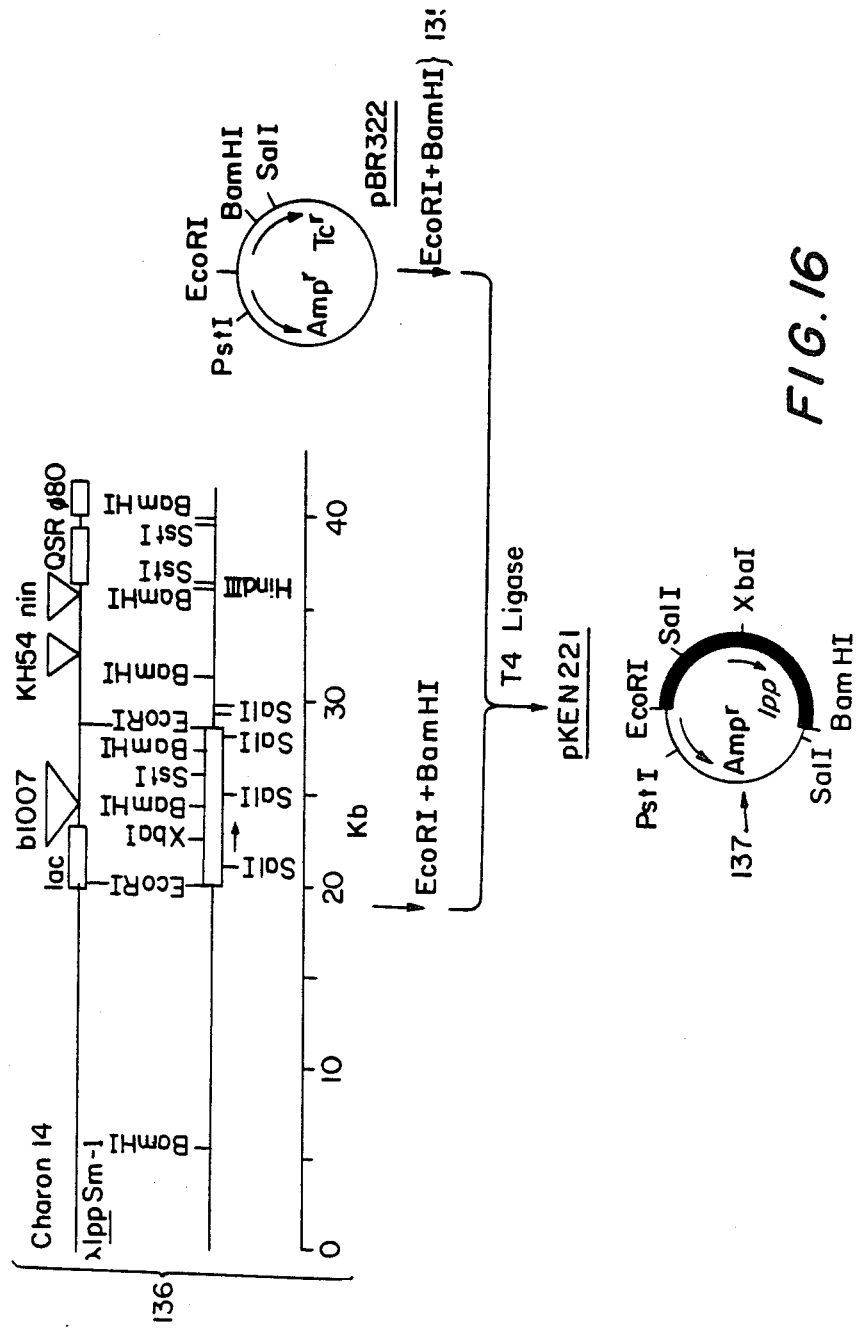

As shown schematically at 135 in FIG. 16, 2 micrograms of plasmid pBR322 DNA were digested to completion with two units of the restriction endonuclease Bam HI in 50 microliters of Bam HI buffer at 37° C. for 60 minutes. After inactivation of Bam HI enzyme by heating at 60° C. for 10 minutes, 2 units of Eco RI and 100 microliters of Eco RI buffer were added. The mixture was further incubated at 37° C. for 60 minutes, and the reaction was then terminated by phenol extraction, after which the linearized DNA fragments were recovered by ethanol precipitation.

An 8.5 Kb DNA fragment containing the S. marcesens lpp gene was separately derived, as shown at 136 in FIG. 16, from a hybrid λ phage carrying the S. marcescens lpp gene (designated λlppSm-1). The lpp gene had previously been cloned into a λ phage vector, Charon 14 (Blattner, F., et. al., Science 196: 161–169 [1977]), as follows: Total DNA (200 micrograms) isolated from S. marcesens was digested with 200 units of the restriction enzyme Eco RI. DNA fragments were separated on a preparative agarose gel, and fractions of DNA fragments of approximately 8.5 Kb which showed positive hybridization with 5'-$^{32}$P-lipoprotein mRNA were collected, using the Southern hybridization technique. A mixture of 8.5 Kb Eco RI fragments (enriched approximately twenty-fold) and Eco RI-cleaved Charon 14 vector DNA was reacted with T4 DNA ligase. Ligated DNA was used to transfect E. coli K802, NRRL B-15016. Recombinant phages carrying the lpp gene were screened by the plaque hybridization technique of Benton and Davis using 5'-$^{32}$P-lipoprotein mRNA. One of the plaques examined which gave positive hybridization was designated λlppSm-1.

Two micrograms of λlppSm-1 DNA were then digested completely with the restriction enzymes Bam HI and Eco RI, in the same manner as described immediately above with respect to linearization of pBR322, and 0.5 micrograms of the λlppSm-1 DNA fragments were combined with 0.5 micrograms of the previously-linearized plasmid pBR322 DNA in 40 microliters of ligase buffer. The mixture was heated at 37° C. for 5 minutes, and the Eco RI and Bam HI cohesive termini were annealed by incubating at 4° C. for 16 hours and then at 0° C. for 1 hour. After adding ATP (0.4 mM final) and 0.4 units of T4 DNA ligase, the mixture was incubated at 12.5° C. for 7 hours.

One-fourth of the ligation mixture was thereafter used to transform E. coli lpp deletion mutant strain JE5527, NRRL B-15012. Transformation was carried out as described in Cohen, S. N., et al., Proc. Natl. Acad. Sci U.S.A. 69: 2110–2114 (1972), and ampicillin-resistant transformants were grown overnight on Whatman 3 MM filter papers, placed on the surface of an L broth plate containing 50 micrograms/ml of ampicillin, and screened for lpp clones by colony hybridization. A 0.95 Kb Msp I fragment of λlppEc-1 containing the lpp gene was nicktranslated with [α-$^{32}$P]dATP and [α-$^{32}$P]dCTP, as described in Maniatis, T., et al., Proc. Natl. Acad. Sci. U.S.A. 72: 1184–1188 (1975), and was used as a $^{32}$P-probe. One of the transformants which gave positive hybridization was shown to contain the plasmid with the structure illustrated at 137 in FIG. 16, and this plasmid was designated pKEN221.

2. Construction Of Plasmid pKEN009

Figure 17:
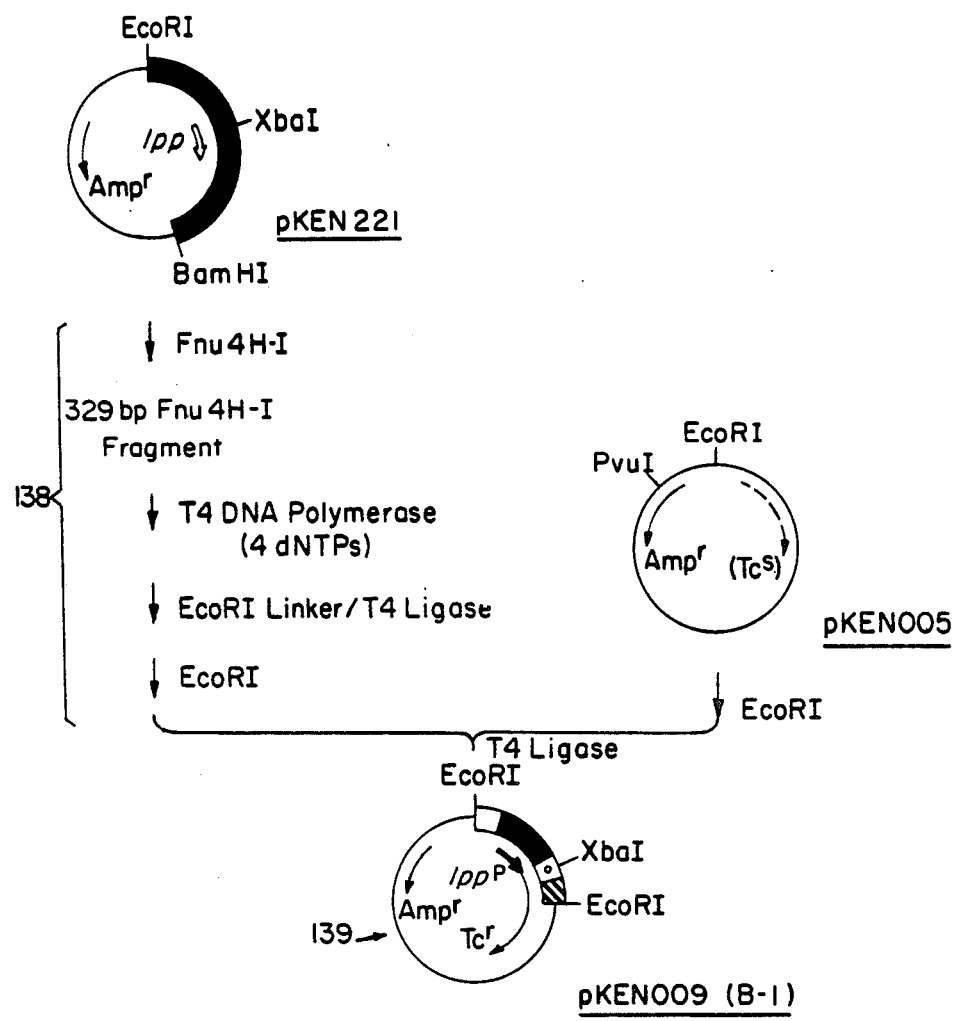

In order to construct the B site cloning vehicles, a 329 bp Fnu4H-I fragment containing the lpp promoter and 5'-untranslated region, as well as the signal peptide region of the S. marcescens lpp gene (this fragment is shown schematically at 105B in FIG. 5) was first cloned into pKEN005, as illustrated at 138 in FIG. 17, as follows: 80 micrograms of pKEN221 plasmid DNA were digested to completion with 100 units of the restriction endonuclease Fnu4H-I (New England Biolabs) in 400 microliters of Hae III buffer, and a 324 bp Fnu4H-I fragment was purified by acrylamide gel electrophoresis.

Since digestion with Fnu4H-I restriction enzyme results in the production of fragments with "sticky ends" at both termini, these sticky ends were modified by filling in with T4 DNA polymerase to create blunt ends. Two micrograms of the purified 324 bp Fnu4H-I fragment were treated with 3 units of T4 DNA polymerase in 20 microliters of polymerase buffer in the presence of 0.1 mM each of dATP, dGTP, dCTP and dTTP at 12.5° C. for 45 minutes. After phenol extraction and ethanol precipitation, the DNA fragments were mixed with 400 pmoles of phosphorylated Eco RI linker and treated with 4 units of T4 DNA ligase in 20 microliters of ligase buffer containing 0.6 mM ATP at 12.5° C. for 16 hours. The mixture was diluted to 300 microliters with Eco RI buffer and digested with 150 units of Eco RI restriction enzyme to create Eco RI cohesive termini.

One microgram of the Eco RI-digested fragments was then mixed with 0.5 micrograms of Eco RI-digested pKEN005 plasmid DNA, and treated with 0.4 units of T4 DNA ligase in 40 microliters of ligase buffer containing 0.6 mM ATP at 12.5° C. for 16 hours. Twenty microliters of the ligated mixture was used to transform E. coli strain JE5519, NRRL B-15013. Upon restriction enzyme analysis of the plasmid DNAs obtained from tetracycline-resistant transformants by the rapid alkaline denaturation method, one of the plasmids was found to carry a 334 bp Eco RI fragment derived from the 329 bp Fnu4H-I fragment, and this plasmid (depicted schematically at 139 in FIG. 17) was designated pKEN009. DNA nucleotide sequence analysis of the pKEN009 plasmid DNA showed that the Eco RI site in pKEN009 lies at the B insertion site and corresponds with the B-1 reading frame. This plasmid has the DNA sequence illustrated in FIG. 19, line b, and in FIG. 20, line b. For reasons which are not understood at present, it was found that three base pairs had been inserted in the region of position +90 (resulting in the addition of one extra amino acid residue at this position) and that an extra G-C pair had been inserted at position +99. The surprising cumulative effect of these changes was to convert the amino acid sequence in the region of the signal peptide cleavage site from that of the S. marcescens lpp gene to that of the E. coli lpp gene.

3. Construction Of Plasmids pKEN017, pKEN026 and pKEN027

Figure 18:
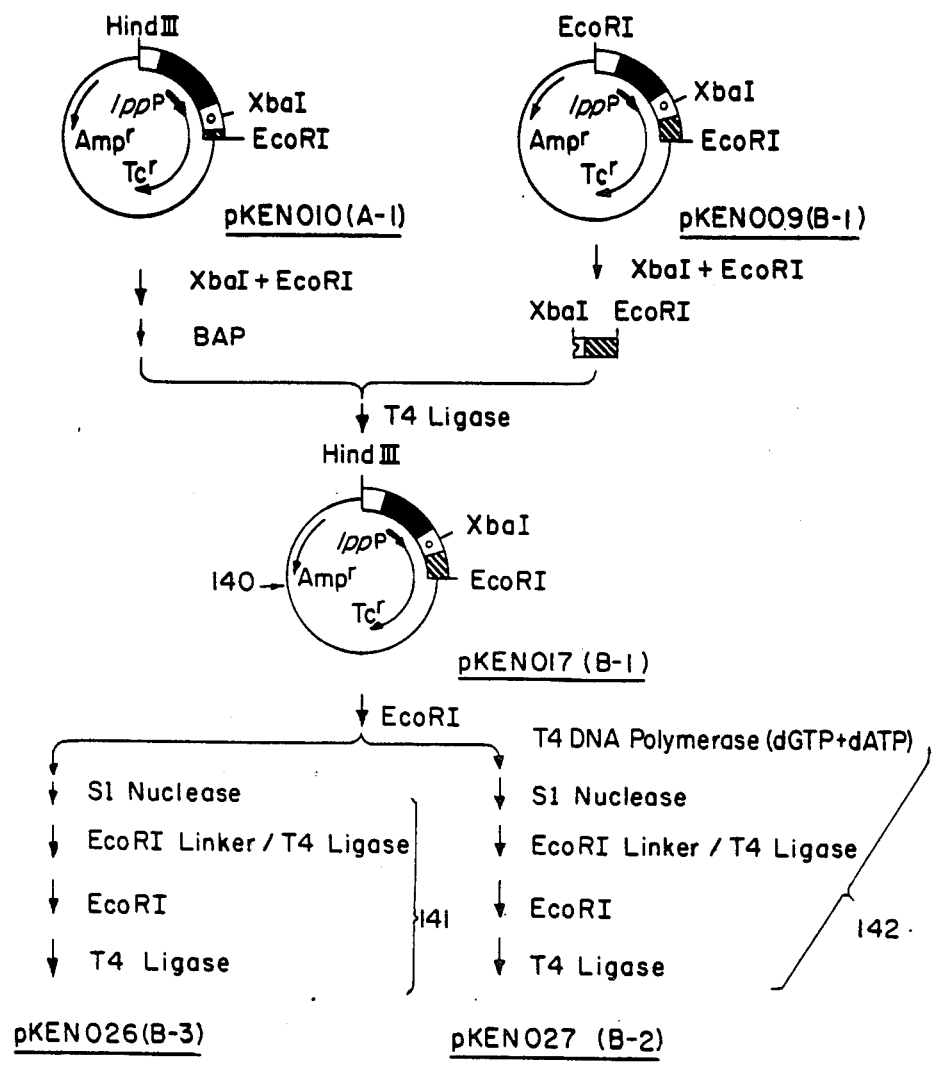

In order to construct constitutive B site expression plasmids corresponding to the B-2 and B-3 reading frames, it was first necessary to eliminate one of the two Eco RI cleavage sites of pKEN009. FIG. 18 depicts schematically the strategy for removing the Eco RI site located upstream of the lpp promoter. This procedure involved transferring an 80 bp Xba I-Eco RI fragment (containing the signal peptide and a portion of the 5'-untranslated region of the S. marcescens lpp gene) from pKEN009 into the Xba I-Eco RI sites of pKEN010.

In order to accomplish this result, 5 micrograms of pKEN010 plasmid DNA were first digested with 5 units of Xba I restriction endonuclease in 50 microliters of Bam HI buffer, followed by digestion with 5 units of Eco RI restriction enzyme in 100 microliters of Eco RI buffer. The linearized DNA was then treated with 5 microliters of BAP in 100 microliters of 10 mM Tris:HCl (pH 8.0) and 0.1 mM EDTA at 37° C. for 30 minutes. Plasmid DNAs were extracted with phenol and precipitated with ethanol, and 0.5 micrograms of the DNA were mixed with 0.2 micrograms of an 80 bp Xba I-Eco RI fragment, which had previously been obtained by digestion of 50 micrograms of pKEN009 plasmid DNA by Eco RI and Xba I restriction enzymes, followed by polyacrylamide gel electrophoresis. The DNA mixture was treated with 0.4 units of T4 DNA ligase in 40 microliters of ligase buffer containing 0.4 mM ATP at 12.5° C. for 16 hours. Twenty microliters of the ligated mixture were used to transform *E. coli* strain JE5519, NRRL B-15013. Upon restriction enzyme analysis of the plasmid DNAs obtained from ampicillin-resistant transformants by the rapid alkaline denaturation method, one plasmid was found to contain the desired 80 bp Xba I-Eco RI fragment carrying the signal peptide region of the *S. marcescens* lpp gene in the B-1 reading frame, as shown at 140 in FIG. 18, and that plasmid was designated pKEN017.

Figure 19:
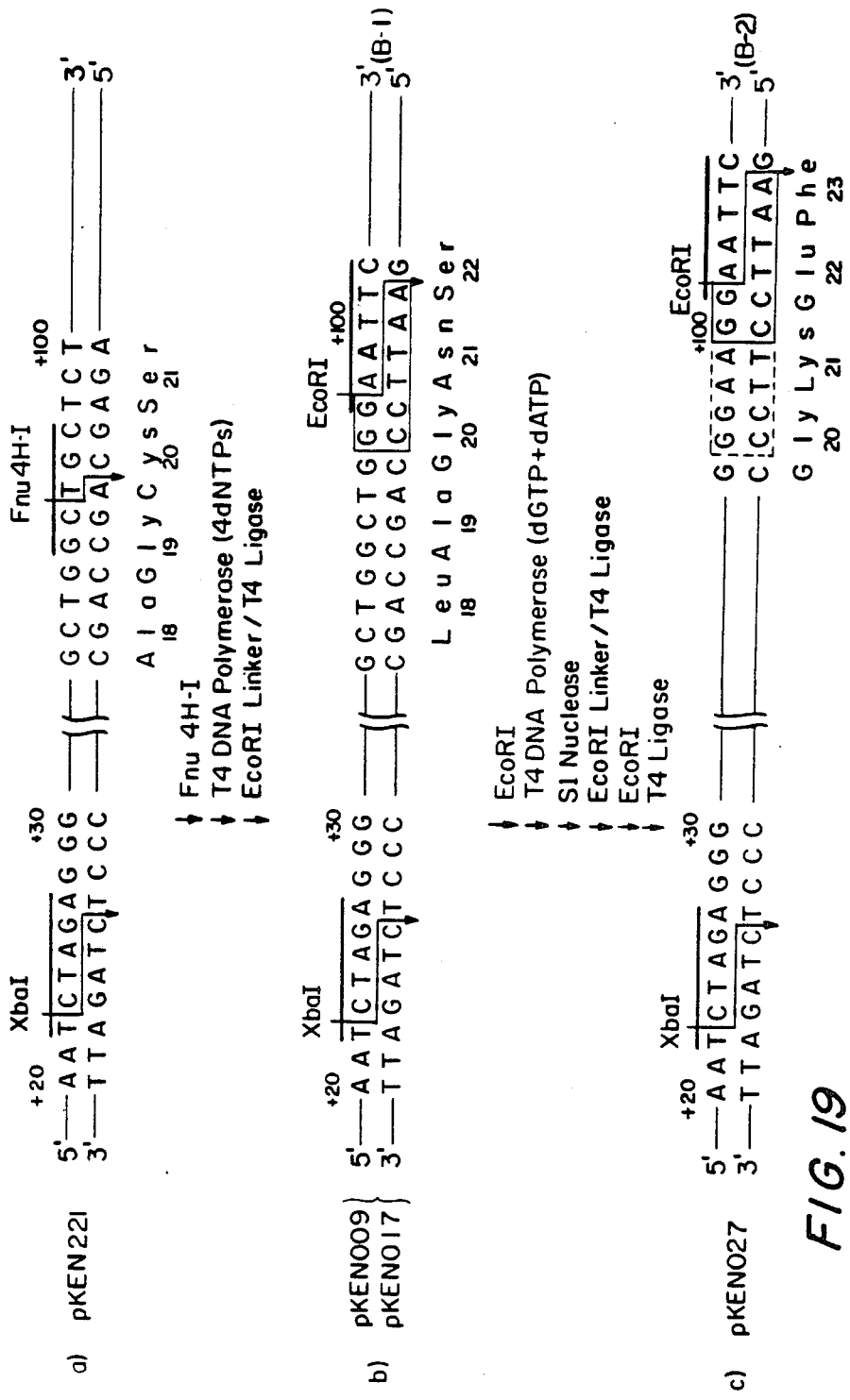
Figure 20:
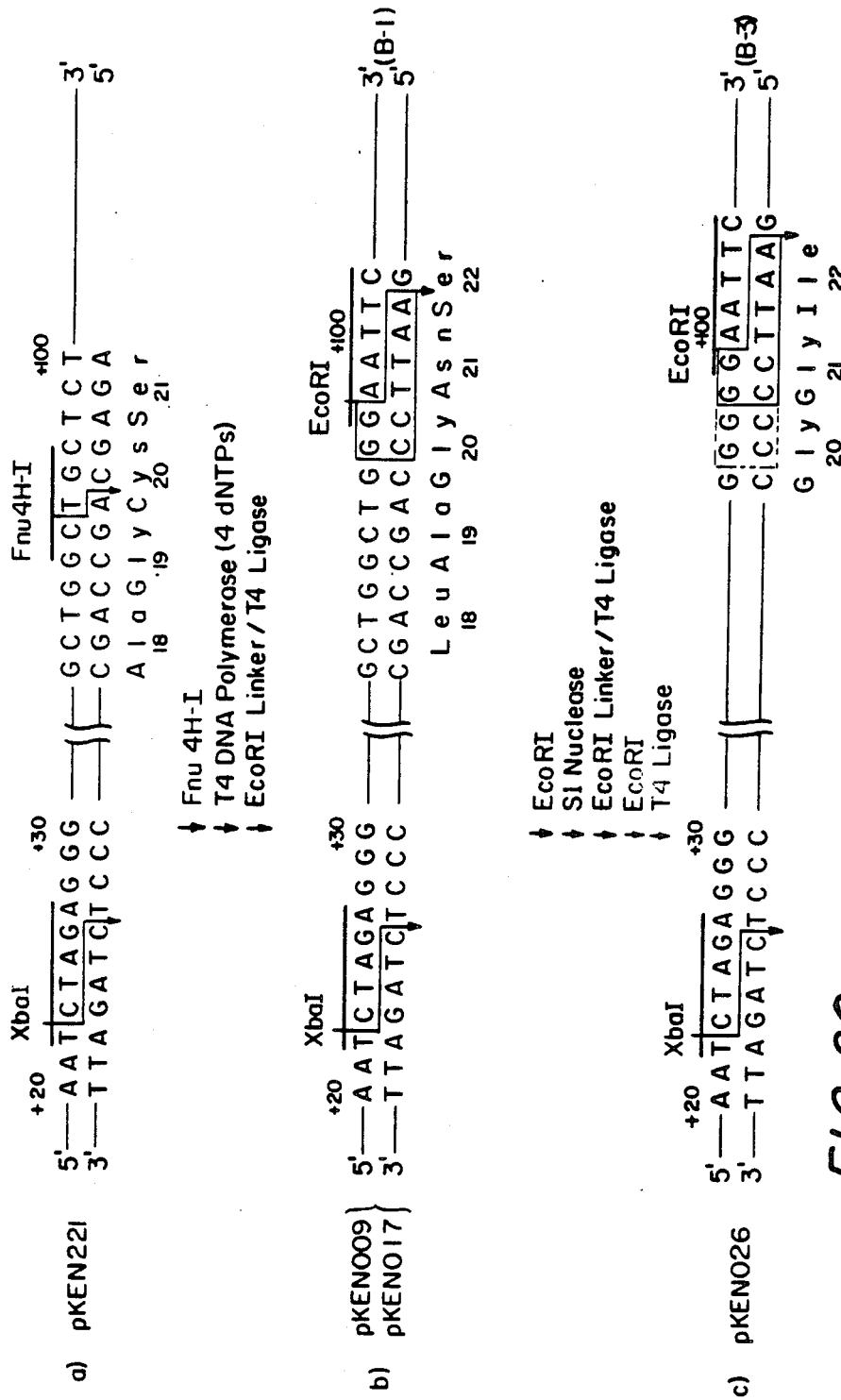

The reading frame at the B insertion site in pKEN017 was then modified to yield plasmids corresponding to the B-2 and B-3 reading frames, according to the methods previously described for changing the A-1 reading frame into the A-2 or A-3 reading frames, respectively. These procedures are illustrated schematically at 141 and 142 in FIG. 18, and the corresponding modifications of the DNA sequence around the Eco RI cleavage site are shown in FIGS. 19 and 20. It will be understood that the same procedures used to derive plasmids pKEN024 (A-2) and pKEN036 (A-3) from plasmid pKEN030 (A-1), described hereinabove in connection with FIGS. 13 and 14, can be used to derive plasmids pKEN026 (B-3) and pKEN027 (B-2) from plasmid pKEN017 (B-1).

4. Construction Of Plasmids pKEN041, pKEN047 and pKEN048

Figure 21:
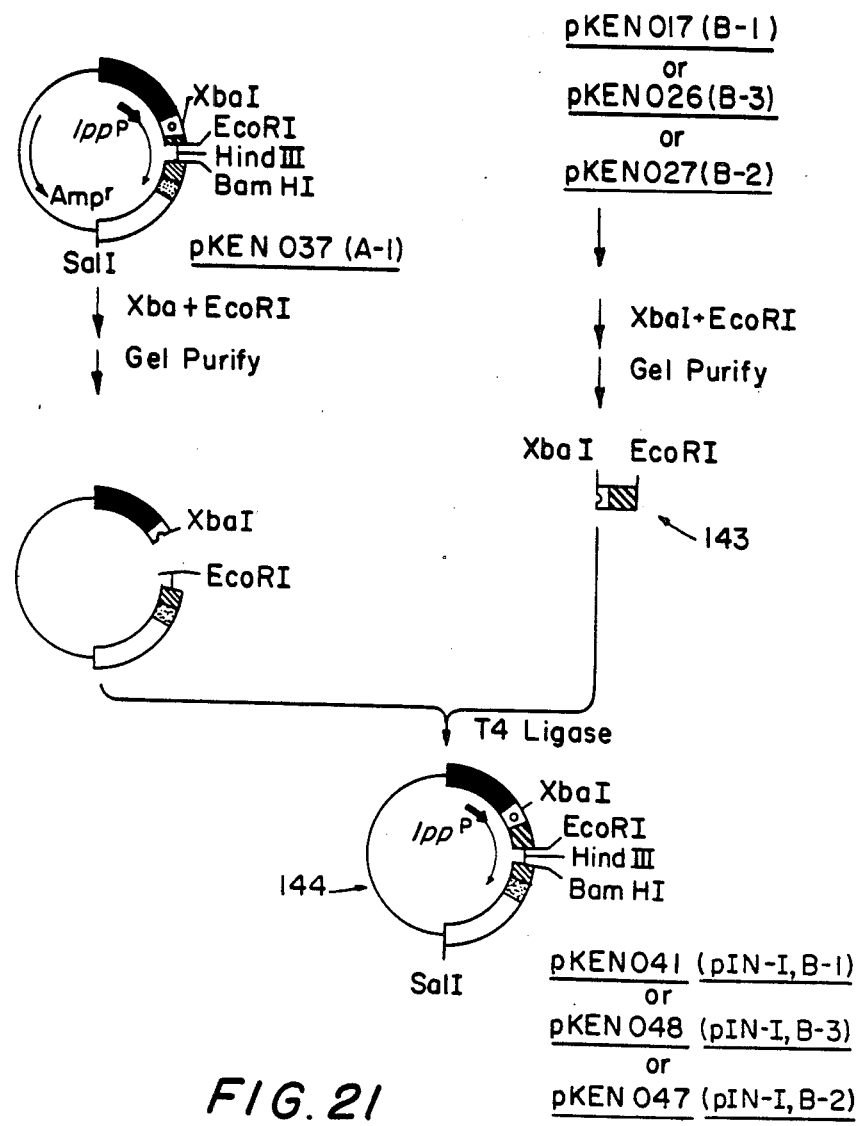

FIG. 21 illustrates schematically the last step in the construction of the B site cloning vehicles, which was to replace the Xba I-Eco RI A site fragment of pKEN037 with each of the three different Xba I-Eco RI B site fragments of pKEN017, pKEN026 and pKEN027. This was necessary in order to provide the B site plasmids with the same sequence of Eco RI, Hind III and Bam HI restriction enzyme recognition sequences at the exogenous DNA insertion site as contained in the A site plasmids. As shown schematically at 143 in FIG. 21, each of the three B site fragments derived from pKEN017, pKEN026 and pKEN027 contains the DNA sequence including the signal peptide obtained from the Fnu4H-I fragment of the *S. marcescens* lpp gene.

In order to accomplish this result, the same procedure was used to obtain the larger Xba I-Eco RI fragment of plasmid pKEN037 as was described hereinabove in connection with FIG. 15. One microliter aliquots of the aqueous pKEN037 DNA fragment mixture were each combined with a different Xba I-Eco RI smaller fragment (about 0.1 micrograms of each) previously obtained from pKEN017, pKEN026 and pKEN027, respectively, by double-digestion with XbaI and Eco RI restriction enzymes followed by gel purification. Each DNA mixture was treated with 0.2 units of T4 DNA ligase in 20 microliters of ligase buffer containing 0.4 mM ATP at 12.5° C. for 16 hours. Ten microliters of each of the ligated mixtures were used to transform *E. coli* strain JA221, NRRL B-15014. Among the ampicillin-resistant transformants, plasmid DNAs having the B-1, B-2 and B-3 reading frames were purified, and these were designated pKEN041, pKEN047 and pKEN048, respectively, each having the structure shown at 144 in FIG. 21.

C. Construction Of C Site Plasmids (pIN-I)

FIGS. 22-26 schematically illustrate the manner in which constitutive recombinant plasmids incorporating the C insertion site were constructed, and may be referred to in connection with the following more particularized discussion.

1. Construction Of Plasmid pKEN006

Figure 22:
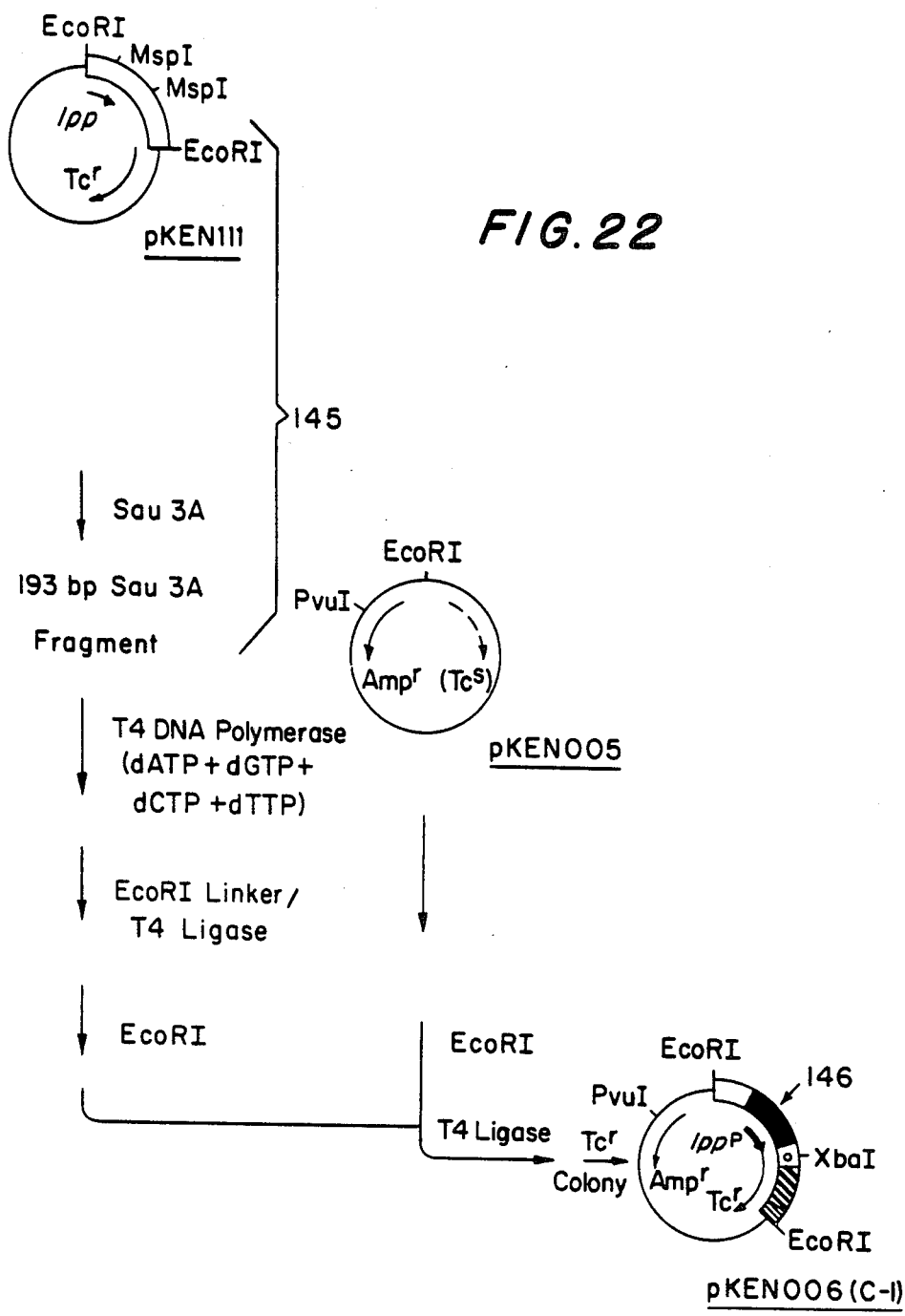

In order to construct the C site cloning vehicles, a 193 bp Sau 3A fragment containing the lpp promoter and 5'-untranslated region, as well as the signal peptide region and the first eight structural codons of the *E. coli* lpp gene (this fragment is shown schematically at 105C in FIG. 5) was first cloned into pKEN005, as illustrated at 145 in FIG. 22, as follows: 200 micrograms of pKEN111 plasmid DNA, which can be obtained by conventional means from *E. coli* CC620/pKEN111, NRRL B-15011, were digested to completion with 200 units of Sau 3A restriction endonuclease in 400 microliters of a reaction mixture comprising 10 mM Tris:HCl (pH 7.5), 10 mM $MgCl_2$, 60 mM NaCl, and 100 micrograms/ml BSA at 37° C. for one hour. After digestion was completed, phenol extraction was performed, the DNAs were recovered by ethanol precipitation, and a 193 bp Sau 3A fragment was purified by acrylamide gel electrophoresis.

Since digestion with Sau 3A restriction enzyme results in the production of fragments with "sticky ends" at both termini, these sticky ends were modified by filling in with T4 DNA polymerase to create blunt ends. Two micrograms of the purified 193 bp Sau 3A fragment were treated with 3 units of T4 DNA polymerase in 20 microliters of polymerase buffer in the presence of 0.1 mM each of dATP, dGTP, dCTP and dTTP at 12.5° C. for 45 minutes. After phenol extraction and ethanol precipitation, the DNA fragments were mixed with 400 pmoles of phosphorylated Eco RI linker and treated with 4 units of T4 DNA ligase in 20 microliters of ligase buffer containing 0.6 mM ATP at 12.5° C. for 16 hours. The mixture was diluted to 300 microliters with Eco RI buffer and digested with 150 units of Eco RI restriction enzyme to create Eco RI cohesive termini.

One microgram of the Eco RI-digested fragments was then mixed with 0.5 micrograms of Eco RI-digested pKEN005 plasmid DNA, and treated with 0.4 units of T4 DNA ligase in 40 microliters of ligase buffer containing 0.6 mM ATP at 12.5° C. for 16 hours. Twenty microliters of the ligated mixture were used to transform *E. coli* strain JE5519, NRRL B-15013. Upon restriction enzyme analyses of the plasmid DNAs obtained from tetracycline-resistant transformants by the rapid alkaline denaturation method, one of the plasmids was found to carry an Eco RI fragment derived from the 193 bp Sau 3A fragment, and this plasmid (depicted schematically at 146 in FIG. 22) was designated pKEN006. DNA nucleotide sequence analysis of the pKEN006 plasmid DNA showed that the Eco RI site in pKEN006 lies at the C insertion site and corresponds with the C-1 reading frame.

2. Construction Of Plasmids pKEN007, pKEN019 and pKEN046

Figure 23:
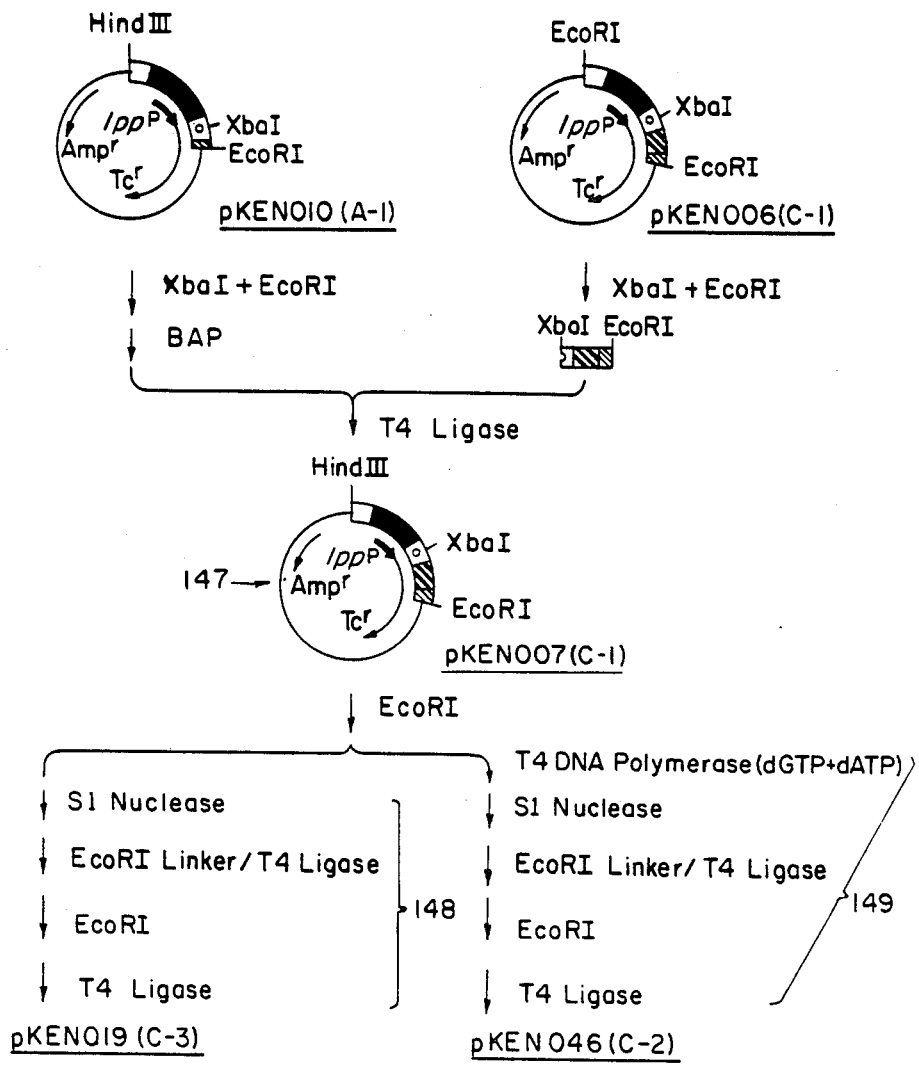

In order to construct C site expression plasmids corresponding to the C-2 and C-3 reading frames, it was first necessary to eliminate one of the two Eco RI cleavage sites of pKEN006. FIG. 23 depicts schematically the strategy for removing the Eco RI site located upstream of the lpp promoter. This procedure involved transferring a 106 bp Xba I-Eco RI fragment (containing the signal peptide, a portion of the 5'-untranslated region and a portion of the structural sequence of the *E. coli* lpp gene) from pKEN006 into the Xba I-Eco RI sites of pKEN010.

In order to accomplish this result, 5 micrograms of pKEN010 plasmid DNA were first digested with 5 units of Xba I restriction endonuclease in 50 microliters of Bam HI buffer, followed by digestion with 5 units of Eco RI restriction enzyme in 100 microliters of Eco RI buffer. The linearized DNA was then treated with 5 microliters of BAP in 100 microliters of 10 mM Tris:HCl (pH 8.0) and 0.1 mM EDTA at 37° C. for 30 minutes. Plasmid DNAs were extracted with phenol and precipitated with ethanol, and 0.5 micrograms of the DNA were mixed with 0.2 micrograms of a 106 bp Xba I-Eco RI fragment, which had previously been obtained by digestion of 50 micrograms of pKEN006 plasmid DNA by Eco RI and Xba I restriction enzymes, followed by polyacrylamide gel electrophoresis. The DNA mixture was treated with 0.4 units of T4 DNA ligase in 40 microliters of ligase buffer containing 0.4 mM ATP at 12.5° C. for 7 hours. Twenty microliters of the ligated mixture were used to transform *E. coli* strain JE5519, NRRL B-15013. Upon restriction enzyme analysis of the plasmid DNAs obtained from ampicillin-resistant transformants by the rapid alkaline denaturation method, one plasmid was found to contain the desired 106 bp Xba I-Eco RI fragment carrying the signal peptide region of the *E. coli* lpp gene in the C-1 reading frame, as shown at 147 in FIG. 23, and that plasmid was designated pKEN007.

Figure 24:
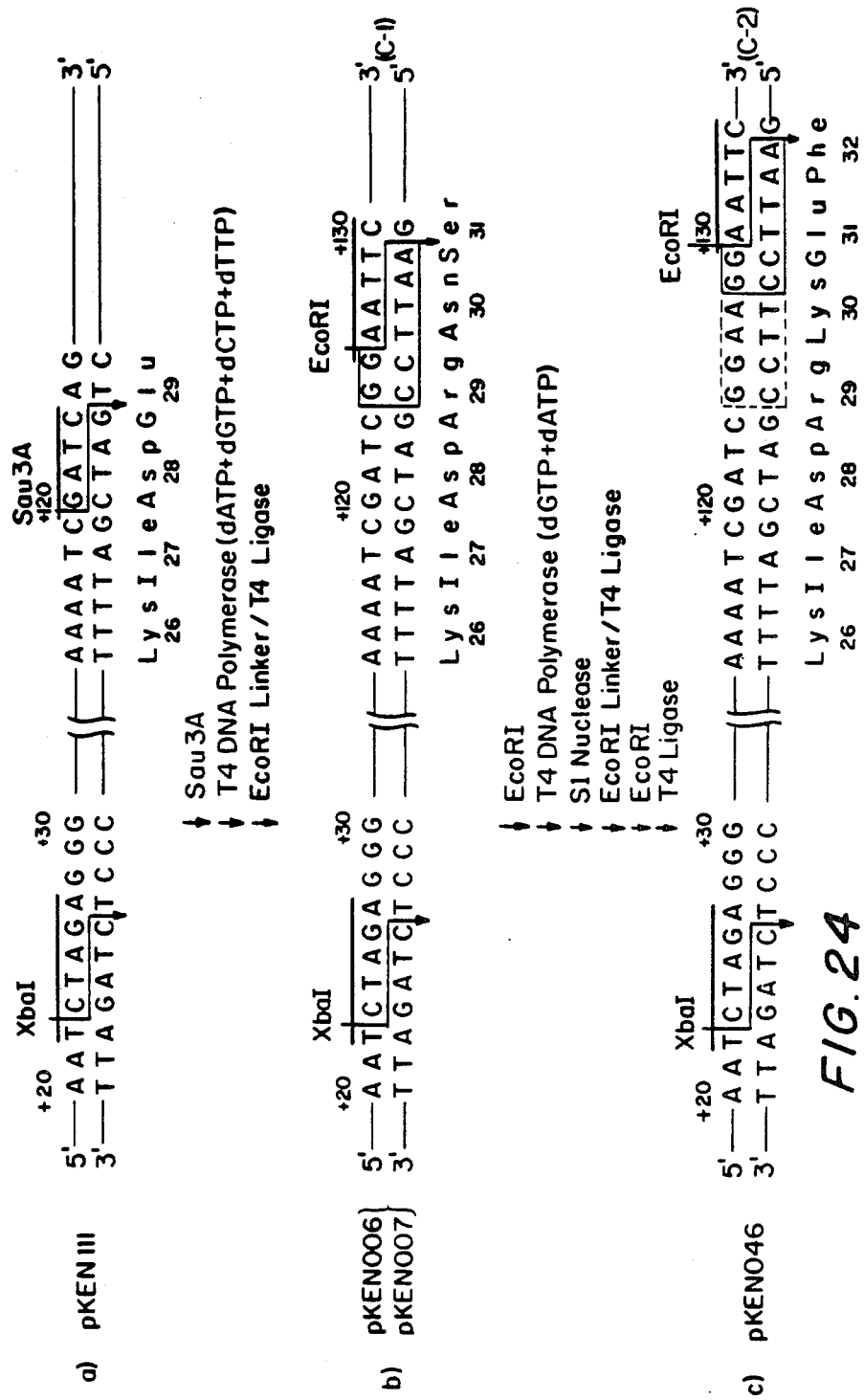
Figure 25:
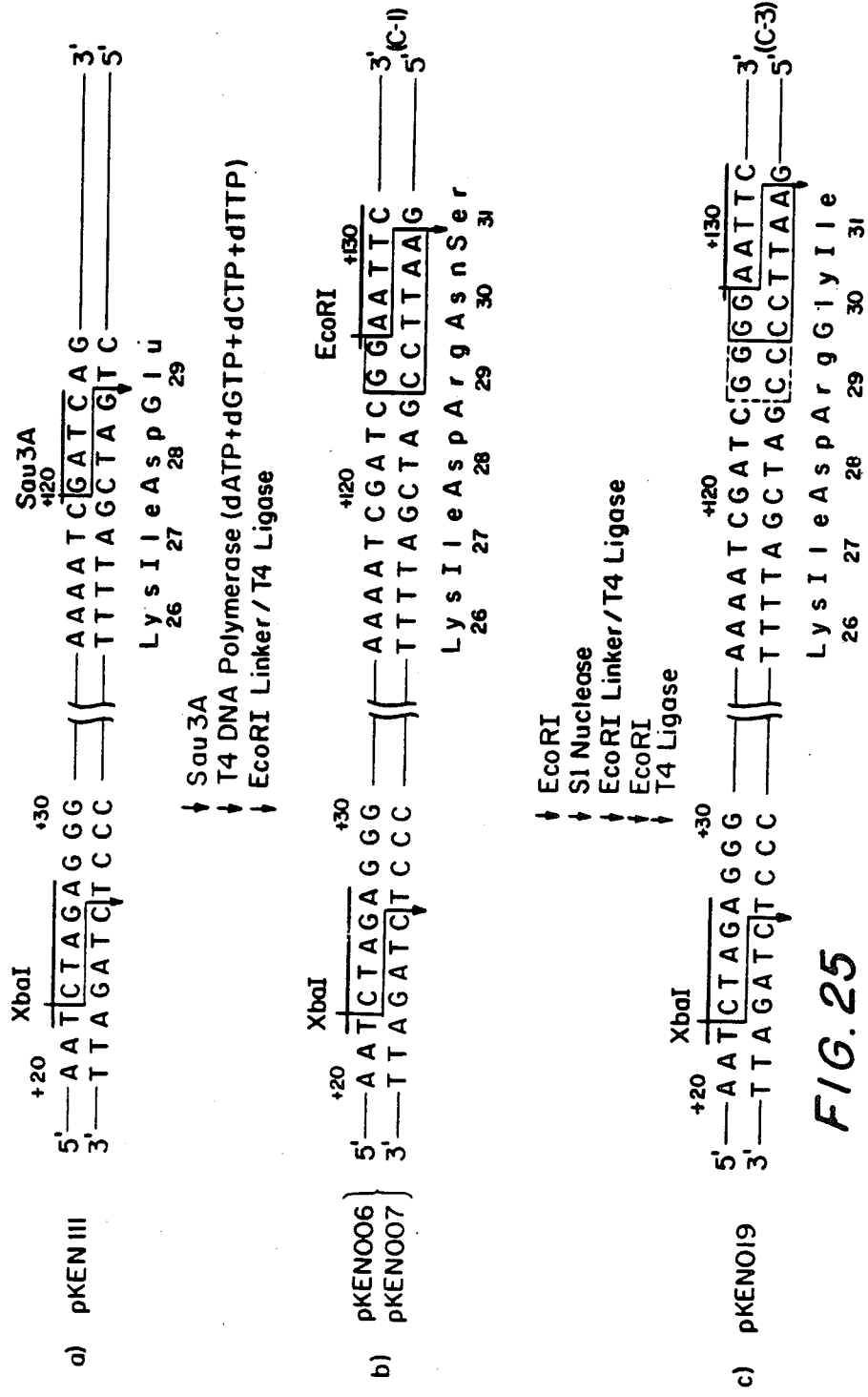

The reading frame at the C insertion site in pKEN007 was then modified to yield plasmids corresponding to the C-2 and C-3 reading frames, according to the methods previously described for changing the A-1 reading frame into the A-2 or A-3 reading frames, respectively. These procedures are illustrated schematically at 148 and 149 in FIG. 23, and the corresponding modifications of the DNA sequence around the Eco RI cleavage site are shown in FIGS. 24 and 25. It will be understood that the same procedures used to derive plasmids pKEN024 (A-2) and pKEN036 (A-3) from plasmid pKEN030 (A-1), described hereinabove in connection with FIGS. 13 and 14, can be used to derive plasmids pKEN046 (C-2) and pKEN019 (C-3) from plasmid pKEN007 (C-1).

3. Construction Of Plasmids pKEN042, pKEN043 and pKEN044

Figure 26:
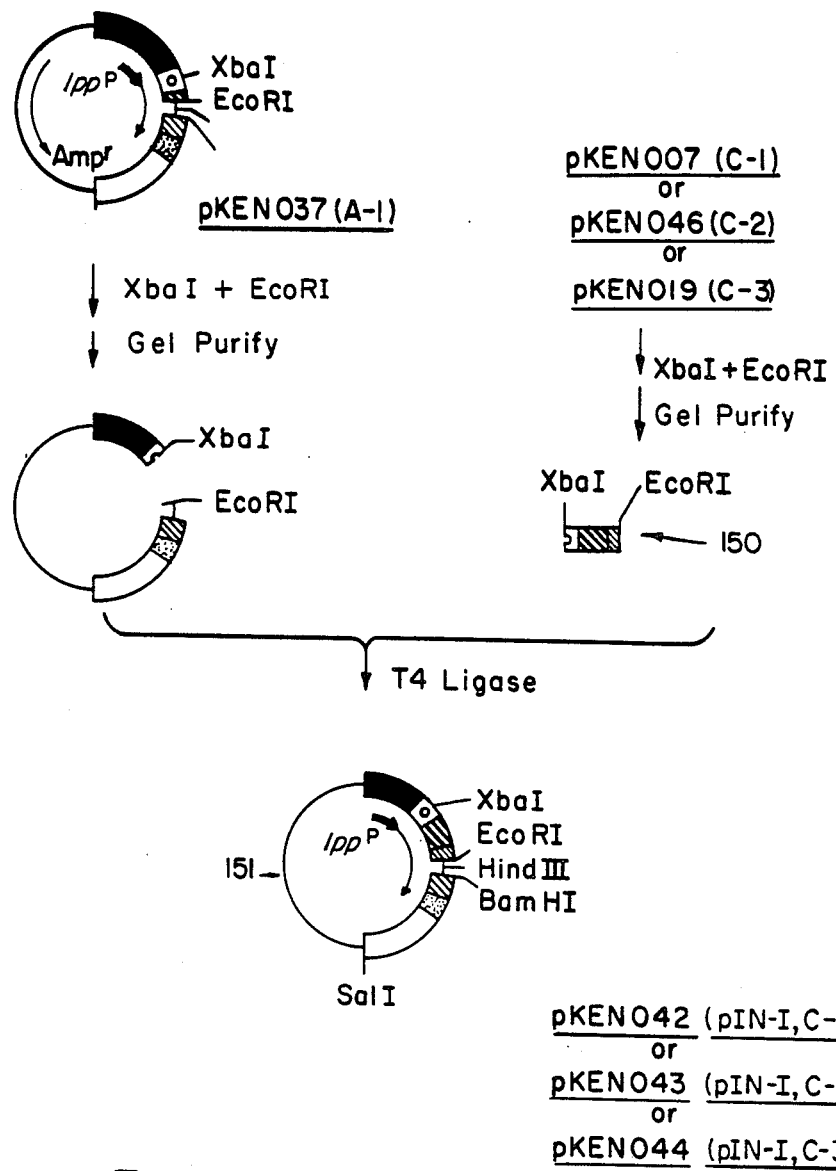

The last step in the construction of the constitutive C site expression plasmids was to substitute each of the three different Xba I-Eco RI C site fragments of pKEN007, pKEN046 and pKEN019 for the Xba I-Eco RI A site fragment of pKEN037, as illustrated in FIG. 26. This was done so that the C site plasmids would contain the same sequence of Eco RI, Hind III and Bam HI restriction enzyme recognition sequences at the exogenous DNA insertion site as contained in the A site and B site plasmids. As shown schematically at 150 in FIG. 26, each of the three C site fragments derived from pKEN007, pKEN046 and pKEN019 contains the DNA sequence including the signal peptides obtained from the Sau 3A fragment of the *E. coli* lpp gene.

In order to accomplish this result, the same procedure was used to obtain the larger Xba I-Eco RI fragment of pKEN037 as was described hereinabove in connection with FIG. 15. One microliter aliquots of the aqueous pKEN037 DNA fragment mixture were each combined with a different Xba I-Eco RI smaller fragment (about 0.1 micrograms of each) previously obtained from pKEN007, pKEN046 and pKEN019, respectively, by double digestion with Xba I and Eco RI restriction enzymes followed by gel purification. Each DNA mixture was treated with 0.2 units of T4 DNA ligase in 20 microliters of ligase buffer containing 0.4 mM ATP at 12.5° C. for 16 hours. Ten microliters of each of the ligated mixtures were used to transform *E. coli* strain JA221, NRRL B-15014. Among the ampicillin-resistant transformants, plasmid DNAs having the C-1, C-2 and C-3 reading frames were purified, and these were designated pKEN042, pKEN043 and pKEN044, respectively, each having the structure shown at 151 in FIG. 26.

D. Construction Of Inducible Expression (pIN-II) Plasmids

Figure 27:
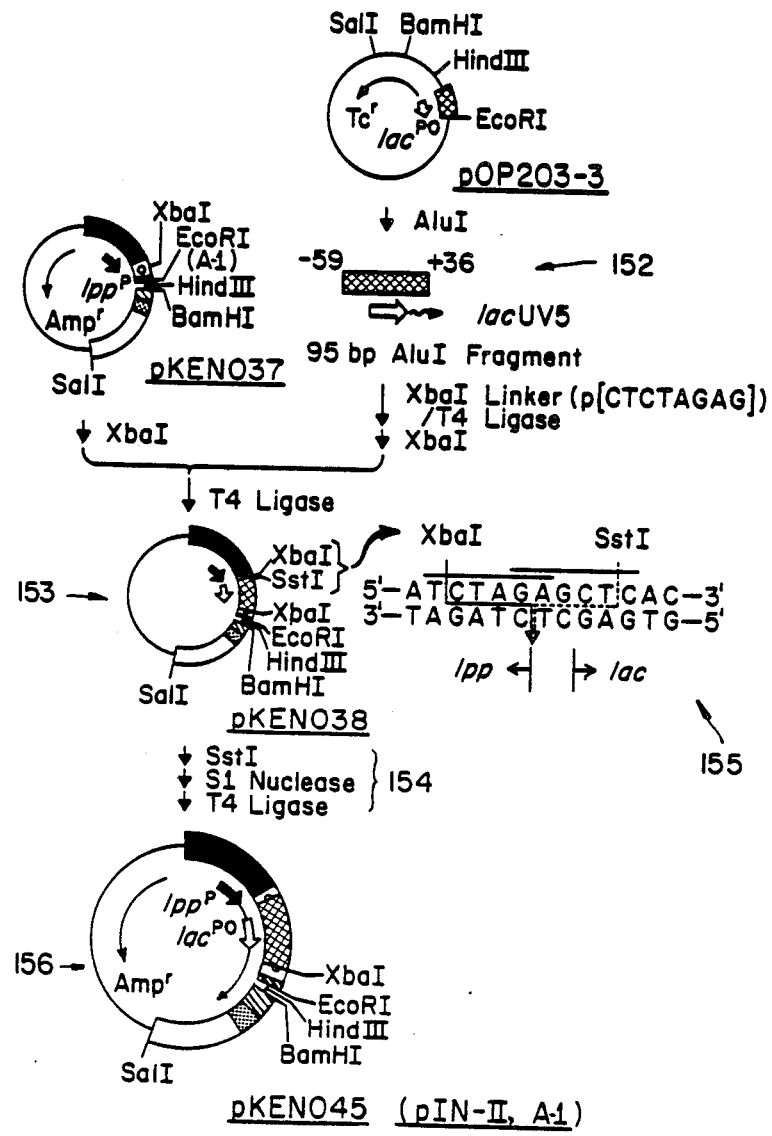

FIG. 27 schematically depicts the manner in which an inducible plasmid cloning vehicle incorporating the A insertion site in the A-1 reading frame (and corresponding to the constitutive plasmid pKEN037) was constructed. The lac UV5 promoter-operator was derived from plasmid pOP203-3 (obtained from Dr. F. Fuller, Dept. of Biochemistry and Molecular Biology, Harvard University). The lac UV5 promoter-operator is obtainable from *E. coli* 4288 recA/pkM006, NRRL B-15236, which is available to the public from the permanent collection of the Northern Regional Research Laboratory, U.S. Department of Agriculture, Peoria, Ill., U.S.A. The lac UV5 promoter-operator is carried on a 95 bp Xba I fragment of plasmid pKM006. The plasmid can be obtained from NRRL B-15236 by conventional means, and the 95 bp Xba I fragment can thereafter be isolated using known techniques.

Figure 29:
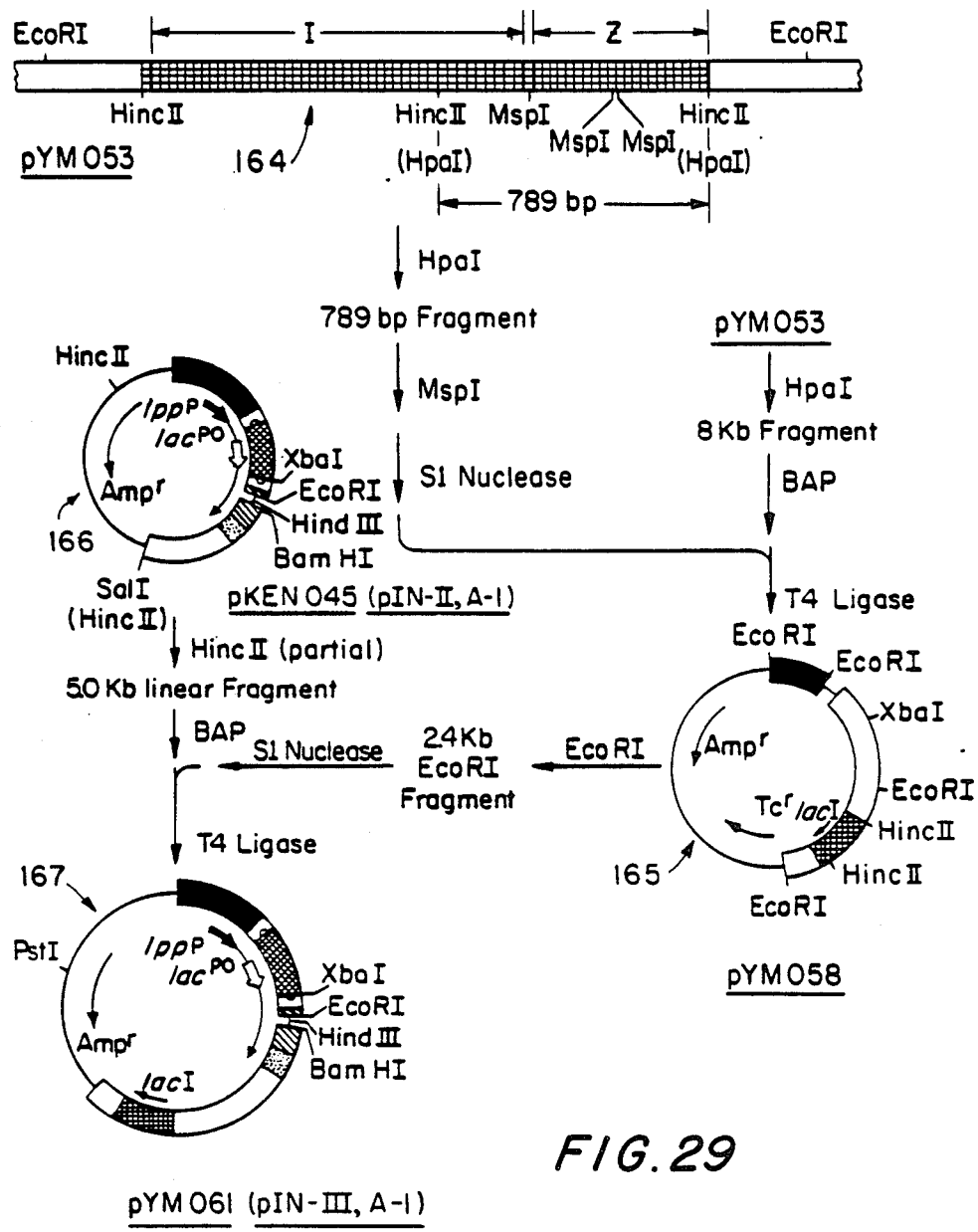
Figure 30A:
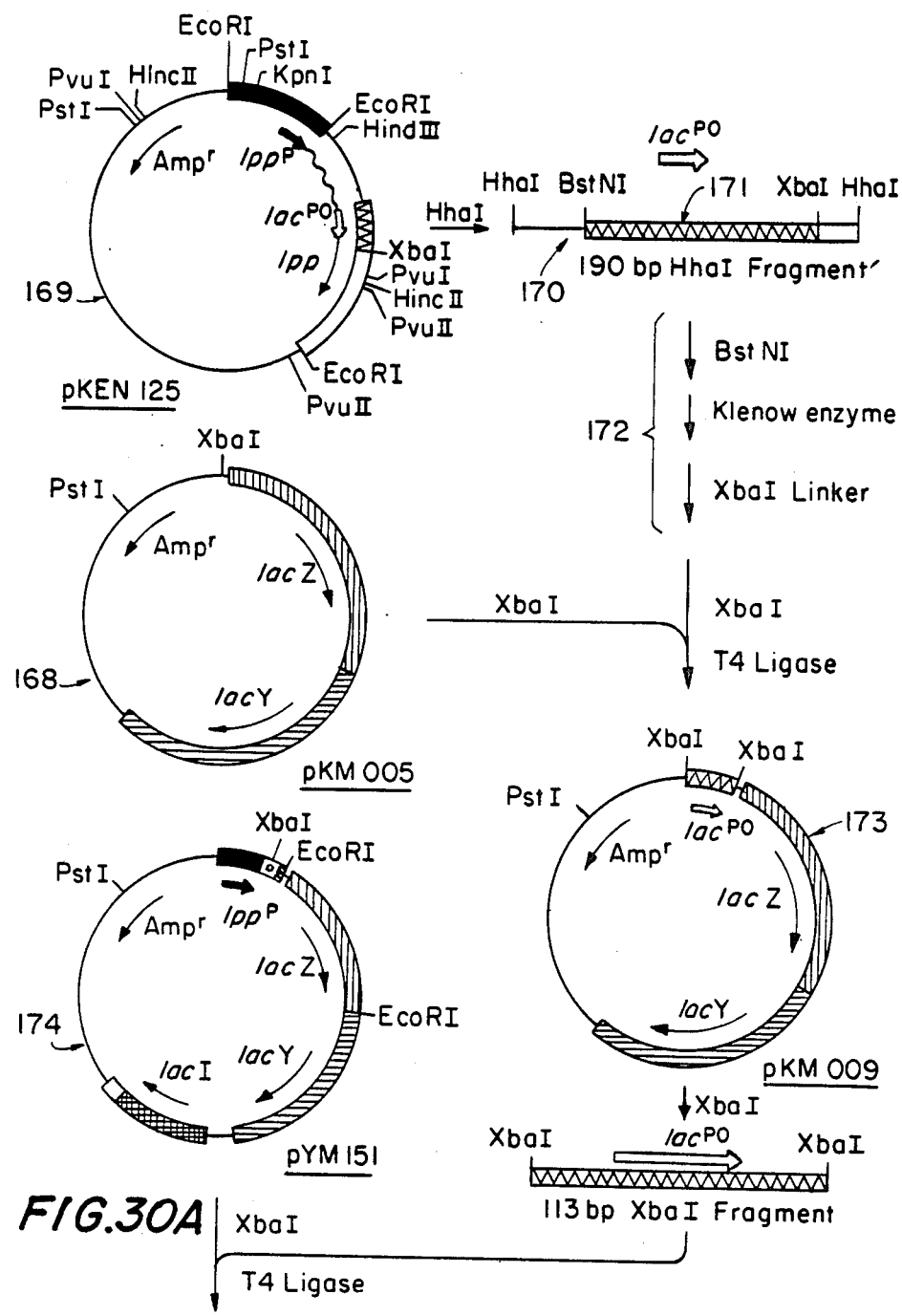
Figure 30B:
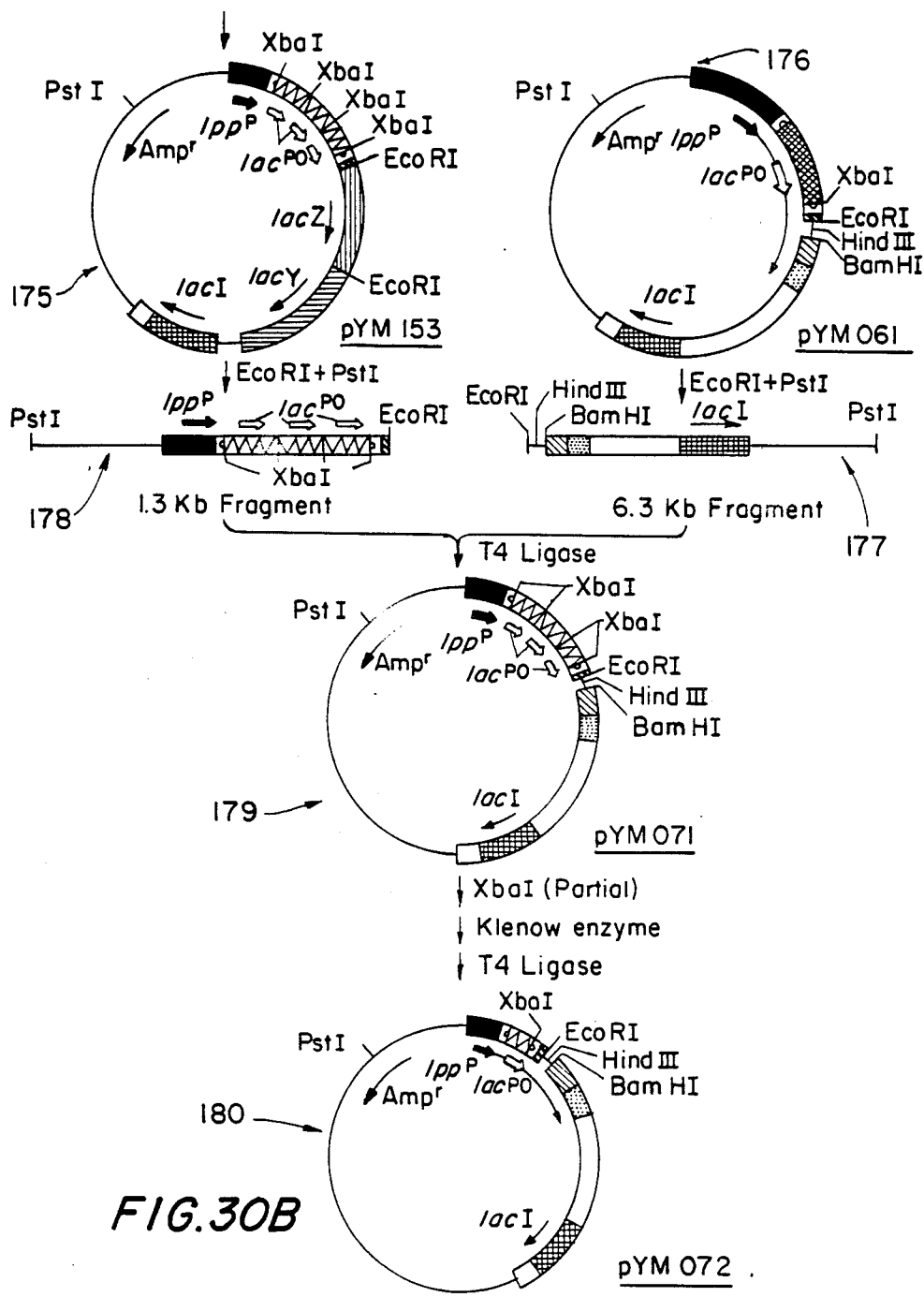

The lac UV5 promoter-operator was inserted at the Xba I cleavage site of pKEN037 (within the 5'-untranslated region of the lpp gene) according to the following procedure: 200 micrograms of pOP203-3 plasmid DNA were digested to completion with 200 units of Alu I restriction enzyme in 400 microliters of Hind III buffer, and a 95 bp Alu I fragment carrying lac UV5 promoter and operator region (illustrated schematically by the diagonally crosshatched segment at 152 in FIGS. 27, 29 and 30B) was purified by polyacrylamide gel electrophoresis. One microgram of the 95 bp Alu I fragment was mixed with 400 pmoles of phosphorylated Xba I linker (5'CTCTAGAG3'; obtained from Collaborative Research and phosphorylated in the same manner as described hereinabove), and blunt-end ligated with 5 units of T4 DNA ligase in 20 microliters of ligase buffer containing 0.6 mM ATP at 12.5° C. for 16 hours. The ligated mixture was diluted to 300 microliters with Bam HI buffer and treated at 60° C. for 10 minutes. The mixture was then treated with 100 units of Xba I restriction enzyme at 37° C. for one hour to create Xba I cohesive termini. The mixture was extracted with phenol, ethanol precipitated and lyophilized. The DNA fragments were then dissolved in 10 microliters of water, and 0.3 micrograms of the lac fragment thus obtained were mixed with 0.5 micrograms of pKEN037 plasmid DNA, which has previously been digested with Xba I restriction enzyme. The mixture was treated with 0.4 units of T4 DNA ligase in 20 microliters of ligase buffer containing 0.4 mM ATP at 12.5° C. for 16 hours to anneal the Xba I cohesive termini, thereby re-circularizing the plasmid. Ten microliters of the ligated mixture was used to transform *E. coli* JA221/F'lacI$^q$, NRRL B-15015, which was constructed by transferring the F' factor from X90/F'lacI$^q$ lac+ pro+ (obtained from Dr. J. Beckwith, Dept. of Biochemistry and Molecular Biology, Harvard University) into *E. coli* strain JA221, NRRL B-15014. *E. coli* strain JA221/F'lacI$^q$ is available to the public from the permanent collection of the Northern Regional Research Laboratory, U.S. Department of Agriculture, Peoria, Ill., U.S.A. Upon restriction enzyme analysis of the plasmid DNAs isolated from ampicillin-resistant transformants by the rapid alkaline denaturation method, one of them was found to contain one copy of the 95 bp Alu I fragment inserted at the Xba I site of pKEN037 in the correct orientation, as shown at 153 in FIG. 27, and this plasmid was designated pKEN038.

In order to simplify the construction of inducible plasmids containing the B and C insertion sites, it was first necessary to remove one of the two Xba I cleavage sites in pKEN038 surrounding the lac promoter-operator fragment. The Xba I cleavage site located upstream of the lac promoter-operator fragment was eliminated as shown schematically at 154 in FIG. 27. This was carried out utilizing the fact that attachment of the Xba I linker to the 95 bp lac promoter-operator fragment, as described in the preceding paragraph, resulted in the creation of a new Sst I cleavage site only at the upstream end of the lac promoter, but not at the downstream end. As shown at 155 in FIG. 27, the recognition sequence of the Sst I restriction enzyme overlaps with that of the Xba I enzyme. Thus, the deletion of the 4-base "sticky end" of the Sst I cleavage site using S1 nuclease should result in the deletion of part of the Xba I recognition sequence as well, effectively eliminating the Xba I cleavage site.

In order to accomplish this result, five micrograms of pKEN038 plasmid DNA were digested with 10 units of Sst I restriction endonuclease in 50 microliters of Bam HI buffer, and treated with 500 units of S1 nuclease in 200 microliters of S1 buffer at 20° C. for one hour. Blunt ends were joined by treatment of 0.5 micrograms of the S1-treated DNA with 5 units of T4 DNA ligase in 10 microliters of ligase buffer containing 0.6 mM ATP at 12.5° C. for 16 hours. Five microliters of the ligated mixture were used to transform *E. coli* strain JA221/F-'lacI$^q$, NRRL B-15015. A plasmid having the structure shown schematically at 156 in FIG. 27 was isolated after restriction enzyme analysis of the plasmid DNAs obtained from ampicillin-resistant transformants by the rapid alkaliine denaturation method, and that plasmid was designated pKEN045 (pIN-II, A-1).

There are several methods available with which to construct pIN-II plasmids corresponding to the A-2 and A-3 reading frames. Assuming the availability of the pIN-I A-2 and A-3 plasmids, one method would involve inserting the lac promoter-operator fragment into plasmids pKEN039 and pKEN040 in the same manner as shown in FIG. 27 and described hereinabove in connection with plasmid pKEN037. An alternative and preferable method merely requires transferring the smaller Xba I-Eco RI fragments of pKEN039 and pKEN040 into the Xba I-Eco RI site of pKEN045, in a manner analogous to that described hereinabove in connection with FIG. 15, to yield plasmids pKEN049 (pIN-II, A-2) and pKEN050 (pIN-II, A-3).

On the other hand, assuming that the corresponding constitutive plasmids are not already constructed, inducible plasmids pKEN049 (A-2) and pKEN050 (A-3) can be derived directly from plasmid pKEN045 (A-1). Specifically, the DNA sequence in the vicinity of the Eco RI cleavage site of pKEN045 can itself be modified according to the scheme shown in FIG. 13, lines b and c, or the scheme illustrated in FIG. 14, lines b and c, to yield directly the structure of plasmids pKEN049 (A-2) or pKEN050 (A-3), respectively. This is the most preferred method of constructing these plasmids, since it does not require as a condition precedent the construction of the corresponding constitutive plasmids.

There are also several options available in constructing pIN-II plasmids incorporating the B and C insertion sites. Assuming again that the corresponding pIN-I plasmids have already been constructed, each could be modified to insert the lac promoter-operator fragment, according to the procedure of FIG. 27, or more preferably, the smaller Xba I-Eco RI fragment of pKEN045 (pIN-II, A-1) could be replaced successively with the smaller Xba I-Eco RI fragments from each of the constitutive B site and C site plasmids, yielding, in either case, pIN-II plasmids according to Table I.

TABLE I

| Insertion Site | Reading Frame | pIN-I Plasmids | pIN-II Plasmids |
|---|---|---|---|
| B | 1 | pKEN041 | pKEN051 |
|   | 2 | pKEN047 | pKEN052 |
|   | 3 | pKEN048 | pKEN053 |
| C | 1 | pKEN042 | pKEN054 |
|   | 2 | pKEN043 | pKEN055 |
|   | 3 | pKEN044 | pKEN056 |

Most preferably, however, the pIN-II expression plasmids are constructed without first making the corresponding pIN-I plasmids. In the case of the B insertion site, plasmid pKEN051 (pIN-II, B-1) can be derived from plasmid pKEN221 by first digesting pKEN221 plasmid DNA with Fnu4H-I restriction enzyme and then attaching Eco RI cohesive termini to the ends of the resulting fragment, according to the procedure described hereinabove and illustrated schematically at 138 in FIG. 17. The Eco RI fragment thus obtained can then be digested by Xba I restriction enzyme, splitting the fragment in two at the Xba I cleavage site located within the 5'-untranslated region. By purifying the smaller Xba I-Eco RI fragment thus obtained, and substituting it for the smaller Xba I-Eco RI fragment of pKEN045 (pIN-II, A-1), the B-1 inducible cloning vehicle can be obtained. The resulting plasmid, pKEN051 (pIN-II, B-1), can then be further modified according to the scheme illustrated schematically at 141 in FIG. 18 and in FIG. 19, or according to the scheme shown schematically at 142 in FIG. 18 and in FIG. 20, to yield the pIN-II plasmids corresponding to the B-2 and B-3 reading frames, pKEN052 and pKEN053, respectively.

An analogous course can be followed to obtain the pIN-II C site plasmids directly, without first constructing the corresponding pIN-I plasmids. Specifically, after digestion of pKEN111 plasmid DNA with Sau 3A restriction enzyme and attachment of Eco RI cohesive termini to the ends of the resulting fragment (according to the procedure described hereinabove and illustrated at 145 in FIG. 22), the Eco RI fragment thus obtained can then be digested with Xba I restriction enzyme, splitting the fragment in two at the Xba I cleavage site (located within the 5'-untranslated region). The Xba I-Eco RI fragment carrying the signal peptide region can then be inserted into the Xba I-Eco RI site of pKEN045, resulting in the plasmid pKEN054 (pIN-II, C-1). Further modification of the pKEN054 DNA according to the procedure shown schematically at 148 in FIG. 23 and in FIG. 24, or according to the procedure illustrated schematically at 149 in FIG. 23 and in FIG. 25, yields the pIN-II plasmids corresponding to the C-2 and C-3 reading frames, pKEN055 and pKEN056, respectively.

E. Construction Of Auto-Regulated Inducible Expression (pIN-III) Plasmids

Figure 28:
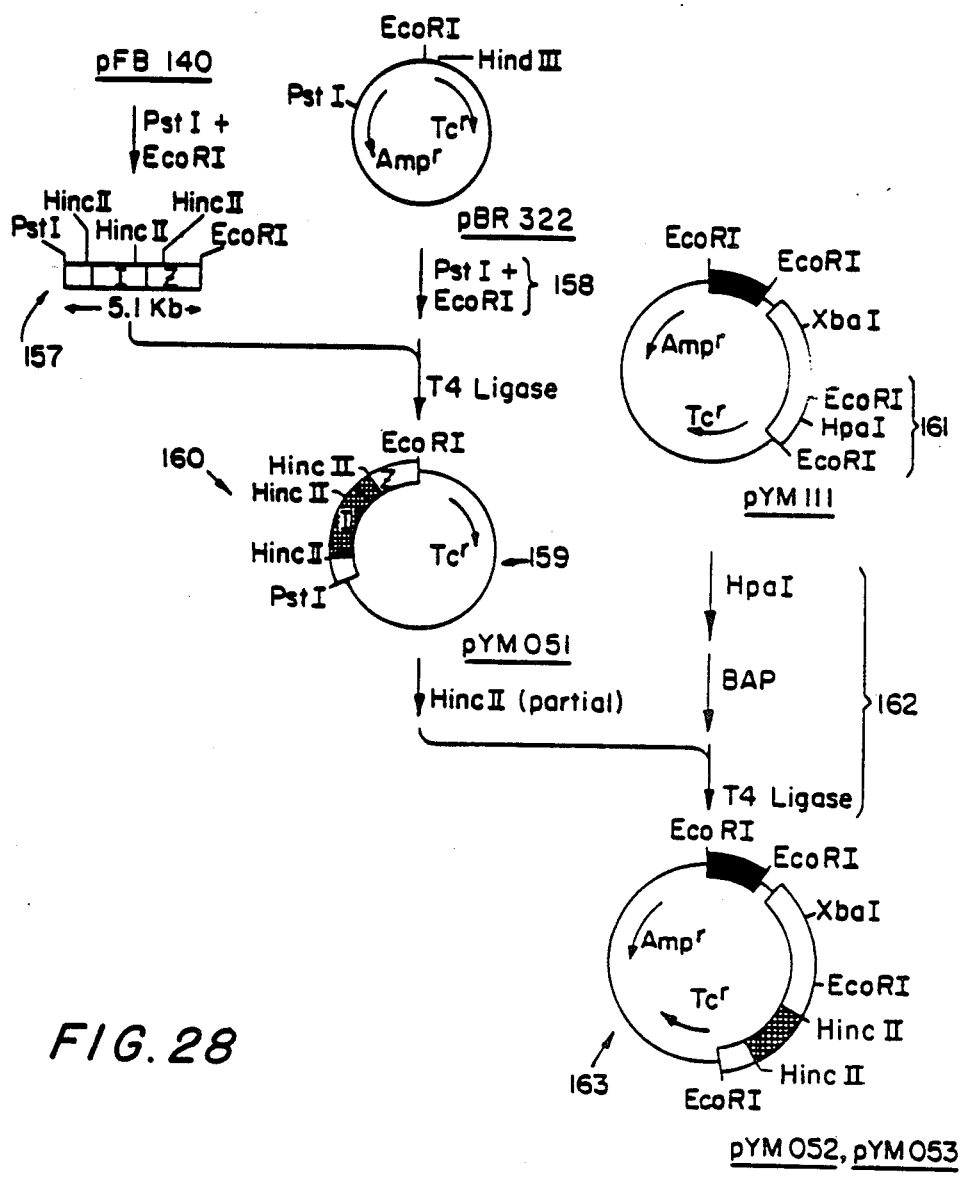

FIGS. 28 and 29 schematically illustrate the manner in which the lacI gene was added to the inducible A-1 plasmid cloning vehicle of the pIN-II series, yielding the corresponding auto-regulated inducible expression plasmid of the pIN-III series. The specific steps in this procedure are described in detail hereinbelow.

1. Construction Of Plasmid pYM051

The first step in the construction of the A-1 expression plasmid of the pIN-III series was to clone the lacI gene into pBR322. In order to accomplish this result, a 5.1 Kb DNA fragment containing the lacI gene was first derived from plasmid pFB140 (obtained from Monica Riley of the Department of Biochemistry, State University of New York at Stony Brook) as follows: 15 micrograms of pFB140 plasmid DNA were digested with 80 units Eco RI restriction enzyme in 200 microliters of Eco RI buffer at 37° C. for 2 hours. The reaction mixture was extracted with phenol and the DNA fragments were precipitated with 2.5 volumes of ethanol and dried under vacuum. The DNAs were then digested to completion with 12 units of Pst I restriction endonuclease in 300 microliters of a reaction mixture containing 6 mM Tris:HCl (pH 7.5), 6 mH MgCl2, 50 mH NaCl, 6 mM $\beta$-mercaptoethanol and 100 micrograms/ml BSA (this reaction mixture will hereinafter be referred to as a "Pst I buffer") at 37° C. for 2 hours. A 5.1 Kb Pst I-Eco RI fragment carrying the lacI gene (illustrated schematically at 157 in FIG. 28) was purified by agarose gel electrophoresis: the DNA fragments in the agarose gel were stained with ethidium bromide (one microgram/ml), and the band corresponding to the 5.1 Kb fragment was cut out. The DNA fragments in this band were eluted from the gel after freezing. Ethidium bromide was removed from the DNA fragments by phenol extraction, and the DNAs were recovered by ethanol precipitation.

In order to clone the 5.1 Kb Pst I-Eco RI fragment containing the lacI gene into pBR322, the smaller DNA fragments lying between the Pst I and Eco RI cleavage sites of pBR322 was first deleted, as shown schematically at 158 in FIG. 28, using the following procedure: 10 micrograms of pBR322 DNA were digested with 2 units of Pst I restriction enzyme in 100 microliters of Pst I buffer at 37° C. for 3 hours. After phenol extraction and ethanol precipitation, the DNAs were dried under vacuum, and then digested with 80 units of Eco RI restriction enzyme in a total volume of 200 microliters of Eco RI buffer at 37° C. for 2 hours. The larger Pst I-Eco RI fragments, consisting of approximately 3.7 Kb, were then purified by agarose gel electrophoresis.

The purified fragments (0.07 micrograms) were then mixed with 0.1 micrograms of the previously-obtained 5.1 Kb pFB140 fragments, and the Pst I and Eco RI cohesive termini were ligated by treating with 20 units of T4 DNA ligase (obtained from New England Biolabs) in 25 microliters of ligase buffer containing 0.48 mM ATP at 12.5° C. for 16 hours. Fifteen microliters of the ligated mixture were used to transform E. coli strain W620 recA, NRRL B-15024 (F−, thi-1, pyrD36, gltA6, galK30, strA129λ−, supE44). This strain is available to the public from the permanent collection of the Northern Regional Research Laboratory, U.S. Department of Agriculture, Peoria, Ill., U.S.A., and was derived from E. coli strain W620, obtained from the Department of Human Genetics, Yale University, School of Medicine. One of the plasmid DNAs purified from tetracycline-resistant transformants had the structure shown at 159 in FIG. 28. This plasmid was designated pYM051, and is obtainable from E. coli W620 recA/pYM051, NRRL B-15025, which is available to the public from the permanent collection of the Northern Regional Research Laboratory, U.S. Department of Agriculture, Peoria, Ill., U.S.A. The plasmid can be obtained from NRRL B-15025 by conventional means.

2. Construction Of Plasmids pYM052 AND pYM053

Plasmid pYM051 carries a 5.1 Kb Pst I-Eco RI DNA fragment containing not only the lacI gene, but also a substantial portion of the lacZ gene. As shown at 160 in FIG. 28, this fragment contains three Hinc II cleavage sites in the vicinity of the lacI gene, two of which surround or "bracket" the lacI gene, and one of which falls within the lacI gene itself. In order to shorten this 5.1 Kb DNA fragment and at the same time retain the lacI gene intact for later use, the following procedure was used: 5 micrograms of pYM051 plasmid DNA were partially digested with 0.32 units of Hinc II restriction enzyme in 75 microliters of Hind III buffer at 37° C. for 1 hour. After phenol extraction and ethanol precipitation, the DNAs were dried under vacuum. This procedure yielded DNA fragments of varying of lengths, one of which (1.7 Kb in length—shown schematically by the vertical and horizontal cross-hatching at 160 in FIG. 28 and similarly in FIGS. 29–31B and 33) carries an intact lacI gene.

In order to provide a vehicle to carry the shortened DNA fragment bearing the lacI gene, a plasmid designated pYM111 was constructed. This plasmid is obtainable from E. coli JA221/F'lacIq/pYM111, NRRL B-15038, which is available to the public from the permanent collection of the Northern Regional Research Laboratory, U.S. Department of Agriculture, Peoria, Ill., U.S.A. The plasmid can be obtained from NRRL B-15038 by conventional means.

As shown schematically at 161 in FIG. 28, pYM111 includes a Hpa I cleavage site surrounded in relatively close proximity by two Eco RI cleavage sites. This plasmid is an acceptable recipient for the lacI gene fragment because it is a member of the class of plasmids having the following characteristics: (1) it contains a unique restriction enzyme cleavage site (i.e., a site occurring only once within the plasmid) which preferably yields blunt end termini, such as Hpa I, Hinc II or Pvu II; (2) it is derived from pBR322, and the unique cleavage site is not located within the DNA sequence responsible for the replication of the plasmid itself; (3) it also contains two cleavage sites which surround the unique cleavage site and are located within approximately 400–700 base pairs of the unique cleavage site, the two surrounding cleavage sites preferably being recognizsplitting the fragment in two at the Xba I cleavage site (located within the 5'-untranslated region). The Xba I-Eco RI fragment carrying the signal peptide region can then be inserted into the Xba I-Eco RI site of pKEN045, resulting in the plasmid pKEN054 (pIN-II, C-1). Further modification of the pKEN054 DNA according to the procedure shown schematically at 148 in FIG. 23 and in FIG. 24, or according to the procedure illustrated schematically at 149 in FIG. 23 and in FIG. 25, yields the pIN-II plasmids corresponding to the C-2 and C-3 reading frames, pKEN055 and pKEN056, respectively.

E. Construction Of Auto-Regulated Inducible Expression (pIN-III) Plasmids

FIGS. 28 and 29 schematically illustrate the manner in which the lacI gene was added to the inducible A-1 plasmid cloning vehicle of the pIN-II series, yielding the corresponding auto-regulated inducible expression plasmid of the pIN-III series. The specific steps in this procedure are described in detail hereinbelow.

1. Construction Of Plasmid pYM051

The first step in the construction of the A-1 expression plasmid of the pIN-III series was to clone the lacI gene into pBR322. In order to accomplish this result, a 5.1 Kb DNA fragment containing the lacI gene was first derived from plasmid pFB140 (obtained from Monica Riley of the Department of Biochemistry, State University of New York at Stony Brook) as follows: 15 micrograms of pFB140 plasmid DNA were digested with 80 units Eco RI restriction enzyme in 200 microliters of Eco RI buffer at 37° C. for 2 hours. The reaction mixture was extracted with phenol and the DNA fragments were precipitated with 2.5 volumes of ethanol and dried under vacuum. The DNAs were then digested to completion with 12 units of Pst I restriction endonuclease in 300 microliters of a reaction mixture containing 6 mM Tris:HCl (pH 7.5), 6 mH MgCl2, 50 mH NaCl, 6 mM β-mercaptoethanol and 100 micrograms/ml BSA (this reaction mixture will hereinafter be referred to as a "Pst I buffer") at 37° C. for 2 hours. A 5.1 Kb Pst I-Eco RI fragment carrying the lacI gene (illustrated schematically at 157 in FIG. 28) was purified by agarose gel electrophoresis: the DNA fragments in the agarose gel were stained with ethidium bromide (one microgram/ml), and the band corresponding to the 5.1 Kb fragment was cut out. The DNA fragments in this band were eluted from the gel after freezing. Ethidium bromide was removed from the DNA fragments by phenol extraction, and the DNAs were recovered by ethanol precipitation.

In order to clone the 5.1 Kb Pst I-Eco RI fragment containing the lacI gene into pBR322, the smaller DNA fragments lying between the Pst I and Eco RI cleavage sites of pBR322 was first deleted, as shown schematically at 158 in FIG. 28, using the following procedure: 10 micrograms of pBR322 DNA were digested with 2 units of Pst I restriction enzyme in 100 microliters of Pst I buffer at 37° C. for 3 hours. After phenol extraction and ethanol precipitation, the DNAs were dried under vacuum, and then digested with 80 units of Eco RI restriction enzyme in a total volume of 200 microliters of Eco RI buffer at 37° C. for 2 hours. The larger Pst I-Eco RI fragments, consisting of approximately 3.7 Kb, were then purified by agarose gel electrophoresis.

The purified fragments (0.07 micrograms) were then mixed with 0.1 micrograms of the previously-obtained 5.1 Kb pFB140 fragments, and the Pst I and Eco RI cohesive termini were ligated by treating with 20 units of T4 DNA ligase (obtained from New England Biolabs) in 25 microliters of ligase buffer containing 0.48 mM ATP at 12.5° C. for 16 hours. Fifteen microliters of the ligated mixture were used to transform *E. coli* strain W620 recA, NRRL B-15024 (F−, thi-1, pyrD36, gltA6, galK30, strA129λ−, supE44). This strain is available to the public from the permanent collection of the Northern Regional Research Laboratory, U.S. Department of Agriculture, Peoria, Ill., U.S.A., and was derived from *E. coli* strain W620, obtained from the Department of Human Genetics, Yale University, School of Medicine. One of the plasmid DNAs purified from tetracycline-resistant transformants had the structure shown at 159 in FIG. 28. This plasmid was designated pYM051, and is obtainable from *E. coli* W620 recA/pYM051, NRRL B-15025, which is available to the public from the permanent collection of the Northern Regional Research Laboratory, U.S. Department of Agriculture, Peoria, Ill., U.S.A. The plasmid can be obtained from NRRL B-15025 by conventional means.

2. Construction Of Plasmids pYM052 AND pYM053

Plasmid pYM051 carries a 5.1 Kb Pst I-Eco RI DNA fragment containing not only the lacI gene, but also a substantial portion of the lacZ gene. As shown at 160 in FIG. 28, this fragment contains three Hinc II cleavage sites in the vicinity of the lacI gene, two of which surround or "bracket" the lacI gene, and one of which falls within the lacI gene itself. In order to shorten this 5.1 Kb DNA fragment and at the same time retain the lacI gene intact for later use, the following procedure was used: 5 micrograms of pYM051 plasmid DNA were partially digested with 0.32 units of Hinc II restriction enzyme in 75 microliters of Hind III buffer at 37° C. for 1 hour. After phenol extraction and ethanol precipitation, the DNAs were dried under vacuum. This procedure yielded DNA fragments of varying of lengths, one of which (1.7 Kb in length—shown schematically by the vertical and horizontal cross-hatching at 160 in FIG. 28 and similarly in FIGS. 29–31B and 33) carries an intact lacI gene.

In order to provide a vehicle to carry the shortened DNA fragment bearing the lacI gene, a plasmid designated pYM111 was constructed. This plasmid is obtainable from *E. coli* JA221/F'lacI$^q$/pYM111, NRRL B-15038, which is available to the public from the permanent collection of the Northern Regional Research Laboratory, U.S. Department of Agriculture, Peoria, Ill., U.S.A. The plasmid can be obtained from NRRL B-15038 by conventional means.

As shown schematically at 161 in FIG. 28, pYM111 includes a Hpa I cleavage site surrounded in relatively close proximity by two Eco RI cleavage sites. This plasmid is an acceptable recipient for the lacI gene fragment because it is a member of the class of plasmids having the following characteristics: (1) it contains a unique restriction enzyme cleavage site (i.e., a site occurring only once within the plasmid) which preferably yields blunt end termini, such as Hpa I, Hinc II or Pvu II; (2) it is derived from pBR322, and the unique cleavage site is not located within the DNA sequence responsible for the replication of the plasmid itself; (3) it also contains two cleavage sites which surround the unique cleavage site and are located within approximately 400–700 base pairs of the unique cleavage site, the two surrounding cleavage sites preferably being recogniz- 0.4 units of T4 DNA ligase in 20 microliters of ligase buffer containing 0.4 mM ATP at 12.5° C. for 16 hours to anneal the Xba I cohesive termini, thereby re-circularizing the plasmid. Ten microliters of the ligated mixture was used to transform E. coli JA221/F'lacI$^q$, NRRL B-15015, which was constructed by transferring the F' factor from X90/F'lacI$^q$ lac+ pro+ (obtained from Dr. J. Beckwith, Dept. of Biochemistry and Molecular Biology, Harvard University) into E. coli strain JA221, NRRL B-15014. E. coli strain JA221/F'lacI$^q$ is available to the public from the permanent collection of the Northern Regional Research Laboratory, U.S. Department of Agriculture, Peoria, Ill., U.S.A. Upon restriction enzyme analysis of the plasmid DNAs isolated from ampicillin-resistant transformants by the rapid alkaline denaturation method, one of them was found to contain one copy of the 95 bp Alu I fragment inserted at the Xba I site of pKEN037 in the correct orientation, as shown at 153 in FIG. 27, and this plasmid was designated pKEN038.

In order to simplify the construction of inducible plasmids containing the B and C insertion sites, it was first necessary to remove one of the two Xba I cleavage sites in pKEN038 surrounding the lac promoter-operator fragment. The Xba I cleavage site located upstream of the lac promoter-operator fragment was eliminated as shown schematically at 154 in FIG. 27. This was carried out utilizing the fact that attachment of the Xba I linker to the 95 bp lac promoter-operator fragment, as described in the preceding paragraph, resulted in the creation of a new Sst I cleavage site only at the upstream end of the lac promoter, but not at the downstream end. As shown at 155 in FIG. 27, the recognition sequence of the Sst I restriction enzyme overlaps with that of the Xba I enzyme. Thus, the deletion of the 4-base "sticky end" of the Sst I cleavage site using S1 nuclease should result in the deletion of part of the Xba I recognition sequence as well, effectively eliminating the Xba I cleavage site.

In order to accomplish this result, five micrograms of pKEN038 plasmid DNA were digested with 10 units of Sst I restriction endonuclease in 50 microliters of Bam HI buffer, and treated with 500 units of S1 nuclease in 200 microliters of S1 buffer at 20° C. for one hour. Blunt ends were joined by treatment of 0.5 micrograms of the S1-treated DNA with 5 units of T4 DNA ligase in 10 microliters of ligase buffer containing 0.6 mM ATP at 12.5° C. for 16 hours. Five microliters of the ligated mixture were used to transform E. coli strain JA221/F-'lacI$^q$, NRRL B-15015. A plasmid having the structure shown schematically at 156 in FIG. 27 was isolated after restriction enzyme analysis of the plasmid DNAs obtained from ampicillin-resistant transformants by the rapid alkaliine denaturation method, and that plasmid was designated pKEN045 (pIN-II, A-1).

There are several methods available with which to construct pIN-II plasmids corresponding to the A-2 and A-3 reading frames. Assuming the availability of the pIN-I A-2 and A-3 plasmids, one method would involve inserting the lac promoter-operator fragment into plasmids pKEN039 and pKEN040 in the same manner as shown in FIG. 27 and described hereinabove in connection with plasmid pKEN037. An alternative and preferable method merely requires transferring the smaller Xba I-Eco RI fragments of pKEN039 and pKEN040 into the Xba I-Eco RI site of pKEN045, in a manner analogous to that described hereinabove in connection with FIG. 15, to yield plasmids pKEN049 (pIN-II, A-2) and pKEN050 (pIN-II, A-3).

On the other hand, assuming that the corresponding constitutive plasmids are not already constructed, inducible plasmids pKEN049 (A-2) and pKEN050 (A-3) can be derived directly from plasmid pKEN045 (A-1). Specifically, the DNA sequence in the vicinity of the Eco RI cleavage site of pKEN045 can itself be modified according to the scheme shown in FIG. 13, lines b and c, or the scheme illustrated in FIG. 14, lines b and c, to yield directly the structure of plasmids pKEN049 (A-2) or pKEN050 (A-3), respectively. This is the most preferred method of constructing these plasmids, since it does not require as a condition precedent the construction of the corresponding constitutive plasmids.

There are also several options available in constructing pIN-II plasmids incorporating the B and C insertion sites. Assuming again that the corresponding pIN-I plasmids have already been constructed, each could be modified to insert the lac promoter-operator fragment, according to the procedure of FIG. 27, or more preferably, the smaller Xba I-Eco RI fragment of pKEN045 (pIN-II, A-1) could be replaced successively with the smaller Xba I-Eco RI fragments from each of the constitutive B site and C site plasmids, yielding, in either case, pIN-II plasmids according to Table I.

TABLE I

| Insertion Site | Reading Frame | pIN-I Plasmids | pIN-II Plasmids |
|---|---|---|---|
| B | 1 | pKEN041 | pKEN051 |
|   | 2 | pKEN047 | pKEN052 |
|   | 3 | pKEN048 | pKEN053 |
| C | 1 | pKEN042 | pKEN054 |
|   | 2 | pKEN043 | pKEN055 |
|   | 3 | pKEN044 | pKEN056 |

Most preferably, however, the pIN-II expression plasmids are constructed without first making the corresponding pIN-I plasmids. In the case of the B insertion site, plasmid pKEN051 (pIN-II, B-1) can be derived from plasmid pKEN221 by first digesting pKEN221 plasmid DNA with Fnu4H-I restriction enzyme and then attaching Eco RI cohesive termini to the ends of the resulting fragment, according to the procedure described hereinabove and illustrated schematically at 138 in FIG. 17. The Eco RI fragment thus obtained can then be digested by Xba I restriction enzyme, splitting the fragment in two at the Xba I cleavage site located within the 5'-untranslated region. By purifying the smaller Xba I-Eco RI fragment thus obtained, and substituting it for the smaller Xba I-Eco RI fragment of pKEN045 (pIN-II, A-1), the B-1 inducible cloning vehicle can be obtained. The resulting plasmid, pKEN051 (pIN-II, B-1), can then be further modified according to the scheme illustrated schematically at 141 in FIG. 18 and in FIG. 19, or according to the scheme shown schematically at 142 in FIG. 18 and in FIG. 20, to yield the pIN-II plasmids corresponding to the B-2 and B-3 reading frames, pKEN052 and pKEN053, respectively.

An analogous course can be followed to obtain the pIN-II C site plasmids directly, without first constructing the corresponding pIN-I plasmids. Specifically, after digestion of pKEN111 plasmid DNA with Sau 3A restriction enzyme and attachment of Eco RI cohesive termini to the ends of the resulting fragment (according to the procedure described hereinabove and illustrated at 145 in FIG. 22), the Eco RI fragment thus obtained can then be digested with Xba I restriction enzyme, pYM061, resulting in the C-1 plasmid of pIN-III. Further modification of the plasmid DNA according to the procedure shown schematically at 148 in FIG. 23 and in FIG. 24, or according to the procedure illustrated schematically at 149 in FIG. 23 and in FIG. 25, yields the pIN-III plasmids corresponding to the C-2 and C-3 reading frames, respectively.

F. Construction Of pIN-II(113) And pIN-III(113) Expression Plasmids

FIGS. 30A and 30B together illustrate schematically the manner in which an auto-regulated inducible plasmid cloning vehicle incorporating the A insertion site in the A-3 reading frame, and also utilizing the 113 bp lac promoter-operator fragment (rather than the 95 bp lac fragment) was constructed, and may be referred to in connection with the following more particularized discussion.

1. Construction Of Plasmid pKM009

The first step in the construction of the A-3 expression plasmid of the pIN-III(113) series was to construct a plasmid to serve as a source of the 113 bp lac fragment in subsequent steps of the procedure. The plasmid chosen to receive the 113 bp lac fragment for this purpose was pKM005, a 9.9 Kb plasmid derived from pBR322 and carrying the lacZ and lacY structural genes, but no promoter with which to initiate their transcription, as shown schematically at 168 in FIG. 30A. This plasmid is obtainable from *E. coli* 4288 recA/pKM005, NRRL B-15395, which is available to the public from the permanent collection of the Northern Regional Research Laboratory, U.S. Department of Agriculture, Peoria, Ill., U.S.A. The plasmid can be obtained from NRRL B-15395 by conventional means.

The 113 bp lac promoter-operator fragment was derived from pKEN125, a 3.9 Kb plasmid which carries a rather lengthy (approximately 500 bp) portion of the natural *E. coli* lac promoter-operator region, as shown schematically at 169 in FIG. 30A. This plasmid is obtainable from *E. coli* JA221/F'lacI$^q$/pKEN125, NRRL B-15235, which is available to the public from the permanent collection of the Northern Regional Research Laboratory, U.S. Department of Agriculture, Peoria, Ill., U.S.A. The plasmid can be obtained from NRRL B-15235 by conventional means.

In order to construct the plasmid vehicle to carry the 113 bp lac fragment, the following procedure was used: 10 micrograms of pKM005 plasmid DNA were digested to completion with 20 units of Xba I restriction enzyme in 100 microliters of Bam HI buffer at 37° C. for one hour. The reaction was terminated by phenol extraction, and the linearized DNAs were recovered by ethanol precipitation.

A 190 bp Hha I fragment (shown schematically at 170 in FIG. 30A) carrying the lac promoter-operator region (illustrated schematically by the saw-toothed segment at 171 in FIG. 30A and similarly in FIGS. 30B-31B and 33), was separately derived from pKEN125 as follows: 40 micrograms of pKEN125 plasmid DNA were digested with 40 units of Hha I restriction enzyme in 302 microliters of Hind III buffer at 37° C. for 1.5 hours. The 190 bp fragment was purified by 5% polyacrylamide gel electrophoresis in the following manner: the DNA fragments in the polyacrylamide gel were stained with ethidium bromide (one microgram/ml), and the band corresponding to the 190 bp fragment was cut out. The DNA fragments in this band were eluted from the gel using electrophoresis. Ethidium bromide was removed from the DNA fragments by phenol extraction, and the DNAs were recovered by ethanol precipitation.

In order to isolate still further the DNA segment within which the lac promoter-operator resides, the following procedure (indicated schematically at 172 in FIG. 30A) was used: one-half of the purified 190 bp Hha I DNA fragments obtained were digested with 7 units of Bst NI restriction enzyme in 50 microliters of Hae III buffer at 60° C. for one hour. Phenol extraction was performed, after which the DNAs were recovered by ethanol precipitation and dried under vacuum. After digestion with Bst NI restriction enzyme, the DNAs were then treated with 4 units of Klenow enzyme (obtained from New England Nuclear) in 50 microliters of Hind III buffer in the presence of a 40 $\mu$M mixture of deoxynucleotides (dATP, dGTP, dCTP, dTTP) at room temperature for 30 minutes to create blunt ends. After phenol extraction and ethanol precipitation, the DNA fragments were mixed with 400 pmoles of phosphorylated Xba I linker, and treated with 5 units of T4 DNA ligase in ligase buffer (total volume 30 microliters) containing 0.48 mM ATP at 12.5° C. for 16 hours. The reaction was terminated by diluting the mixture twelve-fold with Bam HI buffer and by heating the mixture at 60° C. for 10 minutes. Eighty units of Xba I restriction enzyme were added, and the mixture was then incubated at 37° C. for 2 hours to create Xba I cohesive termini. This reaction was terminated by phenol extraction, and the DNAs were recovered by ethanol precipitation.

One-fortieth of the DNA mixture thus obtained was mixed with 0.4 micrograms of the previously-linearized pKM005 plasmid DNA, and the Xba I cohesive termini were ligated with 20 units of T4 DNA ligase (obtained from New England Biolabs) in ligase buffer (total volume 20 microliters) containing 0.6 mM ATP at 12.5° C. for 16 hours. Ten microliters of the ligation mixture were thereafter used to transform *E. coli* strain 4288 recA, NRRL B-15397 (recA, mal24, spc12, supE-50, DE5 [$\Delta$lac, proB]). This strain is available to the public from the permanent collection of the Northern Regional Research Laboratory, U.S. Department of Agriculture, Peoria, Ill., U.S.A. The transformants were placed on the surface of a MacConkey agar plate containing 50 micrograms/ml of ampicillin. The ampicillin-resistant transformants yielding red colonies were selected, and one of the plasmid DNAs purified from those transformants had the structure shown at 173 in FIG. 30A. This plasmid, which carried a 113 bp Xba I fragment containing the lac promoter-operator, was designated pKM009.

2. Construction of Plasmid pYM153

The next step in the construction of the pIN-III(113), A-3 expression plasmid was to clone the 113 bp lac fragment in a plasmid which already carries the lpp promoter. The plasmid chosen for this purpose was pYM151, a 12.6 Kb plasmid carrying the lpp promoter as well as the lacZ and lacY structural genes and the entire lacI gene, as shown schematically at 174 in FIG. 30A. This plasmid is obtainable from *E. coli* W620 recA/pYM151, NRRL B-15396, which is available to the public from the permanent collection of the Northern Regional Research Laboratory, U.S. Department of Agriculture, Peoria, Ill., U.S.A. The plasmid can be obtained from NRRL B-15396 by conventional means.

In order to clone the 113 bp lac fragment, the following procedure was used: 2 micrograms of pYM151 plasmid DNA were digested to completion with 20 units of Xba I restriction enzyme in 100 microliters of Bam HI buffer at 37° C. for one hour. The reaction was terminated by phenol extraction, and the linearized DNAs were recovered by ethanol precipitation. In a separate reaction, 25 micrograms of pKM009 plasmid DNA were digested with 50 units of Xba I restriction enzyme and ribonuclease A in 400 microliters of Bam HI buffer at 37° C. for two hours. The 113 bp Xba I fragment containing the lac promoter-operator region was purified by 5% polyacrylamide gel electrophoresis in the same manner as described previously, and 0.014 micrograms of the 113 bp Xba I fragment were combined with 0.2 micrograms of the previously-linearized pYM151 plasmid DNA. The Xba I cohesive termini were annealed and the plasmid thereby re-circularized by treating the mixture with 20 units of T4 DNA ligase (obtained from New England Biolabs) in ligase buffer (total volume 10 microliters) containing 1.2 mM ATP at 12.5° C. for 16 hours. Ten microliters of the ligated mixture were used to transform *E. coli* strain 4288 recA, NRRL B-15397, and the transformants were placed on the surface of an L-broth plate containing 50 micrograms/ml of ampicillin and 40 micrograms/ml of X-gal. The transformants yielding white colonies were selected, and one of the plasmids purified from the ampicillin-resistant, white-colony transformants had the structure shown at 175 in FIG. 30B. This plasmid, which was found to have undergone multiple insertion of the 113 bp Xba I lac promoter-operator fragment, was designated pYM153.

3. Construction Of Plasmid pYM071

The next step in the construction of the pIN-III, A-3 cloning vehicle was to join, in the same orientation, the region containing the tandem lpp promoter-multiple lac promoter-operator fragments, whith a DNA segment containing the other necessary and desirable features of an auto-regulated inducible lpp gene cloning vehicle, described hereinabove. These are, specifically, the polynucleotide sequence at the exogenous DNA insertion site containing the recognition sequences for the Eco RI, Bam HI and Hind III restriction enzymes, the transcription terminator fragment of the lpp gene, and the intact, functional lacI gene. The source chosen for this DNA segment was pYM061, the pIN-III, A-1 expression plasmid, the construction of which was described hereinabove, and the structure of which is depicted schematically at 176 in FIG. 30B.

In order to combine these DNA sequences, the following procedure was used: 10 micrograms of pYM061 plasmid DNA were digested with 14 units of Pst I restriction enzyme in 250 microliters of Pst I buffer at 37° C. for 1.5 hours. To this solution, 36 microliters of 1M Tris:HCl (pH 7.5), 3.75 microliters of 0.1M MgCl$_2$, 13.75 microliters of 1M NaCl, 54 microliters of H$_2$O, one microgram/ml BSA (12.5 microliters), and 50 units of Eco RI restriction enzyme were added, and the mixture was incubated at 37° C. for two hours. A 6.3 Kb Eco RI-Pst I fragment was purified by 0.7% agrose gel electrophoresis in the same manner as described previously. This fragment is illustrated schematically at 177 in FIG. 30B.

Separately, 30 micrograms of pYM153 plasmid DNA were digested with 100 units of Eco RI restriction enzyme and ribonuclease A in 250 microliters of Eco RI buffer at 37° C. for one hour and fifty minutes. The reaction mixture was extracted with phenol and the DNA fragments were precipitated with 2.5 volumes of ethanol and dried under vacuum. The DNAs were then digested with 100 units of Pst I restriction endonuclease in 250 microliters of Pst I buffer at 37° C. for two hours. A 1.3 Kb Eco RI-Pst I fragment was purified by 0.7% agarose gel electrophoresis in the same manner as described previously. This fragment is illustrated schematically at 178 in FIG. 30B. The purified 1.3 Kb fragment (0.04 micrograms) was then mixed with 0.16 micrograms of the 6.3 Kb Eco RI-Pst I fragment previously obtained from pYM061, and the Pst I and Eco RI cohesive termini were annealed by treating the mixture with 20 units of T4 DNA ligase (obtained from New England Biolabs) in 20 microliters of ligase buffer containing 0.48 mM ATP at 12.5° C. for 16 hours. Ten microliters of the ligated mixture were used to transform *E. coli* strain W620 recA, NRRL B-15024, and one of the plasmid DNAs purified from the ampicillin-resistant transformants had the structure shown at 179 in FIG. 30B. This plasmid was designated pYM071.

4. Construction Of Plasmid pYM072

The final step in the construction of the first auto-regulated inducible lpp gene cloning vehicle utilizing the 113 bp lac fragment was to eliminate the superfluous multiple 113 bp Xba I insert fragments in pYM071 (each fragment carrying a copy of the lac promoter-operator), so as to leave only one such fragment in the desired position downstream of the lpp promoter and upstream of the exogenous DNA insertion site.

To accomplish this result, 20 micrograms of pYM071 plasmid DNA were partially digested with 10 units of Xba I restriction enzyme in 100 microliters of Bam HI buffer at 37° C. for 40 minutes. The resulting Xba I fragments were purified by agarose gel electrophoresis in the same manner as described previously in order to obtain only those fragments with sizes in the range of approximately 7.4 Kb to 7.6 Kb. Since digestion with Xba I restriction enzyme results in the production of fragments with "sticky ends" at both termini, the purified DNA fragments (0.3 micrograms) were then treated with 4 units of Klenow enzyme in 75 microliters of Hind III buffer in the presence of a 5M mixture of deoxynucleotides (dATP, dGTP, dCTP, dTTP) at room temperature for 30 minutes to create blunt ends. Phenol extraction was performed and th DNAs were then recovered by ethanol precipitation.

The DNA fragments were blunt-end ligated and thereby re-circularized by treating with 2.5 units of T4 DNA ligase in 10 microliters of ligase buffer containing 0.6 mM ATP at 12.5° C. for 16 hours. Ten microliters of the ligated mixture were then used to transform *E. coli* strain W620 recA, NRRL-15024, and the transformants were placed on the surface of L-broth plates containing 50 micrograms/ml of ampicillin. Twenty-four colonies were picked up, their plasmid DNAs were isolated, and restriction maps of those plasmids were examined. Two of them had the structure shown at 180 in FIG. 30B, and these plasmids were designated pYM072. Analysis of the DNA nucleotide sequence of pYM072 confirmed that this plasmid was the pIN-III(113), A-3 auto-regulated inducible cloning vehicle.

G. Construction of pIN-III-ompA Secretion Vectors

Figure 31A:
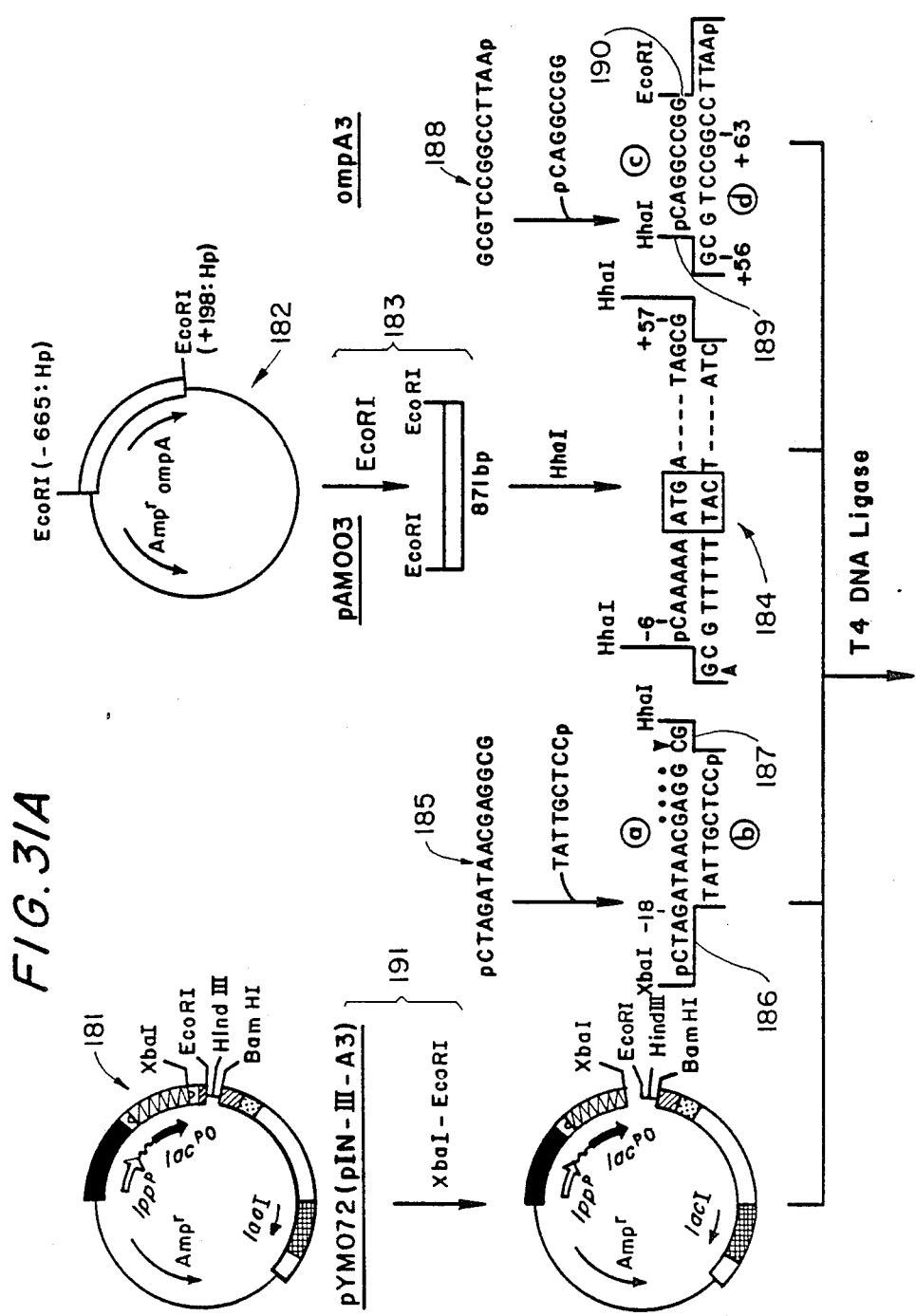

FIGS. 31A and 31B together comprise a schematic illustration of the manner in which an auto-regulated inducible expression plasmid of the pIN-III(113) series ws modified to incorporate the DNA fragment coding for the signal peptide of the E. coli ompA protein. The specific steps in this procedure are described in detail hereinbelow.

1. Construction of Plasmid pIN-III-ompA3

A described hereinabove, plasmid pYM072 is an auto-regulated inducible expression vector, incorporating the A insertion site in the A-3 reading frame, which utilizes the 113 bp lac promoter-operator fragment. This plasmid was chosen for conversion into a secretion vector utilizing the ompA signal peptide, As shown at 181 in FIG. 31A, plasmid pYM072 carries unique Xba I and Eco RI restriction enzyme cleavage sites. The 27 bp DNA fragment lying between these two cleavage sites was deleted and replaced with a DNA fragment carrying the coding region for the ompA signal peptide.

In order to accomplish this result, an 871 bp DNA fragment containing the entire ompA gene was first derived from plasmid pAM003, which is illustrated schematically at 182 in FIG. 31A. This plasmid is obtainable from E. coli JA221/pAM003, NRRL B-15769, which is available to the public from the permanent collection of the Northern Regional Research Laboratory, U.S. Department of Agriculture, Peoria, Ill., U.S.A. The plasmid can be obtained from NRRL B-15769 by conventional means.

As shown schematically at 183 in FIG. 31A, the 871 bp DNA fragment encompassing the entire ompA gene was derived from pAM003 by digesting the pAM003 plasmid DNA with Eco RI restriction enzyme, and purifying the resulting 871 bp fragment using the recovery techniques described hereinabove. Thereafter, in order to isolate still further the DNA segment containing the ompA signal peptide, the 871 bp Eco RI fragment was digested with Hha I restriction endonuclease, and was isolated using the conventional recovery techniques.

As shown schematically at 184 in FIG. 31A, the 65 bp Hha I fragment encompasses the region from nucleotide $-8$ to $+57$ of the ompA gene (for present purposes, $+1$ has been defined to correspond to the A residue of the translation initiation codon, ATG, rather than the transcription initiation site, of the ompA gene). Thus, the 65 bp Hha I fragment carries the DNA coding for the first 19 amino acid residues of the secretory precursor, proompA; this DNA therefore codes for 19 out of the 21 amino acid residues needed for the complete ompA signal peptide.

Referring again to plasmid pYM072 as shown at 181 in FIG. 31A, it will be appreciated that the DNA segment being deleted (located between the Xba I and Eco RI cleavage sites) includes a portion of the 5'-untranslated region of the lpp gene. This portion contains at least one of the two possible ribosome binding sites carried on the lpp gene. Since this DNA segment is to be excised, it is advantageous to recreate a ribosome binding site on the DNA fragment supplanting it, so as not to sacrifice the efficiencies in translation which are thought to result from having two possible ribosome binding sites in the mRNA transcript.

In order to accomplish this result, the Shine-Dalgarno sequence for ribosome binding was reconstructed and tailored for incorporation immediately upstream of the 65 bp Hha I fragment, using two synthetic oligonucleotides. As shown at 185 in FIG. 31A, oligonucleotide "a" consists of fifteen nucleotides and contains the Shine-Dalgarno sequence GAGG (dotted sequence in FIG. 31A). Moreover, the 6-nucleotide sequence GATAAC upstream of the Shine-Dalgarno sequence is identical to that in the ompA gene. Thus, oligonucleotide "a" reproduces the DNA sequence identical to the natural ompA gene, at least as far upstream as nucleotide $-18$. Oligonucleotide "b" is complementary to nucleotide "a," and the hybrid between nucleotides "a" and "b" creates an Xba I sticky end at the 5'-end (shown schematically at 186 in FIG, 31A) and a Hha I sticky end at the 3'-end (187 in FIG. 31A).

In a similar fashion, the DNA sequence coding for the cleavage site region of the ompA signal peptide was constructed and tailored for incorporation immediately downstream of the 65 bp Hha I fragment, using two other synthetic oligonucleotides. Oligonucleotide "d" (illustrated at 188 in FIG. 31A) consists of fourteen nucleotides and corresponds to the natural ompA DNA sequence from nucleotide $+56$ to $+63$, which codes for the amino acid sequence -Ala$^{19}$-Gln-Ala$^{21}$, with the alanine residue at position 21 being the carboxy terminal amino acid residue of the ompA signal peptide at which cleavage occurs. In order to construct an Eco RI site immediately after the signal peptide cleavage site in reading frame 3, the nucleotide sequence 3'CCTTAA5' was added after nucleotide $+63$. This sequence corresponds to 5'GGAATT3' in the sense strand, which codes for Gly-Ile. Oligonucleotide "c" consists of 8 bases, and when the complementary hybrid is formed with oligonucleotide "d," a Hha I sticky end and an Eco RI sticky end are created at the 5'-end and the 3'-end, respectively (as shown schematically at 189 and 190, respectively, in FIG. 31A).

Complementary oligonucleotides "a" and "b" were annealed by mixing 0.4 micromoles of each oligonucleotide in 100 microliters of a solution containing 50 mM Tris-HCl (pH 7.5) and 10 mM MgCl$_2$, and incubating the mixture at 100° C. for 2 minutes followed by cooling at 40° C. for 2 hours. The same procedure was followed to anneal complementary oligonucleotides "c" and "d."

The pIN-III-ompA3 plasmid vector was then constructed by ligating all the fragments described above to the large linear fragment of pYM072 resulting from the double digestion of pYM072 plasmid DNA with Xba I and Eco RI restriction enzymes (as shown at 191 in FIG. 31A). Specifically, 1 picomole of each of the annealed synthetic oligonucleotides ("a"+"b" and "c"+"d") were mixed with 0.07 picomoles of the 65 bp Hha I fragment previously obtained from plasmid pAM003 and 0.008 picomoles of the previously-digested pYM072 plasmid DNA in 24 microliters of a reaction mixture containing 42 mM Tris-HCL (pH 7.5), 8.3 mM MgCl$_2$, 5 mM ATP, 10.4 mM dithiothreitol, and 4 units of T4 DNA ligase. The mixture was incubated at 12.5° C. for 16 hours, followed by transformation into E. coli strain JA221 lpp-/F'lacI$^q$. For present purposes, this strain is equivalent to E. coli strain JA221/F'lac$^q$, NRRL B-15015, and the latter strain may also be used for this transformation. The cells were grown in L broth supplemented with 50 micrograms/ml of ampicillin, and the desired transformants were identified using colony hybridization with oligonucleotides "a" and "c" as probes. The correct orientation of the fragments was determined as follows: Since the Hha I fragment from the ompA gene can be inserted in two different orientations, the transformant with the Hha I fragment in the correct orientation was selected by examining the position of the Taq I site within the Xba I-Bam HI fragment: If the Hha I fragment is inserted in the correct orientation, two fragments of different sizes are generated by Taq I digestion of the Xba I-Bam HI fragment. On the other hand, if the Hha I fragment is inserted in the wrong orientation, the Taq I digestion gives rise to two DNA fragments of almost the same size. One such transformant carrying the Hha I fragment in the correct orientation was selected and was designated pIN-III-ompA3. DNA sequencing from the Xba I site to the Bam HI site of this plasmid revealed the structure illustrated schematically at 192 in FIG. 31B. The DNA sequence coding for the ompA signal peptide and its associated ribosome binding site is represented schematically by the segment 193 containing horizontal lines in FIG. 31B, and similarly in FIG. 33. The pIN-III-ompA3 plasmid DNA had exactly the same sequence as predicted from the foregoing construction procedure, except for the loss of one G:C base pair in the upstream Hha I site as indicated by arrows in FIG. 31A. The reason for this mutation is not known at present. This mutation resulted in the loss of the upstream Hha I site, and the space between the Shine-Dalgarno sequence and the initiation codon was reduced to 7 bases, one base shorter than that of the ompA gene. However, this mutation had no demonstrable effect upon the function of the secretion vector.

2. Construction Of Other pIN-III-ompA Secretion Vectors

In order to accommodate DNA insert fragments oriented in reading frames not in phase with that of plasmid pIN-III-ommpA3, the reading fram e of this plasmid was adjusted at th Eco RI cleavage site to produce secretion vectors utilizing the ompA signal peptide and having each of the remaining reading frames. In each case, two synthetic oligonucleotides were used for this purpose.

As shown schematically at 193' in FIG. 31B, in order to construct the other two reading frames, a 77 bp Xba I-Hha I fragment was first purified from the pIN-III-ompA3 plasmid DNA using conventional techniques. In each case, this fragment was then religated along with two synthetic oligonucleotides to the large Xba I-Eco RI fragment obtained by double digestion of pIN-III-ompA3 plasmid DNA with Xba I and Eco RI restriction enzymes (indicated at 194 in FIG. 31B).

For the construction of the pIN-III-ompA1 vector (reading frame 1), complementary synthetic oligonucleotides "e" and "f" (illustrated schematically at 195 in FIG. 31B) were used. The pIN-III-ompA2 vector was also constructed in a similar fashion, with the use of complementary synthetic oligonucleotides "g" and "h" (shown schematically at 196 in FIG. 31B). Complementary oligonucleotides "e" and "f", and complementary oligonucleotides "g" and "h", were first annealed according to the same procedure used hereinabove in connection with oligonucleotides "a" and "b". The formation of the complementary hybrids between oligonucleotides "e" and "f", and between oligonucleotides "g" and "h", resulted in the reconstruction of a Hha I sticky end and an Eco RI sticky end at the 5'-end and the 3'-end, respectively, of the double-stranded hybrids (as shown schematically at 197A/197B and 198A/198B, respectively, in FIG. 31B).

Figure 32:
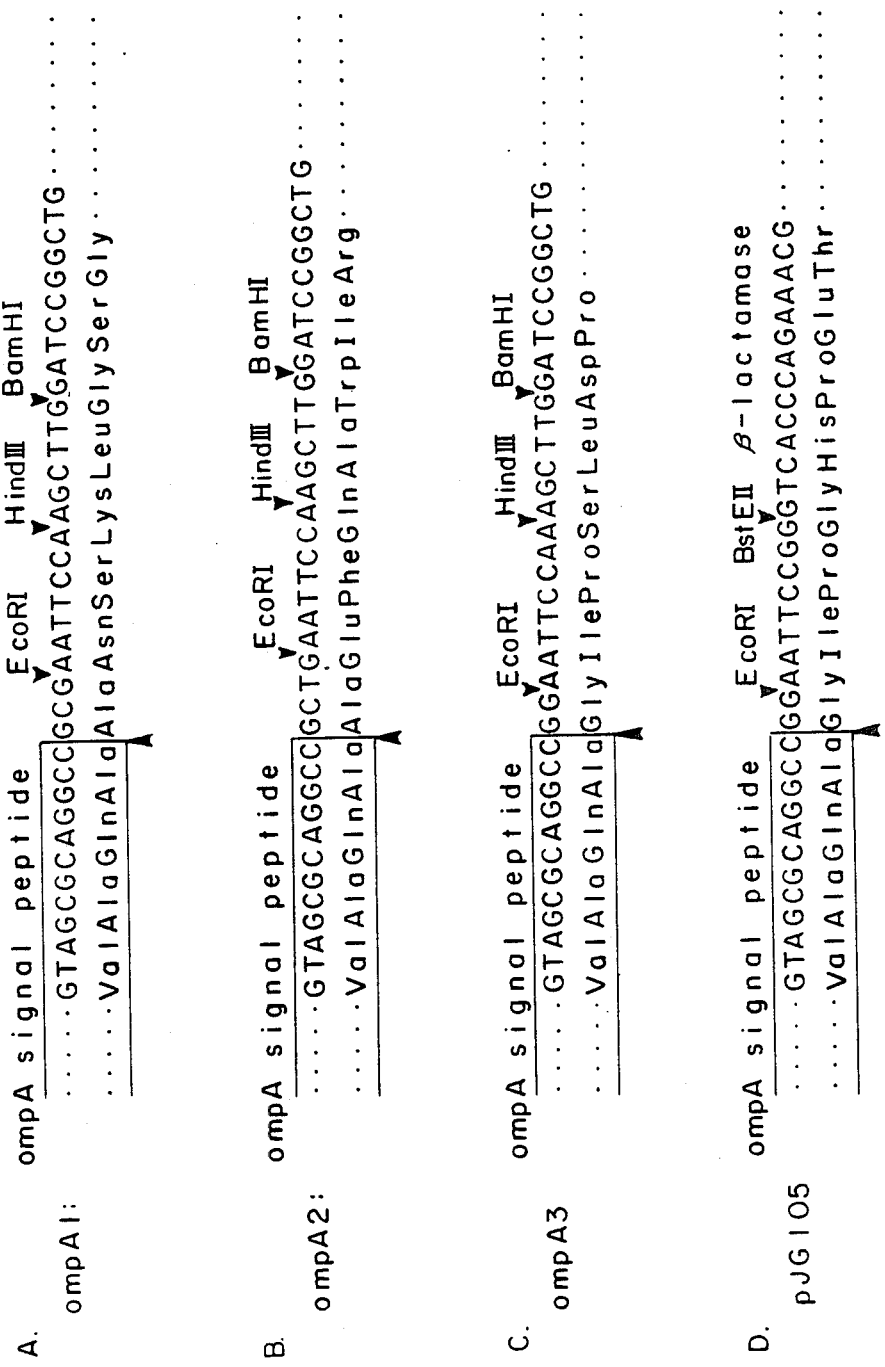

Thereafter, the various DNA fragments were ligated in a mixture containing 0.6 picomoles of the large linear DNA fragment obtained previously after double digestion of pIN-III-ompA3 plasmid DNA, 27 picomoles of the Xba I-Hha I fragment from the same vector and 20 picomoles of the annealed synthetic oligonucleotides ("e"+"f" for reading frame 1, "g"+"h" for reading frame 2) in 15 microliters of a reaction mixture containing 6.6 mM Tris-HCl (pH 7.5), 6.6 mM MgCl₂, 0.6 mM ATP, 10 mM dithiothreitol and 3 units of T4 DNA ligase. The mixture was incubated at 12.5° C. for 16 hours, and transformed into E. coli strain JA221 lpp-/F'lacI$^q$. For present purposes, this strain is equivalent to E. coli strain JA221/F'lac$^q$, NRRL B-15015, and the latter strain may also be used for this transformation. The cells were grown in L broth supplemented with 50 micrograms/ml of ampicillin. One candidate for each of the reading frames was selected, and they were found to contain three of the Hha I-Eco RI synthetic linker oligonucleotides. Plasmid DNA was then digested with Eco RI restriction enzyme, and the large linear fragments were re-circularized by treating with T4 DNA ligase and transformed once again into E. coli strain JA221 lpp-/F'lacI$^q$ (this procedure is illustrated schematically at 199 in FIG. 31B). Again, this strain is equivalent to E. coli strain JA221/F'lac$^q$, NRRL B-15015, and the latter strain may also be used for this transformation. Three transformants were picked for pIN-III-ompA1 and pIN-III-ompA2, and DNA sequencing of the Xba I-Bam HI fragments was performed, confirming the DNA sequence in the region of the signal peptide cleavage site shown for each plasmid in FIG. 32, lines A and B. The corresponding DNA sequence for pIN-III-ompA3 is also shown in FIG. 32, line C, for comparison, and the amino acid sequences for all three vectors in the region of the signal peptide cleavage site are also shown in FIG. 32.

H. Expression Of An Exogenous Gene In A Transformed Bacterial Host

THe structural gene for β-lactamase was chosen to demonstrate the expression of an exogenous gene in a transformed bacterial host in accordance with the present invention. Plasmid pIN-III-ompA3 was chosen for this purpose, as illustrated in FIG. 33.

1. Construction of pIN-III-ompA3-β-lactamase

Figure 33:
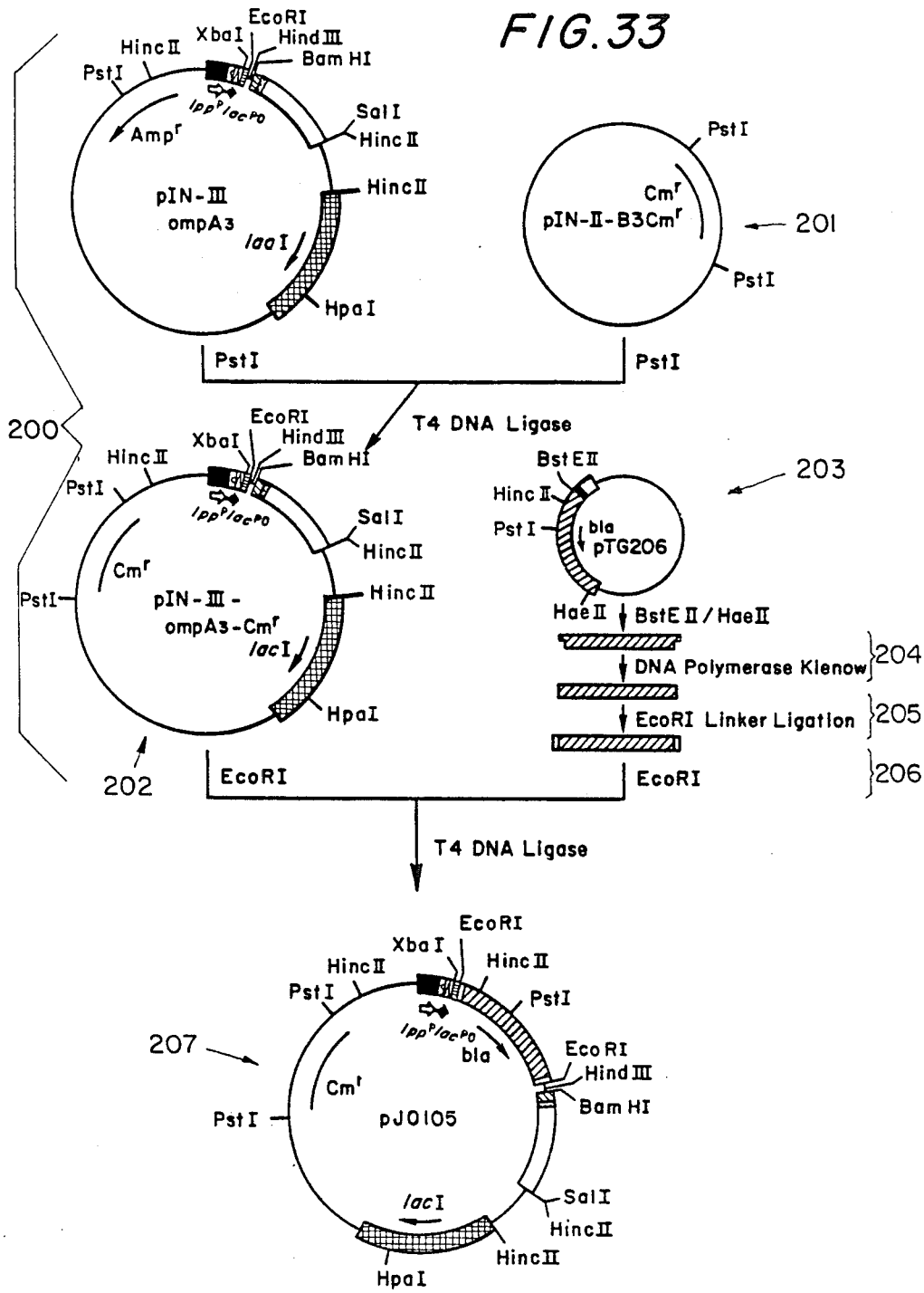
FIG. 33 schematically illustrates the manner in which a gene coding for a bacterial protein is inserted in one of the plasmid cloning vectors of the present invention, wherein Cmr denotes the gene for chloramphenicol resistance.

In order to clone the gene for β-lactamase (bla) into pIN-III-ompA3, it was necessary first to inactivate the natural bla gene in the vector itself by inserting the gene conferring chloramphenicol resistance ("Cm$^r$") into the unique Pst I site in the bla gene, as shown at 200 in FIG. 33. The chloramphenicol resistance gene was obtained from plasmid pIN-II-B3-Cm$^r$ (shown schematically at 201 in FIG. 33), and the Pst I fragment carrying the Cm$^r$ gene was inserted into the Pst I site of pIN-III-ompA3 in accordance with known techniques. After re-circularization with T4 DNA ligase, te resulting plasmid (having the structure shown at 202 in FIG. 33) was designated pIN-III-ompA3-Cm$^r$.

In order to insert into this vector only the portion of the bla gene coding for the mature protein (i.e., without its own signal peptide), plasmid pTG206 (shown schematically at 203 in FIG. 33) was first created as a source of the desired portion of the bla gene. Plasmid pTG206 was derived from the plasmid pBR322 (commercially available from Bethesda Research Laboratories) by changing the DNA sequence at the signal peptide cleavage region of the bla gene from 5'GCTCAC3' to 5'GGTCAC3' by site-specific mutagenesis using a synthetic oligonucleotide. This single base change created a Bst EII site, as shown schematically in FIG. 32, line D. Thus, digestion of pTG206 plasmid DNA with Bst EII and Hae II restriction enzymes generated a DNA fragment coding for β-lactamase without the signal peptide. Treatment of this fragment with the Klenow fragment of DNA polymerase (obtained from New England Nuclear) in the presence of deoxynucleotides (dATP, dGTP, dCTP, dTTP) filled in the 5'-end hangover sequence at the Bst EII site, and removed the 3'-end hangover sequence at the Hae II site, as shown schematically at 204 in FIG. 33. As a result, both ends of this DNA fragment became blunt-ended, to which Eco RI linkers (5'CCGGAATTCCGG3'; obtained from New England Biolabs) were ligated (shown schematically at 205 in FIG. 33). The fragment was then digested with Eco RI restriction enzyme and inserted into the Eco RI site of pIN-III-ompA3, as shown at 206 in FIG. 33.

Following transformation into *E. coli* strain JA221 1pp-/F'lacI$^q$ (*E. coli* strain JA221/F'lacI$^q$, NRRL B-15015, may also be used), transformants were initially selected by chloramphenicol resistance. Those transformants which also had the bla gene fragment in the correct orientation were then selected by their ampicillin resistance. It was found that they were ampicillin resistant even in the absence of IPTG, a lac inducer, and that they were IPTG sensitive. This indicates that even in the absence of IPTG, a small amount of β-lactamase was produced, which was at least a sufficient quantity to make the cells ampicillin-resistant, while in the presence IPTG, over-production of β-lactamase was lethal to the cells. One of the transformants selected was designated pJG105, and its DNA sequence was determined to be the same as predicted from the construction procedure, as shown in FIG. 32, line D. The structure of pJG105 is illustrated schematically at 207 in FIG. 33.

2. Expression Of The β-lactamase Gene In *E. Coli* Transformants Carrying Plasmid pJG105

When cells carrying pJG105 were grown in the presence of IPTG, a protein similar in apparent molecular weight to β-lactamase was produced and became the major product (approximately 20% of total cellular protein) after 2 hours of induction. The overproduction of the protein eventually became lethal to the cells, which appeared to be swollen and no longer rod-shaped when viewed under a microscope. The new product exhibited β-lactamase activity and could be immunoprecipitated with anti-β-lactamase serum.

In order to characterize the product further, cells carrying pJG105 were induced with IPTG for 20 minutes and labeled with [$^3$H]proline for 5 minutes. The cells were then washed, lysed and immunoprecipitated with anti-β-lactamase serum. The immunoprecipitates were subjected to sodium dodecyl sulfate polyacrylamide gel electrophoresis (SDS-PAGE), and the band corresponding to the β-lactamase product was excised from the gel and the protein was eluted and subjected to sequential Edman degradation. The only significant radioactivity appeared at positions 3 and 6, indicating that the ompA signal peptide was cleaved at its normal processing site to yield β-lactamase with an extension consisting of four amino acids (Gly-Ile-Pro-Gly) at its amino terminus (shown in FIG. 32, line D). This was further confirmed by performing the Edman degradation on samples labeled with [$^3$H]glycine, and finding that the radioactivity appeared at positions 1 and 4 as expected. The fact that no proline radioactivity appeared at the second position indicated that practically no cleavage occurred at the amino terminal end of the histidine residue, which is the normal amino terminus of β-lactamase. Furthermore, the results obtained illustrated that almost all the product was processed without any detectable accumulation of its secretory precursor.

In *E. coli*, the usual cellular locale of pBR322-encoded β-lactamase is known to be the periplasmic space. However, after induction with IPTG for 2 hours, treatment of cells carrying pJG105 with osmotic shock or lysozyme-EDTA failed to release the product into the medium. On the other hand, brief sonication followed by low speed centrifugation lead to the recovery of the majority of the product which appeared to be contaminated mainly with outer membrane proteins. Treatment of the aggregate with 0.3% sodium lauryl sarkosinate followed by high speed centrifugation lead to the solubilization of β-lactamase which was greater than 96% pure as judged by SDS-PAGE. The results indicate that overproduction of the protein leads to its aggregation in the periplasmic space. This aggregation was not due to crosslinking via the cysteine residues in β-lactamase, since migration of the product on SDS-PAGE in the absence of reducing agent was actually faster than in the presence of reducing agent. This indicated that only the normal disulfide bond of β-lactamase is formed and this provides further evidence that the β-lactamase has been translocated to the periplasmic space, since it has been shown that the disulfide bond of β-lactamase is formed after processing of pro-β-lactamase. The aggregation may simply be due to the unusually high concentration of the product, or it may be due to the presence of the amino-terminal extension of four amino acid residues, or may be conferred by the presence of the ompA signal peptide during secretion of the protein. In any event, it has been shown that the ompA signal peptide can be functional when attached to DNA sequences unrelated to the ompA protein, and that this lpp/ompA vector system can be useful for high level production of normally secreted proteins.

3. Construction of Plasmid pIN-III-ompA3-HGH1

Plasmid pIN-III-ompA3 (Example G.1) was used to construct a plasmid, designated pIN-III-ompA3-HGH1, that drives expression of human growth hormone (HGH) in *E. coli*. About 2 μg of plasmid pIN-III-ompA3 DNA were dissolved in 39 μl of 1X BamHI buffer (150 mM NaCl; 6 mM Tris-HCl, pH=7.9; 6 mM MgCl$_2$; and 100 μg/ml bovine serum albumin (BSA)), and about 1 μl (~6 units; unit definitions in this example are as defined by New England Biolabs, 32 Tozer Road, Beverly, MA 01915-9990, unless otherwise indicated) of restriction enzyme BamHI was added to the solution of DNA, and the resulting reaction was incubated at 37° C. for 1 hour. After the BamHI digestion, about 4.5 μl of 1M Tris-HCl, pH=7.2, and 0.5 μl (~5 units) of restriction enzyme EcoRI were added to the solution of BamHI-digested plasmid pIN-III-ompA3 DNA, and incubation of the reaction mixture at 37° C. was continued for another hour.

The reaction mixture was diluted with TE buffer (10 mM Tris-HCl, pH=7.4, and 1 mM EDTA) to 400 μl and then sequentially extracted with 200 μl of phenol, with 200 μl of chloroform:isoamyl alcohol (24:1), and with 400 microliters of chloroform:isoamyl alcohol (24:1). The BamHI-EcoRI-digested plasmid pIN-III-ompA3 DNA was precipitated by adding 1/20 volume of 3M LiCl and 2.5 volumes ethanol, incubating the resulting mixture at −20° C. for 20 minutes, and centrifuging to pellet the DNA. The pellet was washed with ethanol, dried, and then dissolved in 200 μl of a solution containing 50 mM Tris-HCl, pH=8.0; 1 mM MgCl₂; 0.1 mM ZnCl₂; and 20 units of calf-intestinal alkaline phosphatase (Boehringer Mannheim, 7941 Castleway Drive, P.O. Box 50816, Indianapolis, In. 46250). After incubation of the reaction mixture for 1 hour at 55° C., the DNA was separated on a 1% agarose gel. The larger (vector) fragment observed upon staining the gel with ethidium bromide and viewing the gel under long-wavelength ultraviolet light was recovered from the agarose by freezing and crushing. The aqueous material recovered was extracted and the DNA precipitated as described above. The pellet, which constituted ∼1 μg of the large EcoRI-BamHI restriction fragment of plasmid pIN-III-ompA3, and ∼0.2 μg of an ∼594 bp EcoRI-BamHI restriction fragment (in 3 μl of TE buffer) were ligated in a 20 μl reaction mixture containing 10 mM MgCl₂; 1 mM ATP; 10 mM dithiothreitol (DTT); 66 mM Tris-HCl, pH=7.6; and 1 unit of T4 DNA ligase (Bethesda Research Laboratories (BRL), Inc., P.O. Box 577, Gaithersburg, Md. 70760) that was incubated at 4° C. for 16 hours. The ∼594 bp EcoRI-BamHI restriction fragment used in the ligation encodes fur-methionyl-human growth hormone (MET-HGH) and has the structure indicated below.

deoxyoligonucleotides by procedures well known in the art. The single-stranded deoxyoligonucleotides can be synthesized with commercially available instruments, such as the ABS 380A DNA Synthesizer marketed by Applied Biosystems (850 Lincoln Centre Drive, Foster City, CA 94404). Other procedures for synthesizing DNA are also known in the art. The conventional modified phosphotriester method of synthesizing single-stranded DNA is described in Itakura et al., 1977, Science 198: 1056 and in Crea et al., 1978, Proc. Nat. Acad. Sci. USA 75: 5765. In addition, an especially preferred method of synthesizing DNA is disclosed in Hsiung et al., 1983, Nucleic Acid Research 11: 3227 and Narang et al., 1980, Methods in Enzymology 68: 90.

In addition, the ∼0.6 kb EcoRI-BamHI restriction fragment depicted above that encodes MET-HGH can be prepared by the method of Martial et al., 1979, Science 205: 602, who disclosed the cloning of much of the human growth hormone coding sequence by isolating human pituitary mRNA that comprised human growth hormone mRNA, preparing complementary DNA (cDNA) with reverse transcriptase, and inserting the cDNA into a plasmid vehicle. Goodman et al., 1979, Methods in Enzymology 68: 75, have disclosed the procedure for isolating human pituitary mRNA. Furthermore, U.S. Pat. No. 4,363,877, issued Dec. 14 1982 to Goodman et al., discloses that human growth hor-

```
*beginning of coding sequence for met-HGH
5'-AATTCTATG TTCCCAACCA TTCCCTTATC CAGGCTTTTT GACAACGCTA
   |||||    |||||||||| |||||||||| |||||||||| ||||||||||
3'-GATAC    AAGGGTTGGT AAGGGAATAG GTCCGAAAAA CTGTTGCGAT TGCTCCGCGC CCATCGTCTG CACCAGCTGG CCTTTGACAC CTACCAGGAG
|||||||||| |||||||||| |||||||||| |||||||||| ||||||||||
ACGAGGCGCG GGTAGCAGAC GTGGTCGACC GGAAACTGTG GATGGTCCTC TTTGAAGAAG CCTATATCCC AAAGGAACAG AAGTATTCAT TCCTGCAGAA
|||||||||| |||||||||| |||||||||| |||||||||| ||||||||||
AAACTTCTTC GGATATAGGG TTTCCTTGTC TTCATAAGTA AGGACGTCTT CCCCCAGACC TCCCTCTGTT TCTCAGAGTC TATTCCGACA CCCTCCAACA
|||||||||| |||||||||| |||||||||| |||||||||| ||||||||||
GGGGGTCTGG AGGGAGACAA AGAGTCTCAG ATAAGGCTGT GGGAGGTTGT GGGAGGAAAC ACAACAGAAA TCCAACCTAG AGCTGCTCCG CATCTCCCTG
|||||||||| |||||||||| |||||||||| |||||||||| ||||||||||
CCCTCCTTTG TGTTGTCTTT AGGTTGGATC TCGACGAGGC GTAGAGGGAC CTGCTCATCC AGTCGTGGCT GGAGCCCGTG CAGTTCCTCA GGAGTGTCTT
|||||||||| |||||||||| |||||||||| |||||||||| ||||||||||
GACGAGTAGG TCAGCACCGA CCTCGGGCAC GTCAAGGAGT CCTCACAGAA CGCCAACAGC CTGGTGTACG GCGCCTCTGA CAGCAACGTC TATGACCTCC
|||||||||| |||||||||| |||||||||| |||||||||| ||||||||||
GCGGTTGTCG GACCACATGC CGCGGAGACT GTCGTTGCAG ATACTGGAGG TAAAGGACCT AGAGGAAGGC ATCCAAACGC TGATGGGGAG GCTGGAAGAT
|||||||||| |||||||||| |||||||||| |||||||||| ||||||||||
ATTTCCTGGA TCTCCTTCCG TAGGTTTGCG ACTACCCCTC CGACCTTCTA GGCAGCCCCC GGACTGGGCA GATCTTCAAG CAGACCTACA GCAAGTTCGA
|||||||||| |||||||||| |||||||||| |||||||||| ||||||||||
CCGTCGGGGG CCTGACCCGT CTAGAAGTTC GTCTGGATGT CGTTCAAGCT CACAAACTCA CACAACGATG ACGCACTACT CAAGAACTAC GGGCTGCTCT
|||||||||| |||||||||| |||||||||| |||||||||| ||||||||||
GTGTTTGAGT GTGTTGCTAC TGCGTGATGA GTTCTTGATG CCCGACGAGA ACTGCTTCAG GAAGGACATG GACAAGGTCG AGACATTCCT GCGCATCGTG
|||||||||| |||||||||| |||||||||| |||||||||| ||||||||||
TGTCGAAGTC CTTCCTGTAC CTGTTCCAGC TCTGTAAGGA CGCGTAGCTC CAGTGCCGCT CTGTGGAGGG CAGCTGTGGC TTCTAGCTGC CCCCG-3'
   |||||||||| |||||||||| |||||||||| |||||||||| |||||
   GTCACGGCGA GACACCTCCC GTCGACACCG AAGATCGACG GGGGCCTAG-5',
``` wherein A is deoxyadenyl; G is deoxyguanyl; C is deoxycytidyl; and T is thymidyl. The DNA fragment depicted above can be synthesized from single-stranded mone cDNA can be isolated from plasmid pHGH-1, which was deposited in the American type Culture Collection, 12301 Parklawn Drive, Rockville, Md. 20852, under the accession number ATCC 40,000.

Human growth hormone cDNA can be used to prepare the ~0.6 kb EcoRI-BamHI restriction fragment used in the construction of plasmid pIN-III-ompA3-HGH. Once the cDNA has been cloned into a suitable plasmid vector, the ~0.6 kb EcoRI-BamHI restriction fragment depicted above can be constructed by using restriction enzymes to isolate much of the human growth hormone coding sequence and then attaching synthetic DNA linkers designed to recreate the sequence of the ~0.6 kb EcoRI-BamHI restriction fragment.

The methionyl-human growth hormone molecule encoded by the DNA fragment depicted above has the structure depicted below (beginning with the amino-terminal methionine residue):

```
              5                        10
MET PHE PRO THR ILE PRO LEU SER ARG LEU PHE 15                       20
ASP ASN ALA MET LEU ARG ALA HIS ARG LEU HIS 25                       30
GLN LEU ALA PHE ASP THR TYR GLN GLU PHE GLU 35                       40
GLU ALA TYR ILE PRO LYS GLU GLN LYS TYR SER 45                 50                 55
PHE LEU GLN ASN PRO GLN THR SER LEU CYS PHE 60                       65
SER GLU SER ILE PRO THR PRO SER ASN ARG GLU 70                       75
GLU THR GLN GLN LYS SER ASN LEU GLU LEU LEU 80                       85
ARG ILE SER LEU LEU LEU ILE GLN SER TRP LEU 90                       95
GLU PRO VAL GLN PHE LEU ARG SER VAL PHE ALA 100                105                110
ASN SER LEU VAL TYR GLY ALA SER ASP SER ASN 115                      120
VAL TYR ASP LEU LEU LYS ASP LEU GLU GLU GLY 125                      130
ILE GLN THR LEU MET GLY ARG LEU GLU ASP GLY 135                      140
SER PRO ARG THR GLY GLN ILE PHE LYS GLN THR 145                150                155
TYR SER LYS PHE ASP THR ASN SER HIS ASN ASP ASP 160                      165
ALA LEU LEU LYS ASN TYR GLY LEU LEU TYR CYS 170                      175
PHE ARG LYS ASP MET ASP LYS VAL GLU THR PHE 180                      185
LEU ARG ILE VAL GLN CYS ARG SER VAL GLU

190
              GLY SER CYS GLY PHE
``` wherein ALA is an alanine residue; ARG is an arginine residue; ASN is an asparagine residue; ASP is an aspartic acid residue; CYS is a cysteine residue; CLN is a glutamine residue; GLU is a glutamic acid residue; GLY is a glycine residue; HIS is a histidine residue; ILE is an isoleucine residue; LEU is a leucine residue; LYS is a lysine residue; MET is a methionine residue; PHE is a phenylalanine residue; PRO is a proline residue; SER is a serine residue; THR is a threonine residue; TRP is a tryptophan residue; TYR is a tyrosine residue; and VAL is a valine residue.

The ligated DNA prepared above constituted plasmid pIN-III-ompA3-HGH and was used to transform a restriction minus, modification plus strain of *E. coli* K12. One suitable such strain is *E. coli* K12 JA221, a strain that is publicly available from the American Type Culture Collection (ATCC), Rockville, MD 20852, under the accession number ATCC 33875. (JA221 is also available from the Northern Regional Research Center (NRRL), Agricultural Research Service, U.S. Department of Agriculture, Peoria, IL 61604, under the accession number NRRL B-15211.) To prepare *E. coli* K12 JA221 cells that are competent for transformation, the lyophils of *E. coli* K12 JA221 are reconstituted to isolate single colonies. One single-colony isolate of JA221 is inoculated into 5 ml of L broth (10 g of Bacto-tryptone, 10 g of NaCl, and 5 g of Bacto-Yeast Extract per liter) that contains 10 mM $MgSO_4$ and 10 mM $MgCl_2$, and the culture is incubated at 37° C. overnight with aeration. Fifty μl of the overnight culture are used to inoculate 5 ml of L broth that contains 10 mM $MgSO_4$ and 10 mM $MgCl_2$. The culture is incubated at 37° C. overnight with aeration. The following morning, the culture is diluted to 200 ml with L broth that contains 10 mM $MgSO_4$ and 10 mM $MgCl_2$. The diluted culture is incubated at 37° C. with aeration until the absorbance at 550 nm ($A_{550}$) is about 0.5, which indicates a cell density of about $1 \times 10^8$ cells/ml. The culture is cooled for ten minutes in an ice-water bath, and the cells are then collected by centrifugation at $4000 \times g$ for 10 minutes at 4° C. The cell pellet is resuspended in 100 ml of cold 10 mM NaCl and then immediately repelleted by centrifugation. The cell pellet is resuspended in 100 ml of 30 mM $CaCl_2$ and incubated on ice for 20 minutes.

The cells are again collected by centrifugation and resuspended in 10 ml of 30 mM $CaCl_2$. A one-half ml aliquot of the cells was added to the ligated DNA prepared above; the DNA had been made 30 mM in $CaCl_2$. The cell-DNA mixture was incubated on ice for one hour, heat-shocked at 42° C. for 90 seconds, and then chilled on ice for about two minutes. The cell-DNA mixture was diluted into 10 ml of L broth in a 125 ml flask and incubated at 37° C. for one hour. One hundred μl aliquots were plated on L-agar (L broth with 15 g/l agar) plates containing 100 μg/ml ampicillin, and the plates were incubated at 37° C. until colonies appeared. The colonies were individually cultured, and the plasmid DNA of the individual colonies was examined by restriction enzyme analysis and gel electrophoresis. Postive identification of the *E. coli* K12 JA221/pIN-III-ompA3-HGH transformants was based on the presence of an ~0.6 kb EcoRI-BamHI restriction fragment in the plasmid DNA of the transformants.

Once the *E. coli* K12 JA221/pIN-III-ompA3-HGH transformants were identified, plasmid pIN-III-ompA3-HGH DNA was obtained for use in subsequent constructions in accordance with the following procedure, which is adapted from Maniatis et al., 1982, *Molecular Cloning* (Cold Spring Harbor Laboratory). This same procedure was used, but on a smaller scale and with the ultracentrifugation steps replaced with phenol followed by chloroform extractions, to prepare the plasmid DNA used to identify the *E. coli* K12 JA221/pIN-III-ompA3-HGH transformants.

illustrate, the sequence around the EcoRI site in plasmid pIN-III-ompA3-HGH is depicted below:

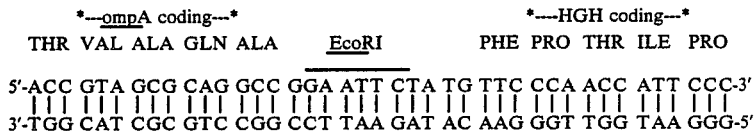

About 500 ml of stationary-phase *E. coli* cells are harvested by centrifugation at 4000×g for 10 minutes at 4° C., and the supernatant is discarded. The cell pellet is washed in 100 ml of ice-cold STE buffer (0.1M NaCl; 10 mM Tris-HCl, pH=7.8; and 1 mM EDTA). After the cell pellet is washed, the pellet is resuspended in 10 ml of Solution 1 (50 mM glucose; 25 mM Tris-HCl, pH=8.0; and 10 mM EDTA) that contains 5 mg/ml lysozyme and is left at room temperature for 10 minutes. Twenty ml of Solution 2 (0.2N NaOH and 1% SDS) are then added to the lysozyme-treated cells, and the solution is gently mixed by inversion. The mixture is incubated on ice for 10 minutes.

Fifteen ml of ice-cold, 5M potassium acetate, pH 4.8, are added to the lysed-cell mixture, and the solution is mixed by inversion. The solution is incubated on ice for 10 minutes. The 5M potassium acetate solution is prepared by adding 11.5 ml of glacial acetic acid to 28.5 ml of water and 60 ml of 5M potassium acetate; the resulting solution is 3M with respect to potassium and 5M with respect to acetate.

The lysed cell mixture is centrifuged in a Beckman SW27 rotor (or its equivalent) at 20,000 rpm for 20 minutes at 4° C. The chromosomal DNA and cell debris form a pellet on the bottom of the tube. About 36 ml of supernatant are recovered, and 0.6 volumes of isopropanol are added, mixed, and the resulting solution left at room temperature for 15 minutes. The plasmid DNA is collected by centrifugation at 12,000×g for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer.

Eight grams of CsCl are added to the DNA solution. About 0.8 ml of a 10 mg/ml solution of ethidium bromide in water are added for each 10 ml of CsCl-DNA solution. The final density of the solution is about 1.55 g/ml. The solution is transferred to a Beckman Type 50 centrifuge tube, filled to the top with paraffin oil, sealed, and centrifuged at 45,000 rpm for 24 hours at 20° C. After centrifugation, two bands of DNA are visible in ordinary light. The cap is removed from the tube, and the lower DNA band is covered using a syringe with a #21 hypodermic needle inserted through the side of the centrifuge tube.

The ethidium bromide is removed from the solution of plasmid DNA by several extractions with water-saturated 1-butanol, and the CsCl is removed by dialysis against TE buffer. After extractions with buffered phenol and then chloroform, the DNA is precipitated, washed with 70% ethanol, and dried. About 1 mg of plasmid pIN-III-ompA3-HGH was obtained and stored at 4° C. in TE buffer at a concentration of about 1 μg/ul.

Plasmid pIN-III-ompA3-HGH does not drive expression of MET-HGH in *E coli*, because the coding sequence for MET-HGH is not in frame with the coding sequence of the ompA signal peptide in the vector. To correct the reading frame, remove the methionyl residue codon, and thus construct a plasmid that will drive expression and secretion of HGH in *E. coli*, plasmid pIN-III-ompA3-HGH was subjected to oligonucleotide-directed, site-specific mutagenesis as described below.

About 30 μg of plasmid pIN-III-ompA3 DNA were dissolved in 50 μl of 1× KpnI buffer (6 mM NaCl; 6 mM Tris-HCl, pH=7.5; 6 mM MgCl$_2$; 1 mM DTT; and 100 μg/ml BSA) that contained about 50 units of restriction enzyme KpnI, and the resulting reaction was incubated at 37° C. for about 2 hours. About 1.25 μl of 5M NaCl and about 60 units of restriction enzyme XbaI were then added to the KpnI-digested plasmid pIN-III-ompA3 DNA, and the reaction mixture was again incubated at 37° C. for about 1.5 hours. The XbaI-KpnI-digested plasmid pIN-III-ompA3 DNA was then electrophoresed on a 0.7% agarose gel, and the ~7.2 kb XbaI-KpnI restriction fragment of plasmid pIN-III-ompA3 was isolated, purified, and resuspended in TE buffer.

About 30 μg of plasmid pIN-III-ompA3-HGH were dissolved in 100 μl of a buffer containing 20 mM KCl; 10 mM Tris-HCl, pH=7.4; 10 mM MgCl$_2$; 1 mM DTT; and 100 μg/ml BSA. About 30 units of restriction enzyme HpaI were added to the solution of DNA, and the resulting reaction was incubated at 37° C. for 2 hours. About 10 μl of 1M Tris-HCl, pH=8.0, and about 0.1 unit of bacterial alkaline phosphatase (Worthington Biochemical Co., Freehold, N.J. 07728) were added to the solution of HpaI-digested plasmid pIN-III-ompA3-HGH DNA, and the incubation at 37° C. was continued for another hour. The reaction mixture was sequentially extracted with phenol:chloroform (1:1) and chloroform and then was loaded onto an ~0.7% agarose gel and electrophoresed to isolate the ~8.1 kb HpaI restriction fragment. The ~8.1 kb, phosphatase-treated, HpaI restriction fragment was recovered from the gel, purified, and resuspended in TE buffer.

About 2 μg of the ~7.2 kb KpnI-XbaI restriction fragment of plasmid pIN-III-ompA3 and 2 μg of the ~8.1 kb, phosphatase-treated, HpaI restriction fragment of plasmid pIN-III-ompA3-HGH were dissolved in about 35 μl of a buffer containing 100 mM NaCl; 6.5 mM Tris-HCl, pH=7.5; 8 mM MgCl$_2$; 1 mM β-mercaptoethanol; and 75 picomoles of the oligonucleotide primer depicted below:

The primer (3000 cpm/pmol) had been phosphorylated using T4 polynucleotide kinase (Pharmacia P-L Biochemicals, Milwaukee, Wis. 53205) and γ-[$^{32}$P]-ATP. The mixture of DNA was boiled at 100° C. for 3 minutes, then incubated at 30° C. for 30 minutes, and then incubated at 4° C. for 30 minutes. A 10 μl aliquot of the DNA was removed and electrophoresed on an ~0.7% agarose gel to monitor the annealing reaction, and as desired, a faint new band corresponding to open-circular plasmid DNA was observed.

About 1 μl of 10 mM dATP, 1 μl of 10 mM dCTP, 1 μl of 10 mM TTP, 1 μl of 10 mM dGTP, 2 μl of 10 mM ATP, 1.5 μl of 0.1M DTT, 1 μl of Klenow (~4 units), and 1.5 μl of T4 DNA ligase (~3 units, BRL) were then added to the remaining 25 μl of the DNA mixture prepared above, and the resulting reaction was incubated at 12.5° C. for 16 hours. About 10 μl of the DNA were then used to transform E. coli K12 RV308 cells (NRRL B-15624) that were made competent for transformation in substantial accordance with the procedure described above for JA221 cells. E. coli K12 RV308 cells are also publicly available from the ATCC under the accession number ATCC 31608.

The transformed cells were plated onto L-agar plates containing 100 μg/ml ampicillin, and the ampicillin-resistant transformants were examined for the presence of plasmid pIN-III-ompA3-HGH1 DNA. Positive identification of the pIN-III-ompA3-HGH1 DNA was made on the basis of (1) absence of an EcoRI restriction site; (2) ability to hybrize to an oligonucleotide probe of sequence: 5'-$^{32}$P-GCAGGCCTTCCCAACC-3'; and (3) DNA sequence analysis. As noted above, plasmid pIN-III-ompA3-HGH1 differs from plasmid pIN-III-ompA3-HGH in that the former plasmid has no EcoRI restriction sites and drives expression and secretion of HGH in E. coli. The DNA and associated amino acid sequences at the junction of the ompA signal peptide-encoding and HGH-encoding DNA sequences of plasmid pIN-III-ompA3-HGH1 are depicted below:

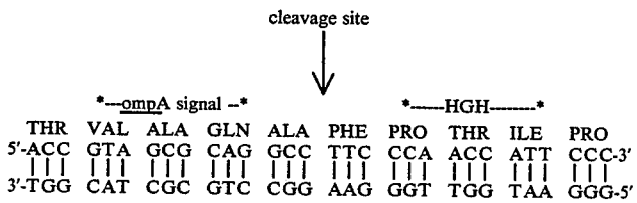

4. Expression of the Human Growth Hormone Gene in E. coli Transformants Carrying Plasmid pIN-III-ompA3-HGH1

The E. coli K12 RV308/pIN-III-ompA3HGH1 cells were grown for 16 hours at 37° C. in one liter of L broth that contained 100 μg/ml ampicillin. No isopropyl β-D-thiogalactopyranoside (IPTG) was added to induce the cells, although expression levels may be higher when IPTG is added to the culture medium. All subsequent steps were carried out at 4° C. The cells were collected by centrifugation, and the pellet was completely resuspended in 50 ml of a solution composed of 20% sucrose and 10 mM Tris-HCl, pH=7.5. About 2.5 ml of 0.5M EDTA, pH=8.0, were added to the solution, which was then incubated on ice for 30 minutes. The resuspended cells were pelleted by centrifugation, and the pellet was resuspended in 50 ml of cold distilled water by vigorous agitation to subject the cells to osmotic shock. The mixture was then incubated for 30 minutes on ice and again centrifuged for 5 minutes to pellet the cells. The supernatant was carefully removed and used for HGH purification, isolation, and other biochemical studies.

The supernatant from the osmotic-shock step was applied directly to a column (4.4 cm×25 cm) of Fast-Flow Q Sepharose (Pharmacia Inc., 800 Centennial Ave., Piscataway, NJ 08854) equilibrated with a buffer consisting of 50 mM Tris-HCl, pH=8, and the proteins were eluted with an increasing linear gradient of NaCl in the same buffer. Fractions containing human growth hormone were localized by assaying on an analytical Mono Q HR515 (0.5 cm×5 cm) (Pharmacia, Inc.) column.

The pooled fractions from the Fast-Flow Q column were applied to a column of Sephacryl S-200 (Pharmacia, Inc.). A 30 ml sample (approximately 5% of total bed volume) was applied to a column (3.2 cm×77 cm) equilibrated with 50 mM Tris-HCl, pH=8, at a flow rate of 3.5 cm/hr. The sample was eluted with the equilibration buffer; the column resolved the monomer form of HGH from dimers and higher oligomers, as well as from containing bacterial proteins. In some cases, the HGH solution obtained after size-exclusion chromatography was solvent-exchanged on a column of Sephadex G-25 (Pharmacia, Inc.). A volume equal to 20–25% of the total column volume was loaded onto the column, which had been equilibrated with water adjusted to pH=8 by the addition of ammonium hydroxide. This same solvent was used to elute the HGH from the column. After the solvent-exchange step, the protein solution was lyophylized, and the HGH was stored as a dry powder. The HGH was estimated to be greater than 90% pure following these chromatographic steps.

Analysis of total-cell extracts and periplasmic fractions by SDS-polyacrylamide-gel electrophoresis demonstrated that about 6% of the total cellular protein in the E. coli K12 RV308/pIN-III-ompA3-HGH1 cells was HGH, that most of the HGH was localized in the periplasm of the cell, and that about 30% of the total periplasmic protein was HGH. About 10–15 μg of HGH could be obtained from the periplasmic fraction per each $A_{600}$ unit of cells in the culture. The purified HGH was shown to have the correct amino terminus (PHE) by amino-acid-sequence analysis and to have the correct disulfide bonds and secondary structure by trypsin mapping and circular dichroism.

The foregoing results confirm that a structural gene coding for a other desired polypeptide can be expressed in transformed bacterial hosts using a recombinant plasmid cloning vehicle constructed in accordance with the present invention, and significant quantities of the desired polypeptide can be expressed and efficiently secreted thereby. However, it will be apparent to those skilled in the art that the embodiments described herein are by way of illustration and not of limitation, and that other recombinant plasmid cloning vehicles with which exogenous genes may be expressed may be utilized without departing from the spirit and scope of the present invention, as set forth in the appended claims.

We claim:

1. A recombinant plasmid suited for use as a cloning vehicle for expression of at least one polypeptide in a transformed bacterial host, said plasmid comprising a 1. first DNA sequence coding for the promoter of the lipoprotein gene of *Escherichia coli*, linked in reading phase with (a) a second DNA sequence located downstream of said lipoprotein promoter and coding for the segment between positions −40 and +65 of the β-galactosidase promoter-operator of *Escherichia coli*, (b) a third DNA sequence located downstream of said second DNA sequence and coding for the signal peptide of the ompA gene of *Escherichia coli*, (c) a fourth DNA sequence located downstream of said third DNA sequence and coding for the amino acid sequence of said at least one polypeptide, said plasmid also comprising a fifth DNA sequence coding for the lacI gene of *Escherichia coli*.

2. A plasmid in accordance with claim 1 further comprising a sixth DNA sequence located downstream of said lipoprotein promoter and upstream of said second DNA sequence and coding for at least a portion of the 5'-untranslated region of said lipoprotein gene.

3. A plasmid in accordance with claim 2 further comprising a seventh DNA sequence located downstream of said fourth DNA sequence and comprising the 3'-untranslated region and the transcription termination signal of said lipoprotein gene, wherein said fourth DNA sequence is located upstream of said 3'-untranslated region and wherein said 3'-untranslated region is located upstream of said transcription termination signal.

4. A plasmid in accordance with claim 3 wherein said seventh DNA sequence further comprises a terminal portion of the structural sequence of said lipoprotein gene, said terminal portion coding for the DNA segment commencing with position +168 of said lipoprotein structural gene, and wherein said terminal portion is located upstream of said 3'-untranslated region and downstream of said fourth DNA sequence.

5. A plasmid in accordance with claim 4 wherein said at least one polypeptide comprises the β-lactamase of *Escherichia coli*.

6. A plasmid in accordance with claim 4 wherein said at least one polypeptide comprises a mammalian hormone.

7. A plasmid in accordance with claim 6 wherein said mammalian hormone is human growth hormone.

8. A recombinant plasmid suited for use as a cloning vehicle for expression of at least one polypeptide in a transformed bacterial host, said plasmid comprising a first DNA sequence comprising DNA coding for the promoter of the lipoprotein gene of *Escherichia coli* and at least a portion of the 5'-untranslated region of the lipoprotein gene of *Escherichia coli*, said portion of said 5'-untranslated region located downstream of said promoter, said first DNA sequence linked with (a) a second DNA sequence located downstream of said first DNA sequence and coding for the segment between positions −40 and +65 of the β-galactosidase promoter-operator of *Escherichia coli*, (b) a third DNA sequence located downstream of said second DNA sequence and coding for the signal peptide of the ompA gene of *Escherichia coli*, (c) a fourth DNA sequence located downstream of said third DNA sequence and coding for a translation initiation codon adjacent the recognition sequence of at least one restriction endonuclease for incorporation in said plasmid of a fifth DNA sequence coding for the amino acid sequence of said at least one polypeptide, and (d) a sixth DNA sequence located downstream of said fifth DNA sequence and coding for the 3'-untranslated region and the transcription termination signal of said lipoprotein gene, said plasmid also comprising a seventh DNA sequence coding for the lacI gene of *Escherichia coli*.

9. A plasmid in accordance with claim 8 wherein said sixth DNA sequence further comprises a terminal portion of the structural sequence of said lipoprotein gene, said terminal portion coding for the DNA segment commencing with position +168 of said lipoprotein structural gene, and wherein said terminal portion is located upstream of said 3'-untranslated region and downstream of said fourth DNA sequence.

10. A plasmid in accordance with claim 9 wherein said fourth DNA sequence comprises DNA sequences recognized by the Eco RI, Hind III and Bam HI restriction endonucleases.

11. A plasmid which is selected from the group consisting of pIN-III-ompA1, pIN-III-ompA2 and pIN-III-ompA3.

12. A method for producing a polypeptide in a transformed bacterial host comprising the steps of (a) selecting a recombinant plasmid comprising a first DNA sequence comprising DNA coding for the promoter of the lipoprotein gene of *Escherichia coli* and at least a portion of the 5'-untranslated region of the lipoprotein gene of *Escherichia coli*, said portion of said 5'-untranslated region located downstream of said promoter, said first DNA sequence linked with (i) a second DNA sequence located downstream of said first DNA sequence and coding for the segment between positions −40 and +65 of the β-galactosidase promoter-operator of *Escherichia coli*, (ii) a third DNA sequence located downstream of said second DNA sequence and coding for the signal peptide of the ompA gene of *Escherichia coli*, (iii) a fourth DNA sequence located downstream of said third DNA sequence and coding for a translation initiation codon adjacent the recognition sequence of at least one restriction endonuclease for incorporation in said plasmid of a fifth DNA sequence coding for the amino acid sequence of said polypeptide, and (iv) a sixth DNA sequence located downstream of said fifth DNA sequence and coding for the 3'-untranslated region and the transcription termination signal of said lipoprotein gene, said plasmid also comprising a seventh DNA sequence coding for the lacI gene of *Escherichia coli*, (b) inserting said fifth DNA sequence within said fourth DNA sequence, (c) inserting the plasmid in said bacterial host by transformation, (d) isolating and culturing said bacterial host to produce a large population of said bacterial host, (e) adding to said population a lactose inducer, and (f) producing said polypeptide from said population.

13. A bacterial transformant comprising a plasmid comprised of a first DNA sequence comprising DNA coding for the promoter of the lipoprotein gene of *Escherichia coli* and at least a portion of the 5'-untranslated region of the lipoprotein gene of *Escherichia coli*, said portion of said 5'-untranslated region located downstream of said promoter, said first DNA sequence linked with (a) a second DNA sequence located downstream of said first DNA sequence and coding for the segment between positions −40 and +65 of the β-galactosidase promoter-operator of *Escherichia coli*, (b) a third DNA sequence located downstream of said second DNA sequence and coding for the signal peptide of the ompA gene of *Escherichia coli*, (c) a fourth DNA sequence located downstream of said third DNA sequence coding for a translation initiation codon adjacent the recognition sequence of at least one restriction endonuclease for incorporation in said plasmid of a fifth DNA sequence coding for the amino acid sequence of a polypeptide, and (d) a sixth DNA sequence located downstream of said fifth DNA sequence and coding for the 3'-untranslated region and the transcription termination signal of said lipoprotein gene, said plasmid also comprising a seventh DNA sequence coding for the lacI gene of *Escherichia coli*, said transformant being capable of producing the polypeptide upon fermentation in an aqueous nutrient medium containing assimilable sources fo carbon, nitrogen and inorganic substances, and also containing a lactose inducer.

14. The transformant of claim 13 wherein the transformant is selected from the species *Escherichia coli*.

15. The transformant of claim 14 wherein said plasmid is selected from the group consisting of pINIII-ompA1, pINIII-ompA2 and pINIII-ompA3.

* * * * *